US008765368B2

(12) United States Patent
Willey et al.

(10) Patent No.: US 8,765,368 B2
(45) Date of Patent: Jul. 1, 2014

(54) CANCER RISK BIOMARKER

(75) Inventors: James C. Willey, Toledo, OH (US);
Thomas M. Blomquist, Perrysburg, OH (US); Erin L. Crawford, Rossford, OH (US); D'Anna N. Mullins, Maumee, OH (US)

(73) Assignee: The University of Toledo, Toledo, OH (US)

( * ) Notice: Subject to any disclaimer, the term of this patent is extended or adjusted under 35 U.S.C. 154(b) by 420 days.

(21) Appl. No.: 12/212,003

(22) Filed: Sep. 17, 2008

(65) Prior Publication Data

US 2009/0181383 A1 Jul. 16, 2009

Related U.S. Application Data

(60) Provisional application No. 60/972,984, filed on Sep. 17, 2007.

(51) Int. Cl.
*C12Q 1/68* (2006.01)
*G01N 33/574* (2006.01)

(52) U.S. Cl.
CPC ........ *G01N 33/574* (2013.01); *C12Q 2545/114* (2013.01); *C12Q 2600/157* (2013.01); *C12Q 1/6886* (2013.01); *C12Q 2600/16* (2013.01); *G01N 2800/50* (2013.01)
USPC ........................................................ 435/6.1

(58) Field of Classification Search
None
See application file for complete search history.

(56) References Cited

U.S. PATENT DOCUMENTS

| | | | |
|---|---|---|---|
| 5,639,606 A | 6/1997 | Willey | |
| 5,643,765 A | 7/1997 | Willey | |
| 5,789,167 A | 8/1998 | Konrad | |
| 5,866,617 A | 2/1999 | Hausheer et al. | |
| 5,876,978 A | 3/1999 | Willey | |
| 6,001,817 A | 12/1999 | Shaw | |
| 6,001,991 A | 12/1999 | Dean | |
| 6,080,727 A | 6/2000 | Zupi | |
| 6,218,122 B1 | 4/2001 | Friend | |
| 6,229,911 B1 | 5/2001 | Balaban et al. | |
| 6,316,272 B1 | 11/2001 | Mack | |
| 7,476,502 B2 | 1/2009 | Willey | |
| 7,527,930 B2 | 5/2009 | Willey et al. | |
| 2001/0051344 A1* | 12/2001 | Shalon et al. | 435/6 |
| 2003/0186246 A1 | 10/2003 | Willey et al. | |
| 2004/0197785 A1 | 10/2004 | Willey et al. | |
| 2005/0214826 A1* | 9/2005 | Mor et al. | 435/6 |
| 2005/0260586 A1 | 11/2005 | Demuth et al. | |
| 2006/0183144 A1 | 8/2006 | Willey et al. | |
| 2006/0188908 A1 | 8/2006 | Willey et al. | |
| 2006/0188909 A1 | 8/2006 | Willey et al. | |
| 2006/0190192 A1 | 8/2006 | Willey et al. | |
| 2006/0194216 A1 | 8/2006 | Willey et al. | |
| 2007/0092892 A1 | 4/2007 | Willey et al. | |
| 2007/0092893 A1 | 4/2007 | Willey et al. | |
| 2007/0134688 A1* | 6/2007 | Symmans et al. | 435/6 |
| 2008/0311569 A1 | 12/2008 | Willey et al. | |
| 2009/0181383 A1 | 7/2009 | Willey et al. | |
| 2009/0226923 A1 | 9/2009 | Willey et al. | |
| 2010/0184029 A1 | 7/2010 | Willey et al. | |

FOREIGN PATENT DOCUMENTS

| | | |
|---|---|---|
| WO | 9858083 A2 | 12/1998 |
| WO | WO 99/01581 A1 | 1/1999 |
| WO | 02072866 A2 | 9/2002 |
| WO | 03040317 A2 | 5/2003 |
| WO | 03082078 A2 | 10/2003 |
| WO | 03083051 A2 | 10/2003 |
| WO | 2005032495 A2 | 4/2005 |
| WO | 2005086679 A2 | 9/2005 |
| WO | 2005106036 A2 | 11/2005 |
| WO | 2006079033 A2 | 7/2006 |
| WO | 2006079034 A2 | 7/2006 |
| WO | 2006079048 A2 | 7/2006 |
| WO | 2006079087 A2 | 7/2006 |
| WO | 2007028161 A2 | 3/2007 |
| WO | 2007028162 A2 | 3/2007 |
| WO | 2009039190 A1 | 3/2009 |
| WO | 2009120802 A1 | 10/2009 |
| WO | 2009123990 A1 | 10/2009 |

OTHER PUBLICATIONS

Crawford et al. (Cancer Research, 60, 1609-1618.*
Thisted (1998) What is a P-Value. University of Chicago. May 25, 1998. accessed from http://www.stat.uchicago.edu/~thisted. six pages.*
Michiels et al. Lancet, 2005; 365:488-492.*
Slonin, Nature Genetics Supplement, vol. 32, Dec. 2002, pp. 502-508.*
Baker. Journal of the National Cancer Institute, vol. 95, No. 7, Apr. 2, 2003, pp. 511-515.*
Enard et al (Science. Apr. 12, 2002; 296(5566):340-43).*
Hoshikawa et al (2003) Physiol Genomics 12:209-219, 2003.*
Shedden et al. (Nature Medicine, Aug. 2008, vol. 14, No. 8, pp. 822-827).*
Lee, Wooin et al. Cancer pharmacogenomics: powerful tools in cancer chemotherapy and drug development. The Oncologist 2005. vol. 10 pp. 104-111.*
Chan. Integrating Transcriptomics and Proteomics. 2006. obtained from http://www.dddmag.com/analytical-software-for-biological-studies.aspx. six pages.*
Chen et al. (Molecular and Cellular Proteomics 1:304-313, 2002) ).*
Actor, et al. A flexible bioluminescent-quantitative polymerase chain reaction assay for analysis of competitive PCR amplicons. Journal of Clinical Laboratory Analysis. 1999; 8 pages.

(Continued)

*Primary Examiner* — Juliet Switzer
(74) *Attorney, Agent, or Firm* — MacMillan, Sobanski & Todd, LLC

(57) ABSTRACT

The present disclosure relates to methods and compositions for identifying biomarkers that indicate a biological state, in particular cancer or predisposition to cancer. Also provided are methods and compositions for identifying a greater risk for a cancer-related condition in an subject.

6 Claims, 20 Drawing Sheets

(56) References Cited

OTHER PUBLICATIONS

Alizadeh, et al. Distinct types of diffuse large B-cell lymphoma identified by gene expression profiling. Nature. 2000; 403(6769): 503-511.
Apostolakos, et al. Measurement of gene expression by multiplex competitive polymerase chain reaction. Anal. Biochem. 1993; 213: 277-284.
Crawford, et al. Normal bronchial epithelial cell expression of glutathione transferase P1, glutathione transferase M3, and glutathione peroxidase is low in subjects with bronchogenic carcinoma. Cancer Res. 2000; 60: 1609-1618.
Crawford, et al. Multiplex standardized RT-PCR for expression analysis of many genes in small clinical samples. Biochemical and Biophysical Research Communications. 2002; 293: 509-516.
Damia, et al. Expression of genes involved in nucleotide excision repair and sensitivity to cisplatin and melphalan in human cancer cell lines. Eur J Cancer. 1998; 34(11):1783-8.
Demuth, et al. The gene expression index c-myc X E2F-1/p21 is highly predictive of malignant phenotype in human bronchial epithelial cells—rapid communication. American Journal of Respiratory Cell and Molecular Biology. 1998; 19: 18-24.
Golub, et al. 1999. Molecular classification of cancer: class discovery and class prediction by gene expression monitoring. Science.1999; 286. 531-537.
Kihara, et al. Prediction of sensitivity of esophageal tumors to adjuvant chemotherapy by cDNA microarray analysis of gene-expression profiles. Cancer Res. 2001; 61: 6474-6479.
Kool, et al. Analysis of expression of cMOAT (MRP2), MRP3, MRP4, and MRP5, homologues of the multidrug resistance-associated protein gene (MRP1), in human cancer cell lines. Cancer Res. 1997; 57(16):3537-47.
Peters, et al. Quantitative analysis of NF1 and OMGP gene transcripts in sporadic gliomas, sporadic meningiomas and neurofibromatosis type 1-associated plexiform neurofibromas. Acta Neuropathologica. 1999; 97 (6): 547-551. (Abstract Only).
Prakash, et al. DNA repair genes and proteins of *Saccharoyces cerevisiae*. Annu. Rev. Genet. 1993; 27: 33-70.
Robinson, et al. Recent advance in molecular biological techniques and their relevance to pulmonary research. Occasional Review. 2000; 11 pages.
Scherf, et al. A gene expression database for the molecular pharmacology of cancer. Nat Genet. 2000; 24: 236-244.
Spanakis. Problems related to the interpretation of autoradiographic data on gene expression using common constitutive transcripts as controls. Nucleic Acids Research. 1993; 21 (16): 3809-3819. (Abstract Only).
Steinbach, et al. Response to chemotherapy and expression of the genes encoding the multidrug resistance-associated proteins MRP2, MRP3, MRP4, MRP5, and SMRP in childhood acute myeloid leukemia. Clin Cancer Res. 2003; 9(3):1083-6.
Weaver, et al. Comparison of expression patterns by microarray and standardized RT-PCR analyses in lung cancer cell lines with varied sensitivity to carboplatin. Proc. Am. Assoc.Cancer Res. 2001; 42: 606.
Willey, et al. Expression measurement of many genes simultaneously by quantitative RT-PCR using standardized mixtures of competitive templates-rapid communication. American Journal of Respiratory Cell and Molecular Biology. 1998; 19: 6-17.
Willey, et al. Quantitative RT-PCR measurement of cytochromes p4a50 1A1, 1B1, and 2B7, microsomal epoxide hydrolase, and NADPH oxidereductase expression in lung cells of smokers and non-smokers. Am. J. Respir. Cell Mol. Biol. 1997; 17:114-124.
Zembutsu, et al. Genome-wide cDNA microarray screening to correlate gene expression profiles with sensitivity of 85 human cancer xenografts to anticancer drugs. Cancer Res. 2002; 62: 518-527.
Weaver, et al. ABCC5, ERCC2, XPA and XRCC1 transcript abundance levels correlate with cisplatin chemoresistance in non-small cell lung cancer cell lines. Mol Cancer. May 9, 2005;4(1):18 (8 pages).
Mullins, N.D. et al., "CEBPG Transcription Factor Correlates with Antioxidant and DNA Repair Genes in Normal Bronchial Epithelial Cells but not in Individuals with Bronchogenic Carcinoma," BMC Cancer, 2005, vol. 5, No. 141.
PCT International Preliminary Report on Patentability, PCT/US2008/076702 filed Sep. 17, 2008, dated Mar. 24, 2010.
PCT International Preliminary Report on Patentability, PCT/US2009/038845 filed Mar. 30, 2009, dated Oct. 5, 2010.
PCT International Search Report and the Written Opinion, PCT/US2008/038845 filed Mar. 30, 2009, dated Aug. 28, 2009.
Yin, J. et al., "The DNA Repair Gene XRCC1 and Genetic Susceptibility of Lung Cancer in a Northeastern Chinese Population," Lung Cancer, May 2007, vol. 56, No. 2, pp. 153-160.

* cited by examiner

| Log TA | Binary Index | Simple Moving Average |
|---|---|---|
| 3.18 | 1 | |
| 3.18 | 1 | |
| 3.26 | 0 | |
| 3.28 | 1 | |
| 3.40 | 0 | |
| 3.41 | 0 | |
| 3.43 | 0 | |
| 3.45 | 1 | 0.52 |
| 3.54 | 0 | |
| 3.56 | 0 | |
| 3.57 | 0 | |
| 3.58 | 1 | |
| 3.61 | 1 | |
| 3.62 | 1 | |
| 3.64 | 1 | |

0.52 is the average of:
1,1,0,1,0,0,0,1,0,0,0,1,
1,1,1

FIG. 8

CANCER RISK BIOMARKER

CROSS-REFERENCE

This application claims the benefit of U.S. Provisional Application No. 60/972,984, filed Sep. 17, 2007, which application is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FEDERALLY SPONSORED RESEARCH OR DEVELOPMENT

Work described herein was supported by United States government under National Institutes of Health Grant Nos. CA85147, CA81126, CA95806 or CA103594.

SEQUENCE LISTING

The instant application contains a Sequence Listing which has been submitted via EFS-web and is hereby incorporated by reference in its entirety. The ASCII copy, created on Oct. 28, 2013, is named 420_52554_SEQ_LIST_D2008-09-1.txt, and is 15,912 bytes in size.

BACKGROUND

Assessing the correlation between a particular variation in DNA sequence, or polymorphism, and risk for a particular condition has been a dominant paradigm for many years. A common limitation of such studies, however, is that they involve assessment of a single polymorphism or occasionally, a few polymorphisms. Further, although the polymorphism assessed typically resides within a gene associated with a particular biological state, the selection of a polymorphism for study can be largely empiric, e.g., not being based on known function. As multiple infrequent polymorphisms at different sites may all contribute to risk, and key polymorphisms may not have been identified through functional tests, a statistically valid assessment may require very large study populations, so large as to be impractical. Thus, there remains a need for new approaches to identify biomarkers that can diagnose undesirable conditions and serve as therapeutic targets.

Bronchogenic carcinoma (BC) is an example of such a condition. BC is the leading cause of cancer-related death in the United States. While cigarette smoking is the primary risk factor, only some heavy smokers acquire the disease. Cigarette smoking is also the primary cause of other pulmonary conditions such as chronic obstructive pulmonary disease (COPD). COPD is one of the most common chronic conditions and the fourth leading cause of death in the United States. Identifying those at greater risk for BC and/or COPD can enhance development of methods and compositions for early detection, as well as methods and compositions for treating and/or preventing the disease. The instant invention relates to such methods and compositions for identifying individuals at risk for BC and/or COPD, as well as other biological states, including e.g., other cancer and/or other lung-related conditions.

SUMMARY

The present disclosure provides a method of identifying a cancer-related condition or a lung-related condition in a subject comprising obtaining a sample from the subject, wherein the sample comprises a nucleic acid region corresponding to a 5' regulatory region of CEBPG; and comparing the nucleic acid region to a nucleic acid sequence consisting of a 5' regulatory region of CEBPG±about 100 bases, wherein a nucleotide difference indicates the subject has the cancer-related or the lung-related condition.

Also provided herein is a method of identifying a cancer-related condition or a lung-related condition in a subject comprising obtaining a sample from the subject, wherein the sample comprises a nucleic acid region corresponding to a 3' un-translated region of CEBPG; and comparing the nucleic acid region to a nucleic acid sequence consisting of a 3' un-translated region of CEBPG±about 100 bases, wherein a nucleotide difference indicates the subject has the cancer-related or the lung-related condition.

Further provided herein is a method of identifying a cancer-related condition or a lung-related condition in a subject comprising obtaining a sample from the subject, wherein the sample comprises a nucleic acid region corresponding to a bZip region of CEBPG; and comparing the nucleic acid region to a nucleic acid sequence consisting of a bZip region of CEBPG±about 100 bases, wherein a nucleotide difference indicates the subject has the cancer-related or the lung-related condition.

The present disclosure also provides a method of identifying a cancer-related condition or a lung-related condition in an subject comprising obtaining a sample from the subject, wherein the sample comprises a nucleic acid region corresponding to a CEBPG recognition site of XRCC1, ERCC5, SOD1, GSTP1 and/or GPX1; and comparing the nucleic acid region to a nucleic acid sequence consisting of a CEBPG recognition site of XRCC1, ERCC5, SOD1, GSTP1 and/or GPX1±about 100 bases, wherein a nucleotide difference indicates the subject has the cancer-related or the lung-related condition.

BRIEF DESCRIPTION OF THE FIGURES

The novel features of the disclosure are set forth with particularity in the appended claims. A better understanding of the objects, features and advantages of the present disclosure will be obtained by reference to the following detailed description that sets forth illustrative embodiments, in which the principles of the disclosure are utilized, and the accompanying drawings of which:

FIG. 8 illustrates an example, wherein the 14 closest (7 higher and 7 lower) transcript abundance value binary indices were averaged to yield a fraction of cancer occurrence.

DETAILED DESCRIPTION

The present disclosure relates to methods and compositions for identifying biomarkers that indicate a biological state, in particular transcription factor biomarkers and genes that can be regulated by such transcription factor biomarkers. The disclosure also relates to identifying polymorphisms in such transcription factors and regulated genes indicative of the biological state. The biomarkers and polymorphisms identified find use in diagnostic and treatment approaches, e.g., in some embodiments the invention provides methods and kits for detecting bronchogenic carcinoma and risks thereof.

I. Methods and Compositions for Identifying Biomarkers

A. Lack of Correlation Approach

In one aspect, the disclosure relates to methods for identifying biomarkers that indicate a biological state. In some embodiments, the method involves identifying lack of correlation between expression levels of a transcription factor and another gene in a given biological state. In some embodiments, the other gene is a gene known to be associated with a given biological state and the method involves identifying new transcription factor biomarkers. In some embodiments, the transcription factor is known to be associated with a given biological state and the method involves identifying new biomarkers that are other genes.

A "biological state" as used herein can refer to any phenotypic state, for e.g., a clinically relevant phenotype or other metabolic condition of interest. Biological states can include, e.g., a disease phenotype, a predisposition to a disease state or a non-disease state; a therapeutic drug response or predisposition to such a response, an adverse drug response (e.g. drug toxicity) or a predisposition to such a response, a resistance to a drug, or a predisposition to showing such a resistance, etc. In some embodiments, the drug may be and anti-tumor drug.

Figure 1:
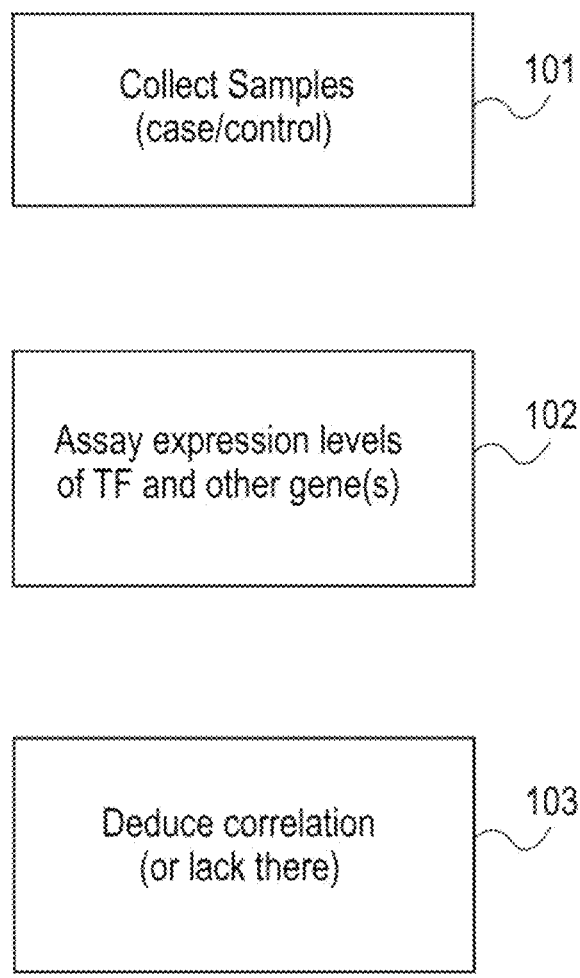
FIG. 1 illustrates the overall process for identifying biomarkers.

FIG. 1 illustrates the overall process for identifying biomarkers in some embodiments disclosed herein. At step 101, a representative sample set of case samples and control samples are collected. The control samples are samples that correspond to a particular normal biological state. For example, a control sample may be obtained from an individual that exhibits a particular normal state. For example, the control sample may be obtained from the normal bronchial epithelium of a patient with low risk for bronchogenic carcinoma or COPD. Conversely, a case sample may be obtained from the normal bronchial epithelium of a patient at high risk for bronchogenic carcinoma or COPD and therefore has a biological state that does not correspond to the biological state observed in control individuals who are at low risk. Alternatively, a control sample may be obtained from a cancer tissue with a biological state that corresponds to lack of response to a drug, while a case sample may be obtained from a cancer tissue with a biological state that corresponds to response to the drug.

In some embodiments, a plurality of case samples and control samples are used. A plurality refers to, e.g., 2 or more. Preferably more than about 10 case and more than about 10 control samples are collected for use. Preferably more than about 20 case samples and more than about 20 control samples, preferably more than about 50 case samples and more than about 50 control samples, preferably more than about 100 case samples and more than about 100 control samples, are collected for use.

Case/control samples can include, but not be limited to, a swab of culture, a brush of epithelial cells, a pinch of tissue, a biopsy extraction, or a vial of a biological fluid. Tissue can include, but not be limited to, organs, tumors, lymph nodes, arteries, aggregates of cells and/or individual cells. Biological fluids can include, but not be limited to, saliva, tears, mucus, lymph fluids, sputum, stool, pleural fluid, pericardial fluid, lung aspirates, exudates, peritoneal fluid, plasma, blood, serum, white blood cells, cerebral spinal fluid, synovial fluid, amniotic fluid, milk, semen, urine, and the like, as well as cell suspensions, cell cultures, or cell culture supernatants. Samples may be crude samples or processed samples, such as, but not limited to, obtained after various processing or preparation steps. For example, various cell separation methods, such as, but not limited to, magnetically activated cell sorting, may be applied to separate or enrich analytes of interest in a biological fluid, such as blood. A sample may also comprise a dilution, for example, diluted serum or dilutions of other complex and/or protein-rich mixtures. Preferred embodiments of the present disclosure can be practiced using small starting materials to yield quantifiable results.

At step 102, expression levels of a transcription factor and at least one other gene are assayed. The expression levels can be determined by measuring abundance of a nucleic acid transcript and/or protein translation product using any techniques known in the art. For example, in some embodiments, expression levels are assayed by assaying abundance of an mRNA transcript. In preferred embodiments, transcript levels are assayed using one or more methods described in U.S. Pat. No. 5,639,606; U.S. Pat. No. 5,643,765; U.S. Pat. No. 5,876,978; U.S. patent application Ser. No. 11/072,700; and U.S. Provisional Application Ser. No. 60/646,157.

For example, in some embodiments, assaying mRNA transcript abundance comprises measuring a nucleic acid corresponding to a transcription factor relative to its competitive template; co-measuring a nucleic acid corresponding to another gene with its competitive template; and obtaining a relation comparing values obtained from the co-measurements. The nucleic acid corresponding to the transcription factor (or other gene) can refer to an mRNA transcript of the transcription factor (or other gene) or a cDNA obtained from the mRNA. The relation obtained can be a comparison of values for the transcription factor, its competitive template, the other gene, and its competitive template. In preferred embodiments, the transcription factor and/or other gene is measured relative to a reference nucleic acid, e.g., as described in U.S. patent application Ser. Nos. 11/072,700 and 11/103,397.

This may entail co-amplifying a nucleic acid corresponding to a transcription factor with its competitive template; co-amplifying a nucleic acid corresponding to another gene with its competitive template; and obtaining a relation comparing amplified products obtained from the co-amplifications. The nucleic acid corresponding to the transcription factor (or other gene) can refer to an mRNA transcript of the transcription factor (or other gene) or a cDNA obtained from the mRNA. The relation obtained can compare amplified amounts of the transcription factor, its competitive template, the other gene, and its competitive template. In preferred embodiments, the transcription factor and/or other gene is measured relative to a reference nucleic acid, e.g., as described in U.S. patent application Ser. Nos. 11/072,700 and 11/103,397. Alternatively, co-measurement may involve amplifying signal from each nucleic acid and corresponding internal standard through binding of a sequence-specific probes, such as those used in branched chain-amplification.

At least one of the other nucleic acids being analyzed can serve as the reference nucleic acid. "Reference nucleic acid" as used herein can refer to a nucleic acid that is amplified as well as the nucleic acid to be analyzed. The nucleic acid can be "normalized" to a reference nucleic acid. In some embodiments, the reference nucleic acid serves as a control for loading, e.g., to control for cDNA loaded into the reaction. For example, in some preferred embodiments, the reference nucleic acid comprises a nucleic acid that is not expected to vary (or to vary significantly) among given biological specimen and/or in response to certain stimuli. For example, mRNA from a constitutively expressed gene may provide the reference nucleic acid. In some embodiments, known or potential housekeeping genes may provide the reference nucleic acid, including but not limited to human, mouse and/or rat glyceraldehydes-3-phosphate dehydrogenase (GAPD or GAPDH), β-actin, 28S RNA, 18S RNA, and/or other ribonuclear protein genes. Other housekeeping genes that have been used as internal standards in Northern analyses of gene expression may also be used. See, e.g., Devereux et al., *Nucleic Acids Res.* 12:387 (1984); Barbu et al., *Nucleic Acids Res.* 17:7115 (1989). In some embodiments, a competitive template for a reference nucleic acid may comprise a nucleic acid having a sequence similar to either strand of cDNA of a housekeeping gene, but having a distinguishable feature as described above.

Many different genes can provide reference nucleic acids. The choice of reference nucleic acid may depend on the tissues to be assayed and/or the biological states being studied. For example, β-actin varies little among different normal bronchial epithelial cell samples (see, e.g., Crawford et al., *Cancer Res.* 60:1609-1618 (2000)), but it may vary over about 100-fold in samples from different tissues, such as bronchial epithelial cells compared to lymphocytes. In some embodiments, the reference nucleic acid corresponds to a gene that is expressed in all or nearly all or the majority of all tissues; and/or is expressed at a high, substantially high or relatively high level In some embodiments, the competitive templates are provided in a standardized mixture. A "standardized mixture" as used herein can refer to a mixture comprising a number of internal standards, e.g., a number of competitive templates. In still some embodiments, a series of serially-diluted standardized mixtures is used to assay analytes in a mixture. "Serially-diluted standardized mixtures" can refer to two or more standardized mixtures in which one or more of the reagents in the standardized mixtures is serially-diluted. In some embodiments, one or more reagents in the standardized mixtures is serially-diluted relative to a different one or more of the reagents in the mixtures. For example, the series of standardized mixtures can provide competitive template for a transcription factor at a series of known concentrations relative to competitive template for another gene. Preparation and use of standardized mixtures are described in U.S. patent application Ser. Nos. 11/072,700 and 11/103,397.

Other methods for assaying mRNA transcript abundance can also be used. For example, real-time RT-PCR and/or hybridization assays can be used in some embodiments. For example, specific oligonucleotide probes for the relevant transcription factors and other genes can be used in hybridization techniques, as is known in the art. Any hybridization format for determining specific RNA levels can be used, including but not limited to Northern blots, slot blots, dot blots, and hybridization to oligonucleotide arrays, microarrays and other solid-phase approaches. Specificity of hybridization can be assessed by varying degrees of stringency of the hybridization conditions.

In some embodiments, expression levels are assayed by assaying abundance of a protein. To assess specific translation product (protein) expression levels, antibodies specific for the protein can be used readily. Again, any format known in the art for measuring specific protein levels can be used, including sandwich assays, ELISAs, immunoprecipitations, and Western blots. Any monoclonal antibody, polyclonal antibody, single chain antibody, or antibody fragment may be used in such assays.

Further, in some embodiments, such as methods provided in U.S. patent application Ser. No. 11/103,397, can be used. The patent application describes standardized immuno-PCR methods and compositions that can be used to measure protein copy number, protein-DNA hybrids, and/or protein-protein hybrids. Briefly, in some embodiments, internal standards can be used that comprise a known number of molecules of antigen (e.g. transcription factor protein) hybridized in equimolar amount to a highly specific, high affinity monoclonal antibody that in turn is covalently bound to a double stranded DNA molecule that serves as a template for PCR. A known quantity of internal standard for each of multiple genes can be combined in a standardized mixture of internal standards (SMIS). Due to the signal amplification power of PCR, a 1 mg batch of this SMIS in some embodiments can serve the world's needs for 5-10 years.

At step 103, correlation or lack thereof is deduced. That is, the method involves deducing whether or not expression levels of the transcription factor are correlated with expression levels of the other gene in control and/or case samples. In some embodiments, transcription factor expression levels represent the total amount of both wild type and mutant transcription factor transcripts. Where the biological state of interest is a disease state, e.g., a cancer-related condition, expression levels of the transcription factor and the other gene generally are correlated in control samples but not correlated in case samples.

Those of skill in the art will recognize that more than one transcription faction and/or other genes can be assayed. For example, in searching for a transcription factor biomarker, the expression levels of one or more additional genes associated with a biological state can be assayed. In searching for other genes (putatively regulated genes) that can serve as biomarkers, the expression levels of one or more transcription factors associated with a biological state can be assayed.

"Correlated" can refer to positive or negative correlation, preferably positive correlation. A correlation can be based on statistical significance, e.g, using one of tests described in the Examples. Conversely, "not correlated" can be based on a lack statistical significance, e.g., a lack of statistically significant correlation between expression level of a transcription factor and expression level of at least one other gene in case samples. "Not correlated," "lack of correlation" and other grammatical variations thereof, will refer to a lesser or reduced degree of correlation between the expression levels of two genes, e.g., in case samples compared to controls, e.g., a low or relatively low correlation. By detecting loss of correlation, a new biomarker can be identified. For example, where a gene is known to be associated with a given biological state, loss of correlation between expression levels of the gene and a given transcription factor in case samples can identify the transcription factor as a biomarker for the alternative biological state. As another example, where a transcription factor is known to be associated with a given biological state, loss of correlation between expression levels of the transcription factor and a given gene in case samples can identify the gene as a biomarker for the alternative biological state.

Without being limited to a particular theory or hypothesis, the loss of correlation in a disease state, e.g., in a cancer-related condition, may indicate loss of functional regulation of the gene by the transcription factor. "Transcription factor" or "TF" as used herein can refer to a gene or gene product that can influence the level of expression of another gene or gene product. In some embodiments, a transcription factor is a nucleic acid binding protein, e.g., a protein that can bind regulatory elements of other genes. Transcription factors can include, e.g., trans-acting factors, e.g., proteins that bind to cis-regulatory elements (eg. an enhancer or a TATA box) and thereby, directly or indirectly, affect the initiation of transcription. Common transcription factors include eukaryotic proteins that aid RNA polymerase to recognize promoters, as well as prokaryotic sigma factors. Transcription factors can activate and/or repress gene expression, resulting in up- or down-regulation.

Generally, the transcription factor regulates a given gene in control samples but not in case samples. Such genes may be referred to as "normally-regulated genes" or "putatively regulated genes," and grammatically similar variations and can also be referred to as "target genes" (TG). Regulation may be direct or indirect by various mechanistic bases. Methods of the instant invention facilitate exploration of various mechanistic bases, as described in the Examples below.

According to the paradigm used in this study, a) a normal phenotype results from regulated transcription of a group of genes by one or more TFs, b) the corresponding risk-conferring or disease phenotype results from sub-optimal interaction among those same genes, and c) each phenotype is identifiable and distinguishable by assaying expression levels. Accordingly, methods and compositions provided herein involve quantifying a) regulated transcription of a group of genes by one or more TFs that is associated with a normal phenotype, b) sub-optimal interaction among those same genes that is responsible for corresponding risk-conferring or disease phenotype, and c) using an expression level profile that identifies the normal from diseased or at-risk phenotype. The data presented here support the utility of this paradigm in identifying genes associated with risk for bronchogenic carcinoma (BC), as provided below.

Biomarkers for Bronchogenic Carcinoma and Other Cancer-Related Conditions

In one particular embodiment, transcription factor biomarkers can be identified for bronchogenic carcinoma (BC). BC is the leading cancer killer of both men and women in the United States and approximately 90% of cases can be attributed to cigarette smoking. The high death rate is in part because the disease typically is in advanced stage at time of diagnosis. The personal and financial cost of lung cancer in our society is high and likely to remain so for at least a generation because, even after smoking cessation, risk remains high for many years.

The cost to benefit ratio of promising BC screening studies could be markedly improved if a biomarker were available that accurately identified the approximately 10-15% of heavy smokers at risk for developing the disease. In other words, because about 10-15% of heavy smokers may develop bronchogenic carcinoma, a biomarker that accurately predicts individuals at greatest risk could substantially reduce cost of screening. Previously, sets of antioxidant and DNA repair genes were identified that were coordinately expressed in normal airway epithelial cells of non-BC individuals, but not in BC individuals, and identified transcription factors that are likely responsible for their regulation. Through analysis of these data, a biomarker was developed that accurately predicted which individuals were cancer patients.

In one embodiment, a biomarker comprises transcript abundance (TA) levels of one or more of the following genes: CEBPG, E2F1, E2F6, XRCC1, ERCC4, ERCC5, GPX1, GPX3, GSTM3, GSTP1, GSTT1, GSTZ1, MGST1, SOD1 and CAT.

Genes associated with BC include antioxidant (AO) and DNA repair (DNAR) genes. Such genes are expressed in the progenitor cells for BC, normal bronchial epithelial cells (NBEC), and are believed to protect against harmful effects of cigarette smoke (Willey et al, *American Journal of Respiratory Cell and Molecular Biology*, 19:16-24 (1998)). Inherited inter-individual variation in function of these genes has been shown to play a role in determining risk for BC (Spitz et al., *Cancer Epidemiol Biomarkers Prev.*, 12:689-98 (2003)). For example, transcript abundance of AO genes may be lower in NBEC of bronchogenic carcinoma individuals (BCI) compared to non-BCI (NBCI), suggesting that BCI are selected on the basis of poor antioxidant protection (Crawford et al, *Cancer Research*, 60, 1609-1618 (2000)). In the Crawford study, for example, there was a tendency towards correlation in transcript abundance between several pairs of AO or DNAR genes in NBCI, but not in BCI. Gene pairs included in that observation were GSTP1/GPX1, CAT/GPX3, and GPX3/SOD1.

In various embodiments, a cancer risk index is obtained by statistically analyzing transcript abundance levels in a sample, wherein at least one AO, at least one DNAR and at least one transcription factor correlated to said AO and said DNAR are analyzed to determine transcript abundance (TA) in the sample.

In one embodiment, at least one AO and one DNAR are analyzed. In another embodiment, at least on AO and one transcription factor correlated to an AO or a DNAR are analyzed to determine a threshold TA level. In a further embodiment, the transcription factor correlated to the AO and DNAR gene is CEBPG.

In various embodiments of the invention, at least one AO or one DNAR, including, but not limited to E2F1, E2F6, XRCC1, ERCC4, ERCC5, GPX1, GPX3, GSTM3, GSTP1, GSTT1, GSTZ1, MGST1, SOD1 and CAT, are analyzed. In one embodiment, TA levels are obtained for each of CEBPG, E2F1, E2F6, XRCC1, ERCC4, ERCC5, GPX1, GPX3, GSTM3, GSTP1, GSTT1, GSTZ1, MGST1, SOD1 and CAT. In some embodiments, where only an AO or DNAR is analyzed, the transcription factor analyzed is CEBPG. Thus, in various embodiments hereinabove, TA levels are determined for AO and DNAR genes and compared to threshold levels used as an index for increased cancer risk. In one embodiment, the cancer is bronchogenic carcinoma.

The threshold levels are obtained through statistical analysis, such as, but not limited to, obtaining for each gene (e.g., CEBPG, E2F1, E2F6, XRCC1, ERCC4, ERCC5, GPX1, GPX3, GSTM3, GSTP1, GSTT1, GSTZ1, MGST1, SOD1 and CAT) transcript abundance values, which are sorted in ascending order by log transformed transcript abundance values. Each sorted log transcript abundance value represents a subject, and that subject can be confirmed for bronchogenic carcinoma (BC) or confirmed to be non-bronchogenic carcinoma (non-BC). If the subject is BC, the transcript abundance value is linked to a binary value of one (1) (Table 13). If the individual was non-BC their transcript abundance value was linked to a binary value of zero (0) (Table 13). Thus, the data is presented in two columns: Log Transcript abundance Value and Binary Value for Cancer/non-Cancer.

One way to ascertain if a gene's level of Log Transcript abundance Value has a bearing or association with cancer diagnosis frequency is to perform a Histogram frequency analysis. If the data comprises fewer data points (e.g., 25 in each group; cancer and non-cancer) to plot a histogram that would accurately recapitulate the theoretical population that was sampled, a smoothing function can be used, such as a Simple Moving Averaging. In simple moving averaging, the average frequency of cancer occurrence in proximity to a given transcript abundance value was plotted. In one example, the 14 closest (7 higher and 7 lower) transcript abundance value binary indices were averaged to yield a fraction of cancer occurrence, as illustrated in FIG. 8.

This averaging function is repeated at each transcript abundance value in order to obtain a smoothing of the cancer frequency distribution. This smoothing process prevents or reduces the false interpretation of data-point "hiccups" and allows for assessment of the data's overall trends. After all Binary Index values have been smoothed into Simple Moving Averages, the simple moving averages are then plotted against Log TA values, and ascertained for empirical differences in cancer frequency distribution along a gene's expression (Log TA value).

Figure 9:
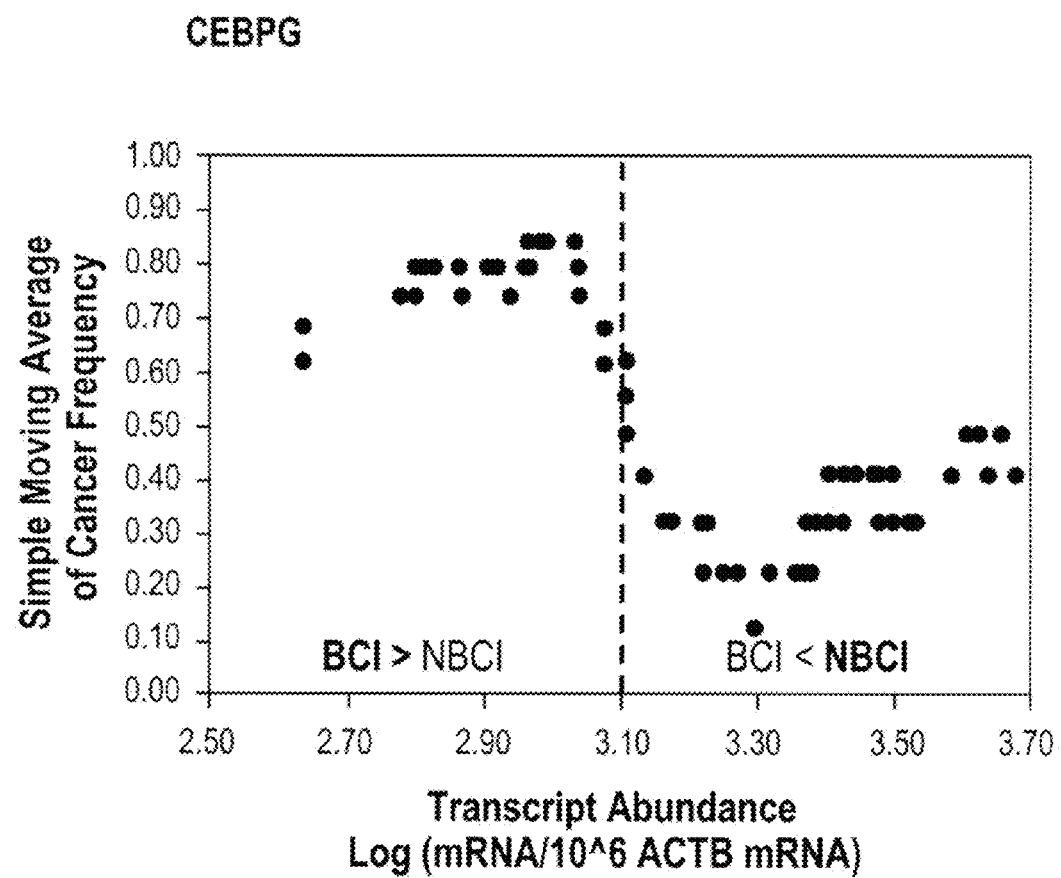
FIG. 9 illustrates TA values plotted for the CEBPG gene.
Figure 10A:
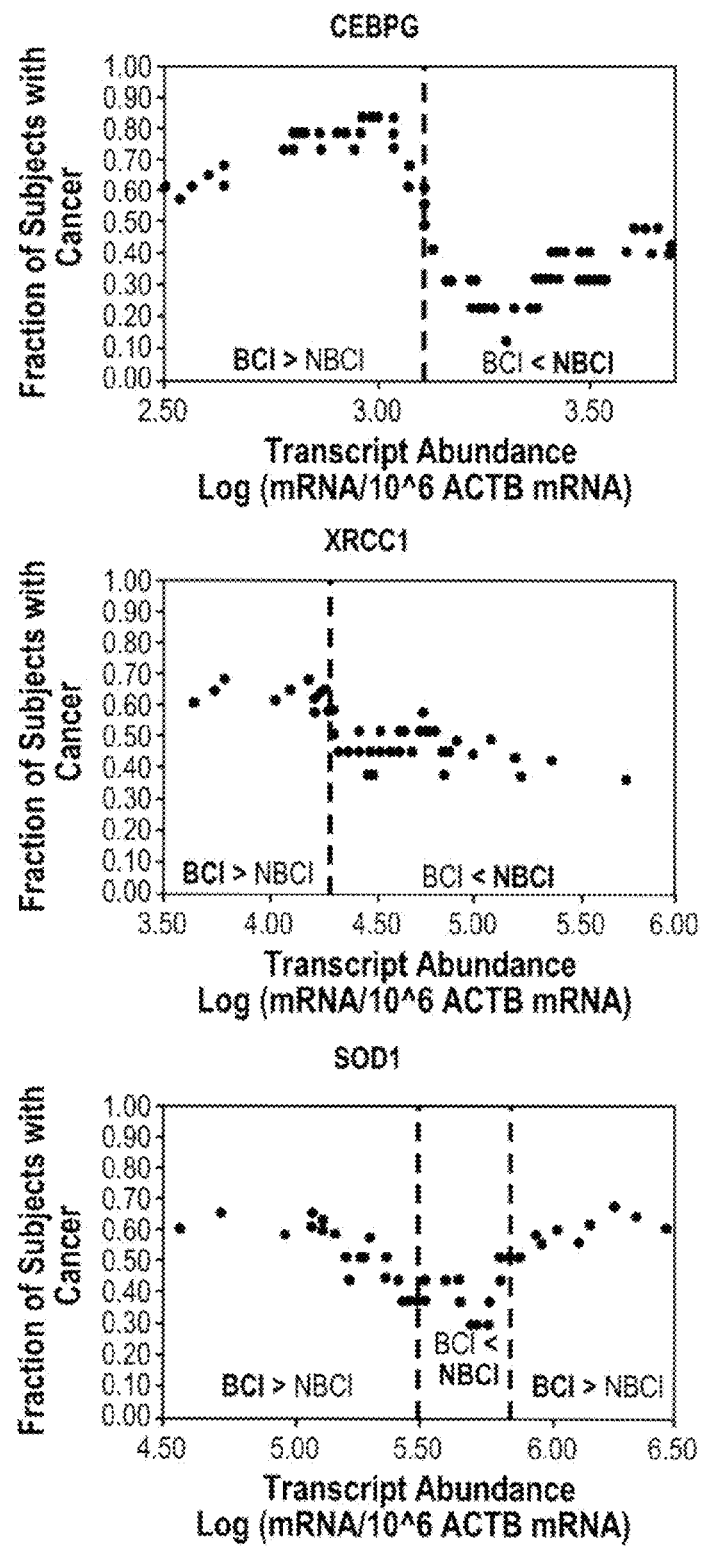
FIG. 10 (A-B) illustrates data from 49 individuals (25 bronchogenic carcinoma individuals [BCI] and 24 non-bronchogenic carcinoma individuals [NBCI]) were analyzed. For each gene, log transformed transcript abundance (TA) values for all 49 individuals were sorted in ascending order. Each sorted TA value represented a single individual with a diagnosis of bronchogenic carcinoma (BCI) or non-bronchogenic carcinoma (NBCI). TA values from BCI were assigned a binary value of one (1). TA values from NBCI were assigned a binary value of zero (0). For graphic presentation, a simple moving average of the binary indices was taken from 14 TA values nearest in value (7 higher and 7 lower). These values were plotted as "Fraction of Subjects with Cancer" (Y-axis) versus their corresponding Log Transcript Abundance values (X-axis). For each gene, a threshold level of TA that most accurately separated BCI from NBCI was determined empirically from receiver operating characteristic (ROC) curves.
Figure 10A:
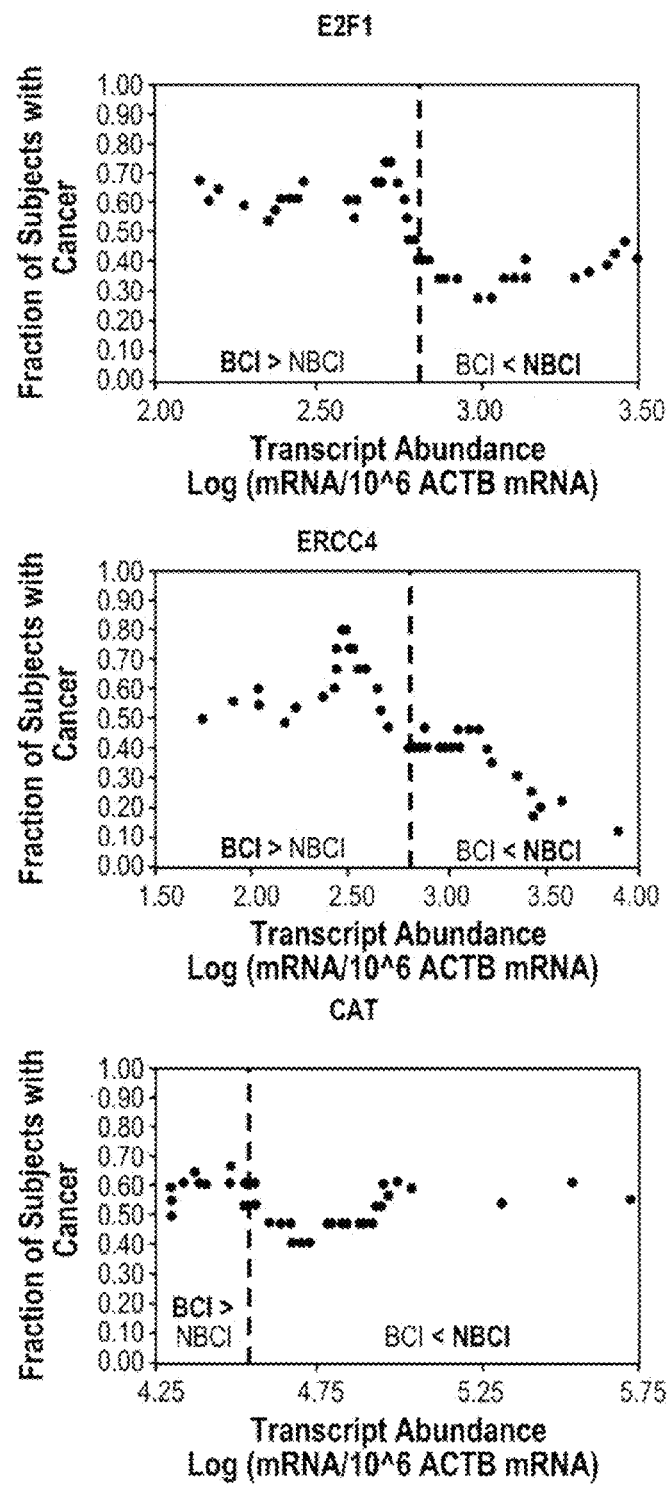
Figure 10A:
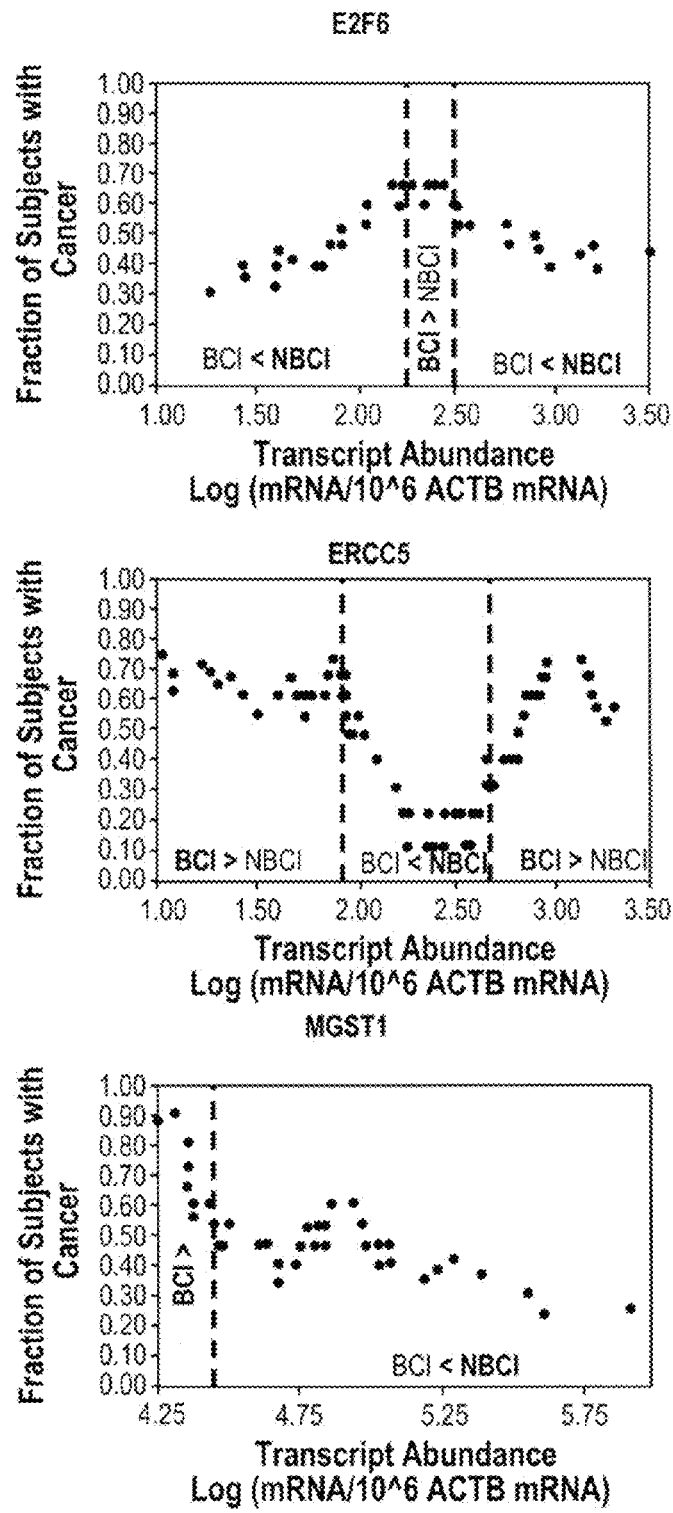
Figure 10B:
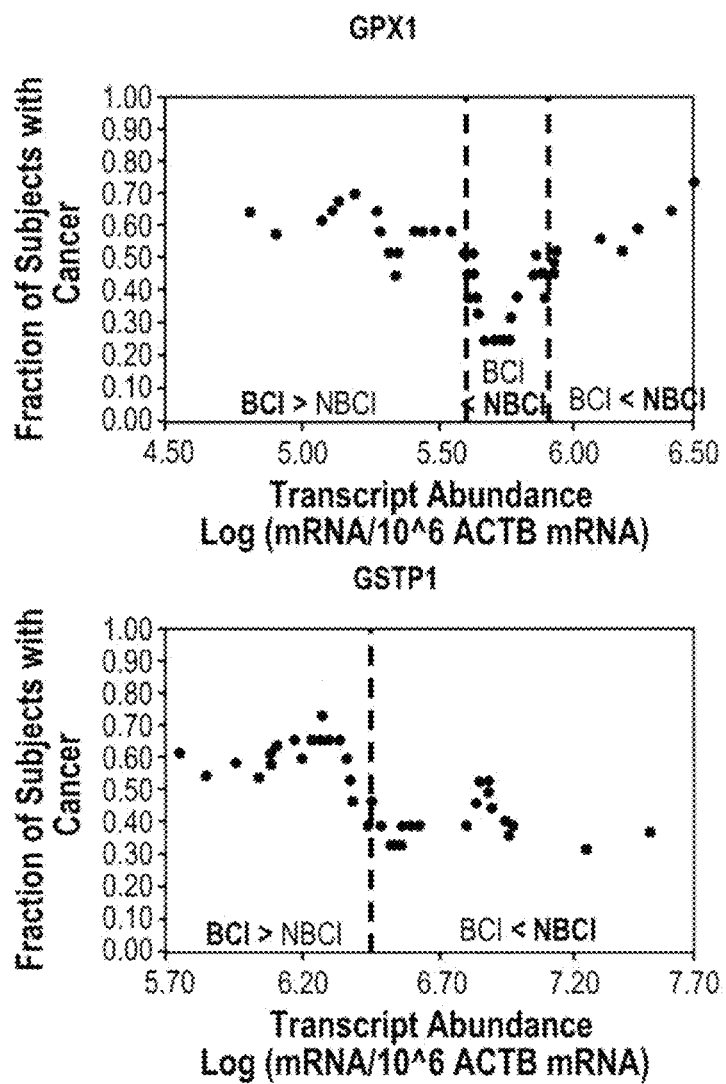
Figure 10B:
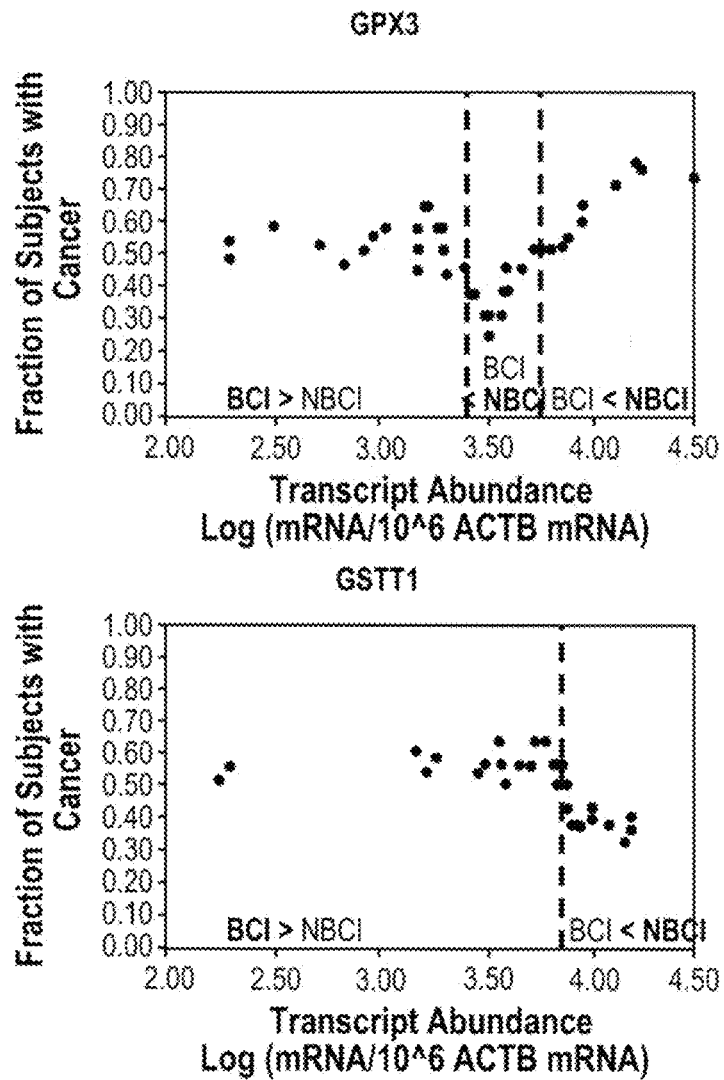
Figure 10B:
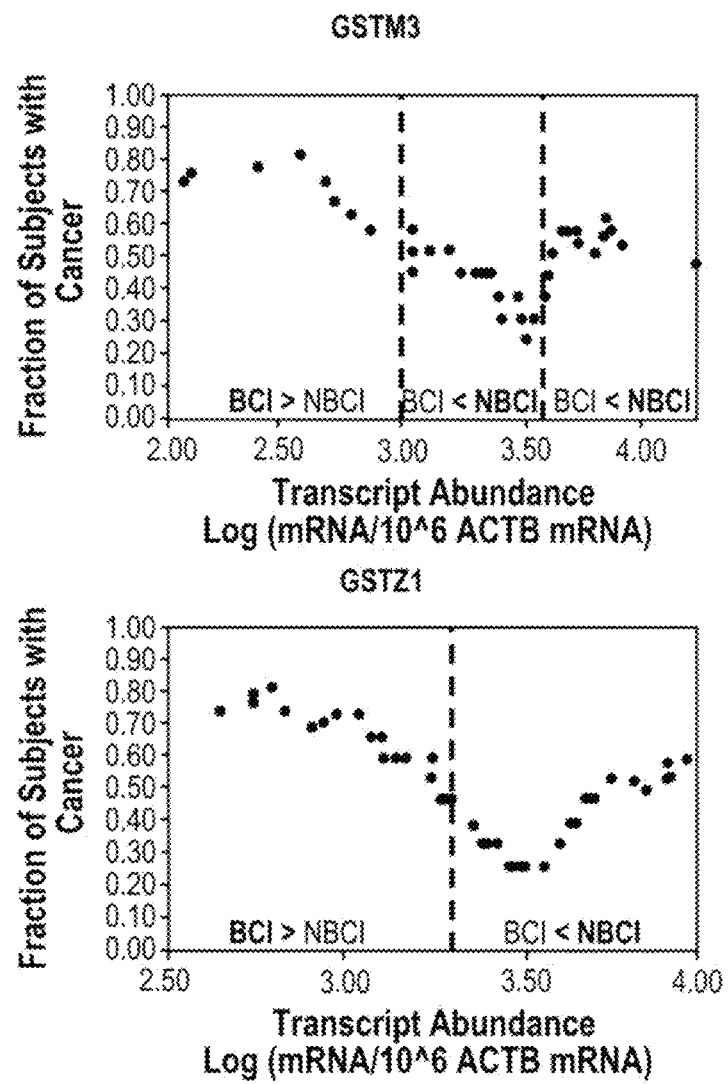
Figure 11:
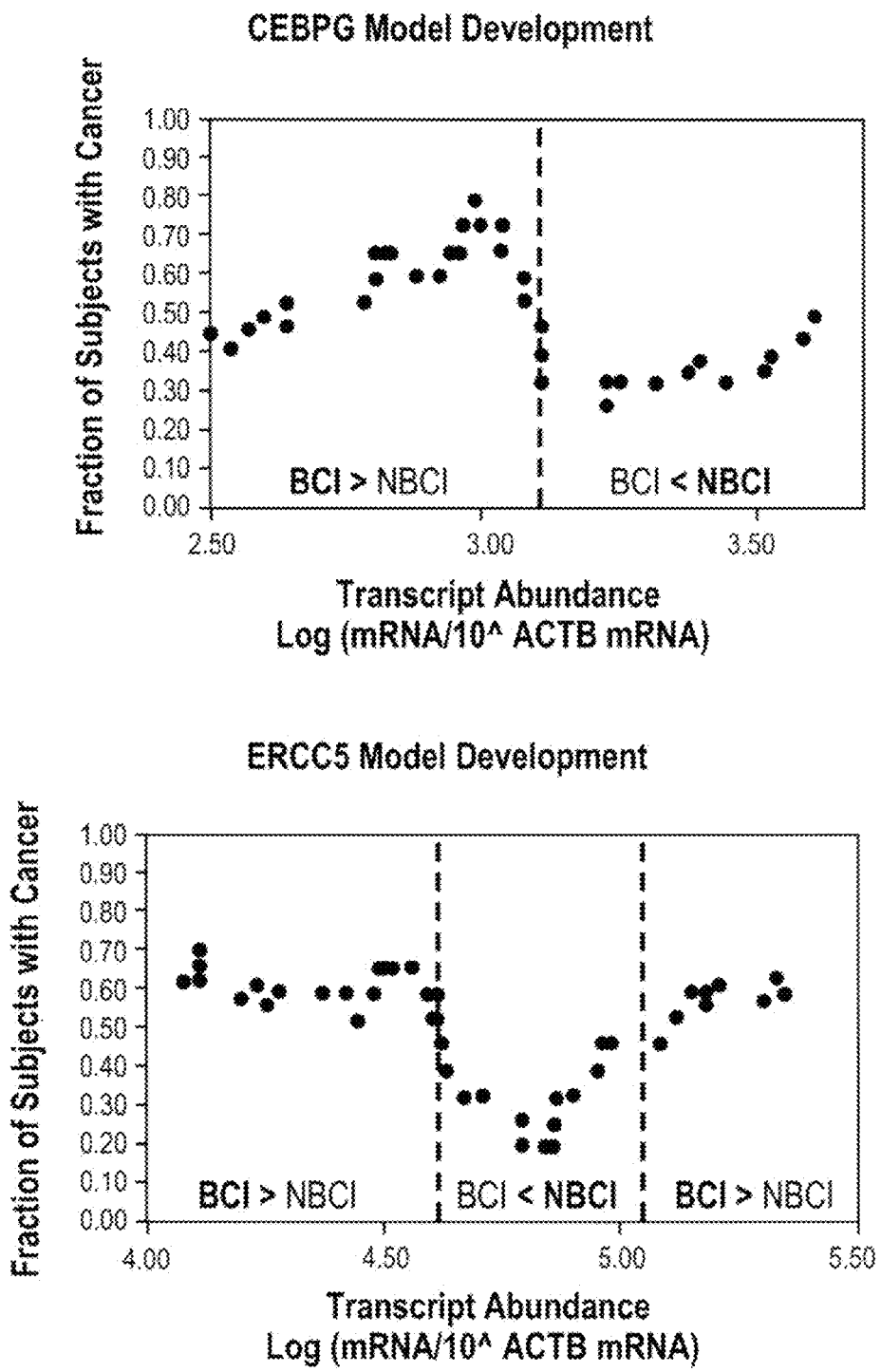
FIG. 11 illustrates CEBPG and ERCC5 (XPG) transcript abundance values from BCI and NBCI normal airway epithelial cell samples. Initial cutoff values distinguishing BCI from NBCI were derived from receiver operating characteristic (ROC) curves.
Figure 12:
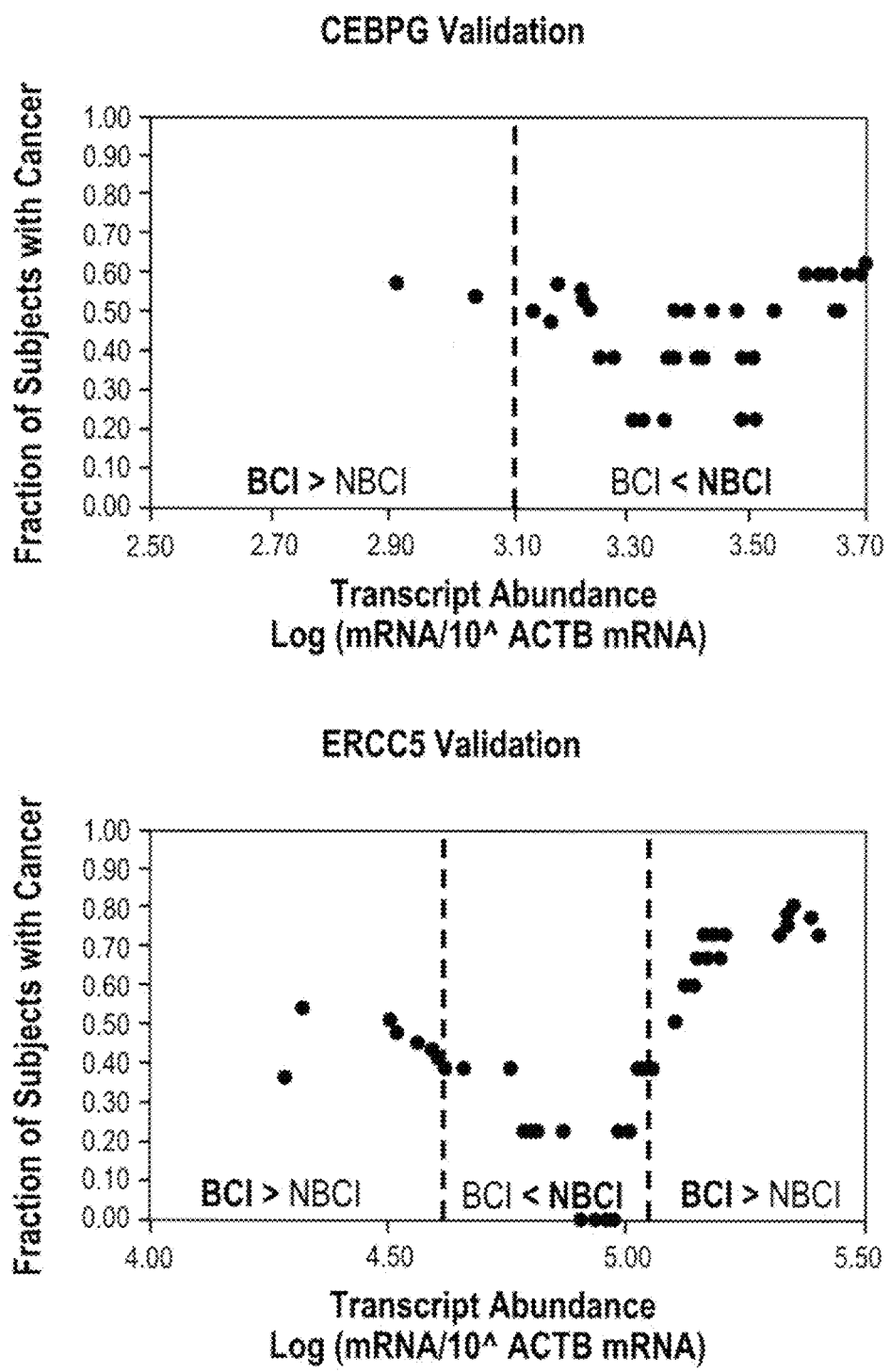
FIG. 12 illustrates validation studies on assessed samples. Studies included 10 additional Cancer (BCI) and 35 additional non-Cancer individuals (NBCI). For CEBPG, a predominance of transcript abundance values were observed above the Cancer cutoff. This is in agreement with the low prevalence of Cancer diagnoses in prior data-sets. A similar observation was also made for ERCC5 data.
Figure 13:
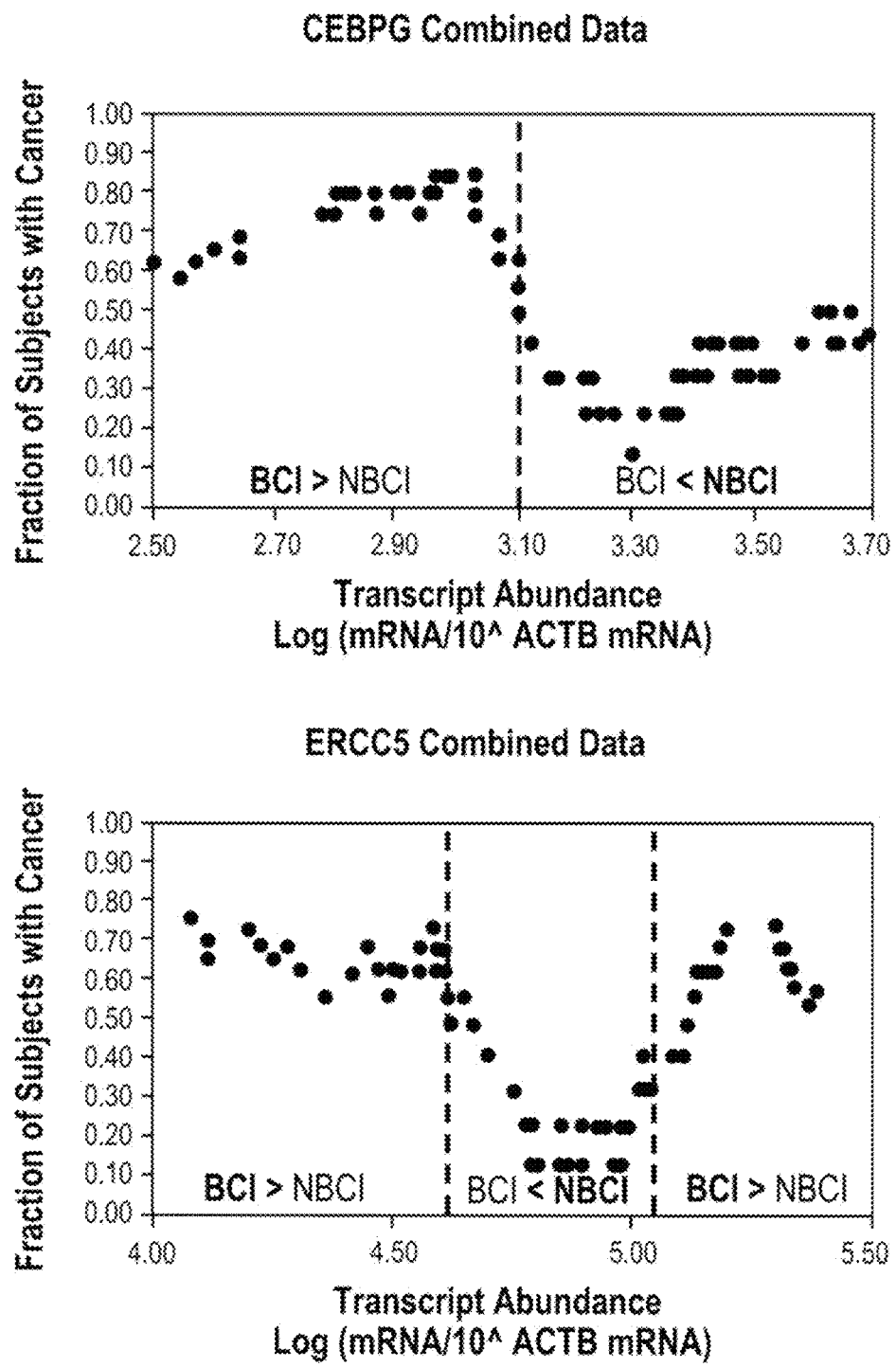
FIG. 13 illustrates analysis of ROC curves for the combined data-sets (35 Cancer and 65 non-Cancer individuals) for CEBPG and ERCC5. These results support the initial empirically determined Cancer/non-Cancer cutoff values.
Figure 14:
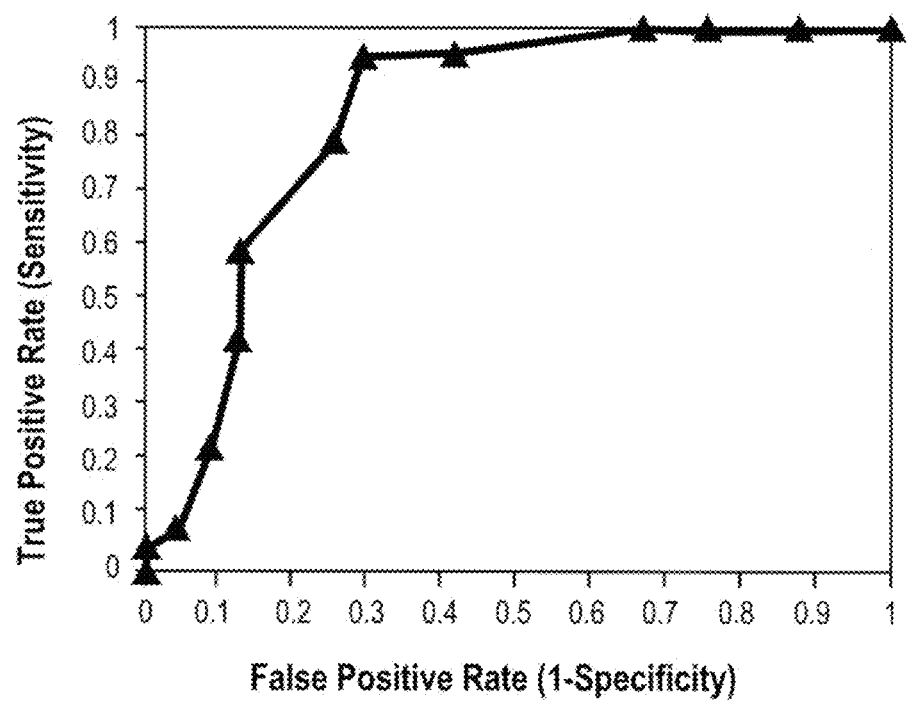
FIG. 14 illustrates Receiver Operating Characteristic (ROC) curve analysis of data in FIG. 7. Optimum sensitivity and specificity are achieved with 7 positive cancer risk values.

From this plot it is ascertained that any individual with a Log transcript abundance value for gene CEBPG<3.11 has a higher likelihood of being diagnosed with Lung Cancer; approximately 70-80% chance in comparison to 40% for those with a transcript abundance value of CEBPG>3.11 (FIG. 9).

In summary, for each gene, a threshold level of TA that most accurately separated lung cancer from non-lung cancer subjects was determined empirically. Depending on whether the TA level for a gene was above or below the threshold, the subject was assigned a value of 1 or 0. The values for each of the 15 genes were totaled for each subject. Using a total value cut-off of greater than or equal to 7 as a biomarker for lung cancer individuals, one false negative and seven false positives were observed among the 49 individuals assessed, yielding a sensitivity of 96% and specificity of 71% (e.g., FIG. 7). In some embodiments, a method of determining a biomarker using transcription abundance levels of CEBPG, E2F1, E2F6, XRCC1, ERCC4, ERCC5, GPX1, GPX3, GSTM3, GSTP1, GSTT1, GSTZ1, MGST1, SOD1 and CAT identifies if a subject is at higher risk for cancer by comparing the TA levels to threshold levels such as those in Table 13.

In some embodiments, subjects that are false positive, do not ostensibly have cancer/tumor lesions, or are cancer free, yet are at a greater risk for developing cancer.

Without being limited to a particular hypothesis and/or theory, there may be inter-individual variation in regulation of such key AO and DNAR genes by one or more TFs and individuals with sub-optimal regulation may be selected for development of BC if they are smokers. Inter-individual variation in risk for a disease that does not display a familial pattern, e.g., can be explained in that an individual must be heterozygous or homozygous for a risk bearing allele at a threshold number of genes from a group of genes that have redundant function in protecting cells from DNA damage. This may explain why only a fraction of smokers develop BC or other cancer-related and/or lung-related conditions. For example, genetic risk for BC may be inversely proportional to coordinate regulation of AO and DNAR genes in NBECs.

"Smokers" as used herein includes individuals who use or have used one or more products associated with conditions of the lung, including, e.g., tobacco products, such as cigarettes and/or chewing tobacco, as well as individuals who are or have been exposed to such products second-hand, such as being exposed to second-hand smoke. Smokers can include heavy smokers and light smokers or a range in between. For example, smokers include those who smoke 1 cigarette/day, 5 cigarettes/day, a pack of cigarettes/day or more. In some embodiments, individuals that are likely to have maximal difference in genetically determined risk can be compared. For example, case samples can be obtained from younger, light smokers or non-smokers who develop BC; while control samples can be obtained from older, heavy smokers without BC. Other factors considered can include individual airway anatomy, type of cigarette, inhalation technique, function of the cilia and mucosal cells in the bronchial epithelium, and intermittent chronic bronchitis exacerbations. Identified biomarkers can indicate BC, risk of BC, extent of BC (e.g., metastasizing or non-metastasizing) and/or prognosis (e.g., likelihood and/or degree of responsiveness to a particular chemotherapy).

In some embodiments, for example, the methods provided herein show that transcript abundance of CEBPG transcription factor is significantly (p<0.01) correlated with key anti-oxidant (AO) or DNA repair (DNAR) genes in NBEC of NBCI but not correlated in BCI. Further, for several key genes, this correlation is significantly lower in the NBEC of BCI. Details of these methods are provided in the Examples below. Briefly, TF recognition sites common to genes associated with BC (e.g., GSTP1, GPX1, CAT, GPX3, and SOD1) can be identified through sequence analysis, e.g., in silico DNA sequence analysis. Such sequence analysis using Genomatix Software (GmbH, Munich, Germany, http:// genomatix.de/cgi-bin/eldorado/; Quandt et al., 23:4878-4884 (1995)), for example, yields sites for 11 TFs, including EV11 and members of the C/EBP and E2F families.

Expression levels of the 11 identified TFs can be assayed in NBEC case samples from patients with BC and in control NBEC samples obtained from healthy individuals. For example, standardized RT-PCR reagents can be prepared and preferentially optimized for the TFs and other genes, e.g., as provided in Willey et al., in *Methods in Molecular Biology* (ed. Shimkets, R. A.) 13-41 (Humana Press, Inc., Totowa, N.J., 2004). TFs found to be expressed at low and/or invariant levels among multiple NBEC samples can be excluded from further analysis. Remaining TFs can be evaluated for correlation with an expanded group of AO and/or DNAR genes, including e.g., XRCC1, ERCC5, GSTP1, SOD1, GPX1, ERCC1, CAT, GSTZ1, and ERCC2.

As detailed in the Examples below, expression levels of XRCC1, ERCC5, GSTP1, SOD1 and GPX1 are significantly or nearly significantly correlated with expression levels of CEBPG in NBCI compared in BCI. Loss of correlation in BCI compared to NBCI can also be observed between expression levels of E2F1 with expression levels of ERCC5, GSTP1 and SOD1.

Other AO and/or DNAR genes can also be assayed. Examples of AO genes include those encoding enzymes (such as glutathione transferases (GSTs), e.g., GSTT1) and glutathione peroxidases (GSHPxs, e.g., GSHPxA)) that are capable of preventing or reducing injury from carcinogens. There are several classes of GSTs, including one microsomal class (mGST) and at least five cytosolic classes: GSTA, GSTM (e.g., GSTM1, GSTM3), GSTP (e.g., GSTP1), GSTT, and GSTZ. See also, Crawford et al., *Cancer Res* 60:1609-1618 (2000); Hackett et al., *American Journal of Respiratory Cell and Molecular Biology* 29:331-343 (2003); and Willey et al., *ILSI Press, Washington, D.C., U. Heinrich and U. Mohr* (Eds), pp. 79-96 (2000).

Examples of DNAR genes include those encoding enzymes that can recognize and/or repair specific nucleotide alterations, base mispairs, and double-strand breaks. DNAR pathways that have been identified in mammalian cells and which play major roles in protection against mutation are: 1) DNA mismatch repair (MMR), 2) nucleotide excision repair (NER), 3) base excision repair (BER), 4) damage reversal by 06-methylguanine DNA methyltransferase (MGMT), 5) homologous recombination (HR), and 6) non-homologous end joining (NHEJ).

Without being limited to a given theory and/or hypothesis, it appears that smokers are selected to develop BC at least in part due to sub-optimal AO and/or DNAR gene regulation by CEBPG. That is, in NBCI, CEBPG may regulate transcription of key AO and/or DNAR genes in NBEC and in smokers who develop BC, CEBPG regulation may be sub-optimal for a sufficient number of AO and/or DNAR genes to cause increased risk. For example, one possible explanation for loss of correlation in BCI is alteration in the function of one or more TFs responsible for correlation in NBCI. In preferred embodiments, methods provided herein may improve understanding of risk for lung cancer and enable early screening and chemoprevention for those at the highest risk.

One of skill in the art will recognize that the methods provided herein can be applied to the identification of biomarkers for other cancer-related conditions. Examples of other cancer-related conditions include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multi forma, leukemias, lymphomas, malignant melanomas, epidermoid carcinomas, and other carcinomas and sarcomas.

In some embodiments, case and control samples may be obtained from different stages of cancer. Cells in different stages of cancer, for example, include non-cancerous cells vs. non-metastasizing cancerous cells vs. metastasizing cells from a given patient at various times over the disease course. Cancer cells of various types of cancer may be used, including, but not limited to, for example, a bladder cancer, a bone cancer, a brain tumor, a breast cancer, a colon cancer, an endocrine system cancer, a gastrointestinal cancer, a gynecological cancer, a head and neck cancer, a leukemia, a lung cancer, a lymphoma, a metastases, a myeloma, neoplastic tissue, a pediatric cancer, a penile cancer, a prostate cancer, a sarcoma, a skin cancer, a testicular cancer, a thyroid cancer, and a urinary tract cancer. In preferred embodiments, biomarkers can be developed to predict which chemotherapeutic agent can work best for a given type of cancer, e.g., in a particular patient.

In some embodiments, the methods for identifying biomarkers for BC can be applied to identifying biomarkers for these other cancer-related conditions. For example, TF recognition sites common to genes associated with one of these other cancer-related conditions can be identified through sequence analysis. Examples of genes associated with cancer-related conditions include, but are not limited to, antioxidant (AO) genes, xenobiotic metabolism enzyme genes (XME) and DNA repair (DNAR) genes. Examples of XME genes include those expressed in human NBEC that metabolize carcinogens and/or pro-carcinogens present in cigarette smoke, such as, but not limited to, cytochromes p450 (CYP) 1A1, 1B1, and 2B6, which metabolize polycyclic aromatic hydrocarbon procarcinogens in cigarette smoke; epoxide hydrolase, NAPDH oxidoreductase and phenolosulfotransferases, which also metabolize polycyclic aromatic hydrocarbons; and CYP2A6/7 and CYP2E1, which metabolize nitroso compounds, such as nitrosamines. See, e.g., Willey et al., *Am J Respir Cell Mol Biol* 17(1):114-124 (1997); and Willey et al., *Am J Respir Cell Mol Biol* 14(3):262-271 (1996).

Expression levels of the identified TFs can be assayed in case samples from patients with the cancer-related condition and in control samples obtained from healthy individuals or obtained from different stages of cancer. In preferred embodiments, standardized RT-PCR reagents can be prepared and preferentially optimized for the TFs and other genes, e.g., as provided in Willey et al., in *Methods in Molecular Biology* (ed. Shimkets, R. A.) 13-41 (Humana Press, Inc., Totowa, N.J., 2004). TFs found to be expressed at low and/or invariant levels among multiple control samples can be excluded from further analysis. Remaining TFs can be evaluated for correlation with an expanded group of genes known to be associated with the cancer-related condition. Additional details are provided in the Examples below.

Biomarkers for Chronic Obstructive Pulmonary Disease and Other Lung-Related Conditions In another particular embodiment, transcription factor biomarkers can be identified for COPD. COPD includes, e.g., emphysema (including both heterogeneous emphysema and homogenous emphysema), asthma, bronchiectais, and chronic bronchitis. Genes associated with COPD also include AO and DNAR genes. Without being limited to a particular hypothesis and/or theory, there may be inter-individual variation in regulation of key AO and DNAR genes by one or more TFs and individuals with sub-optimal regulation may be selected for development of COPD, especially if they are smokers. Identified biomarkers can indicate COPD, risk of COPD, extent of COPD (e.g., metastasizing or non-metastasizing) and/or prognosis (e.g., likelihood and/or degree of responsiveness to a particular therapy).

In some embodiments, for example, the methods provided herein may show that transcript abundance of CEBPG transcription factor is significantly (p<0.01) correlated with key antioxidant (AO) or DNA repair (DNAR) genes in control samples obtained from healthy individuals but not correlated in case samples obtained from COPD patients. Without being limited to a given theory and/or hypothesis, smokers may be selected to develop COPD on the basis of sub-optimal AO and/or DNAR gene regulation by the transcription factor CEBPG.

In some embodiments, e.g., TF recognition sites common to genes associated with a COPD (e.g., GSTP1, GPX1, CAT, GPX3, and SOD1), can be identified through sequence analysis, e.g., using Genomatix Software GmbH, Munich, Germany, http://genomatix.de/cgi-bin/eldorado/) (Quandt et al., *NAR*, 23, 4878-4884 (1995)). Expression levels of identified TFs can be assayed in NBEC case samples from patients with COPD and in NBEC control samples obtained from healthy individuals. For example, standardized RT-PCR reagents can be prepared and preferentially optimized for the TFs and other genes, e.g., as provided in Willey et al., in *Methods in Molecular Biology* (ed. Shimkets, R. A.) 13-41 (Humana Press, Inc., Totowa, N.J., 2004). TFs found to be expressed at low and/or invariant levels among multiple control samples can be excluded from further analysis. Remaining TFs can be evaluated for correlation with an expanded group of AO and/or DNAR genes, including e.g., XRCC1, ERCC5, GSTP1, SOD1 or GPX1. Similar findings may be obtained for the transcription factor E2F1.

One of skill in the art will recognize that the methods provided herein can be applied to the identification of biomarkers for other lung-related conditions. Examples of lung-related conditions include, but are not limited to, sarcoidosis, pulmonary fibrosis, pneumothorax, fistulae, bronchopleural fistulae, cystic fibrosis, inflammatory states, and/or other respiratory disorders. Lung-related conditions can also include smoking-related and/or age-related changes to the lung, as well as lung damage caused by a traumatic event, infectious agents (e.g., bacterial, viral, fungal, tuberculin and/or viral agents), exposure to toxins (e.g., chemotherapeutic agents, environmental pollutants, exhaust fumes, and/or insecticides), and/or genetic factors (e.g., alpha-1 antitrypsin deficiency and other types of genetic disorders which involve elastic and/or connective tissues degradation and/or impaired synthesis of elastic and/or connective tissues and/or impaired repair of elastic and/or connective tissues of the lungs).

TF recognition sites common to genes associated with one of these other lung-related conditions can be identified through sequence analysis. Expression levels of the identified TFs can be assayed in case samples from patients with the lung-related condition and in control samples obtained from healthy individuals or obtained from different stages of the lung-related condition. In preferred embodiments, standardized RT-PCR reagents can be prepared and preferentially optimized for the TFs and other genes, e.g., as provided in Willey et al., in *Methods in Molecular Biology* (ed. Shimkets, R. A.) 13-41 (Humana Press, Inc., Totowa, N.J., 2004). TFs found to be expressed at low and/or invariant levels among multiple control samples can be excluded from further analysis. Remaining TFs can be evaluated for correlation with an expanded group of genes known to be associated with the lung-related condition.

B. Identification of Polymorphisms

In another aspect, the present disclosure relates to methods for identifying polymorphisms that indicate a biological state. In some embodiments, the method involves identifying a nucleotide variation between case samples and control samples in a transcription factor or other gene, where the transcription factor and/or the other gene are identified using methods provided herein. Some embodiments, for example, can comprise obtaining a plurality of control samples wherein expression levels of a transcription factor are correlated with expression levels of another gene; obtaining a plurality of case samples wherein expression levels of the transcription factor are not correlated with expression levels of the gene; and identifying a nucleotide variation in the transcription factor and/or in the gene in one or more of said case samples compared with one or more of said control samples.

For example, some embodiments provide a method for identifying DNA sequence variation associated with disease and/or risk for disease involving a) determining expression levels of genes involved in i) conferring the phenotype or ii) regulating transcription of the genes involved in conferring the phenotype, b) identifying a transcription factor responsible for regulating the relevant genes for which expression levels are correlated with regulated gene expression levels in low risk and/or non-diseased individuals/tissues, but is not correlated with normally-regulated genes in at risk individuals and/or diseased individuals/tissues, and c) identifying one or more DNA sequence variations responsible for determining regulation of the involved genes.

"Polymorphism" or "DNA sequence variation" as used herein can refer to any one of a number of alternative forms of a given locus (position) on a chromosome. The alternative form may involve a single base pair difference, such as a single nucleotide polymorphism (SNP). In some embodiments, the polymorphism may involve more than one base pair change, e.g., it may involve at least about 2, at least about 3, or least about 10 nucleotide differences. In some embodiments, the polymorphism may involve less than about 50, less than about 100, less than about 200, or less than about 500 nucleotide differences. The term polymorphism may also be used to indicate a particular combination of alleles, e.g., two or more SNPs, in a given gene or chromosomal segment. In some embodiments, for example, identification of more than one nucleotide variation identifies a biological state, e.g., a specific combination of alleles at particular genes may indicate risk for a disease condition.

Identifying the nucleotide variation can be achieved by any methods known in the art, e.g., using various methods for determining sequence information of nucleic acids. Examples include the dideoxy termination method of Sanger (see, e.g., Sanger et al., *Proc. Natl. Acad. Sci. U.S.A.* 74: 563-5467 (1977)); the Maxam-Gilbert chemical degradation method (see, e.g., Maxam and Gilbert, *Proc. Natl. Acad. Sci. U.S.A.* 74: 560-564 (1977)); Sanger-extension method using dyes associated with terminal nucleotides, gel electrophoresis and automated fluorescent detection; techniques using mass spectroscopy instead of electrophoresis; pyrophosphate release techniques (see, e.g., Ronaghi et al., *Science* 281: 363-365 (1998) and Hyman, *Anal. Biochem.* 174: 423-436 (1988)); single molecule sequencing techniques utilizing exonucleases to sequentially release individual fluorescently labeled bases (see, e.g., Goodwin et al., *Nucleos. Nucleot.* 16: 543-550 (1997)); techniques pulling DNA through a thin liquid film as it is digested in order to spatially separate the cleaved nucleotides (see, e.g., Dapprich et al., *Bioimaging* 6: 25-32 (1998)); techniques determining the spatial sequence of fixed and stretched DNA molecules by scanned atomic probe microscopy (see, e.g., Hansma et al., *Science* 256: 1180-1184 (1992)); techniques described in U.S. Pat. No. 5,302,509 to Cheeseman and in U.S. 2003/0044781 (Korlach); and techniques using hybridization of (substantially) complementary probes as described, e.g., in U.S. Pat. Publication Nos. 2005/0142577 and 2005/0042654. Identified polymorphisms can comprise certain alleles that are represented at higher or significantly higher rates in a disease condition, e.g., as described in more detail below.

In some embodiments, the pattern of expression levels of a transcription factor and its normally-regulated gene allows focus on a particular region of the transcription factor and/or gene, in order to identify polymorphisms indicative of the biological state. For example, in some embodiments, methods further comprise obtaining a first relation comparing expression levels of the gene to expression levels of the transcription factor in control samples; obtaining a second relation comparing an expression level of the gene to an expression level of the transcription factor in one of the case samples; comparing first and second relations; and analyzing a region of said transcription factor and/or said gene based on the comparison in order to identify said nucleotide variation.

"Region" as used herein can refer to a nucleic acid sequence that preferably involves fewer base pairs than the entire gene. A region can include coding and non-coding, transcribed and non-transcribed, and/or translated and untranslated regions. For example, a region of a gene can include the regulatory elements 5' of the coding region, e.g., recognition sites for TF. A region of a TF can include 5' regulatory regions, 3' UTR and/or coding regions of the TF. Methods provided herein teach specific regions to focus on in identification of polymorphisms indicative of a biological state. In some embodiments, the region spans at least about 5, at least about 10, at least about 20, at least about 30, at least about 50, at least about 80, or at least about 100 bases. In some embodiments, the region spans less than about 150, less than about 200, less than about 250, less than about 300, or less than about 500 bases.

First and second relations can refer to any mathematical, graphical, statistical relationship between values. In some embodiments, for example, expression levels of the transcription factor can be plotted against expression levels of the other gene, where the expression levels are assayed in control samples. The control sample values can be used to obtain a regression line as the first relation. The second relation can comprise a coordinate point, e.g., plotted with the regression line, of transcription factor expression level versus the expression level of the other gene, where the expression levels are assayed in a given case sample. In such embodiments, first and second relations can be compared in terms of whether the case sample coordinate point falls on, above, or below the regression line.

In some embodiments, where the coordinate point falls above the regression line, focus is directed to the 5' regulatory region and/or 3' UTR of the transcription factor. In some embodiments, where the coordinate point falls below the regression line, focus is directed to the coding region of the transcription factor and/or recognition sites for the transcription factors in other genes. The coordinate point may fall above, on, or below the line for different individuals, and where the coordinate falls indicates the region(s) to focus on when analyzing nucleic acids from those individuals. The frequency of polymorphisms in case samples can be determined and compared to frequency in controls. Additional explanation, discussion and details are provided in the Examples below, specifically in relation to NBCI and BCI.

Polymorphisms for Bronchogenic Carcinoma and Other Cancer-Related Conditions

In some embodiments, polymorphisms that indicate BC can be identified using the methods provided herein. For example, the nucleotide sequences of CEBPG and E2F1 transcription factors can be analyzed to determine variation between case and control samples. The 5' regulatory region, 3' UTR and/or coding regions of the TFs can be analyzed. In some embodiments, the nucleotide sequences of XRCC1, ERCC5, GSTP1, SOD1 or GPX1 can be analyzed to determine variation between case and control samples. Preferably, TF recognition sites common to such genes are analyzed, e.g., the 1100 bp regulatory region (1000 upstream and 100 bp downstream of the transcription start site) of XRCC1. The frequency of each allele at each SNP in NCBI can be determined and compared to frequency of each allele at each SNP in BCI. Those of skill in the art will recognize that the methods provided herein can be applied to the identification of polymorphisms for other cancer-related conditions.

Structural knowledge of transcription factor biomarkers can aid in identifying biomarker polymorphisms. For example, it is known that CEBPG is a truncated CEBP TF (*Johnson and Williams in Liver Gene Expression* (eds Yaniv M and Tronche F) 231-258 (R. G. Landes Company, 1994). CEBPG possesses sequences necessary for DNA binding and heterodimer formation, but lacks sequences necessary for transactivation (Cooper et al., *NAR,* 23, 4371-4377 (1995)). CEBPG can form heterodimers with other CEBP family members, e.g., leading to increased (Hongwei et al., *JBC,* 277:38827-38837 (2002)) or decreased (Cooper et al., *NAR,* 23:4371-4377 (1995)) transcription of regulated genes.

In preferred embodiments, DNA regions analyzed to provide polymorphisms include regions affecting transcription regulation, protein function, post-transcriptional processing, and/or protein-protein binding, including those in the 5' regulatory region, those in the 3' UTR, translated region, and 5' UTR of the coding region. For example, sequences for DNA binding and heterodimer formation can be analyzed for polymorphisms indicative of BC. Specifically, the collinear string of 50 bp in the bZip region of CEBPG can also be analyzed for polymorphisms indicative of BC. Further, regions known to be associated with risk can be evaluated for polymorphism. See, e.g., regions described in Ratnasinghe et al., *Anticancer Res.* 23:627-32 (2003); Wang, *DNA Repair (Amst).* 2(8):901-8 (2003); and Misra et al., *Cancer Lett.* 191:171-8 (2003). Additional details are provided in the Examples below.

Identification of polymorphisms that affect regulation of XRCC1, ERCC5, GSTP1, SOD1, and GPX1 by CEBPG can also yield biomarkers. A biomarker combining polymorphisms that affect regulation with those that affect function of AO and DNAR genes is preferred in some embodiments for identifying individuals at risk for BC. For example, a biomarker associated with functional alteration in regulation of risk secondary to one or more variations in DNA sequence enables focus on genes that contribute to risk. This can enable marked reduction in the number of individuals that would have to be included in epidemiologic studies As discussed above, the relation of expression levels of TG and TF from a particular BCI can indicate regions to be analyzed for polymorphisms in that particular BCI. As detailed in the Examples below, the 5' regulatory region, coding region and/or 3' UTR of CEBPG are analyzed specifically, as well as CEBPG recognition sites for target genes, such as XRCC1, ERCC5, SOD1, GSTP1 and/or GPX1.

Polymorphisms for COPD and Other Lung-Related Conditions

In some embodiments, polymorphisms that indicate COPD can be identified using the methods provided herein. For example, similar regions of TF, AO and/or DNAR genes can be analyzed, as described with respect to BC. Without being limited to a given theory and/or hypothesis, there is a strong correlation between risk for emphysema and risk for BC, and risk for emphysema is also associated with antioxidant capacity in humans (Repine et al., *Am. J. Respir. Crit. Care Med.*, 156, 341-357 (1997)). Also, CEBPG−/− knockout mice begin to die within 24 hours of birth, showing emphysematous lungs on histological examination (Kaisho et al., *J. Exp. Med.*, 190, 1573-1581 (1999)).

For example, in some embodiments, the nucleotide sequences of CEBPG and E2F1 transcription factors can be analyzed to determine variation between case samples from COPD patients and control samples. Preferably, the 5' regulatory, coding, and 3' un-translated regions of the TFs are analyzed. In some embodiments, the nucleotide sequences of XRCC1, ERCC5, GSTP1, SOD1 or GPX1 can be analyzed to determine variation between case samples from COPD patients and control samples. Preferably, TF recognition sites common to such genes are analyzed, more preferably CEBPG recognition sites of XRCC1, ERCC5, GSTP1, SOD1 and/or GPX1. As detailed above, in preferred embodiments, DNA regions analyzed to provide polymorphisms include regions affecting transcription regulation, protein function, post-transcriptional processing, and/or protein-protein binding, including those in the upstream regulatory region, and those in the 3' UTR, translated region, and 5' UTR of the coding region. Those of skill in the art will recognize that the methods provided herein also can be applied to the identification of biomarkers for other lung-related conditions.

Some embodiments also provide probes consisting of relevant nucleic acid sequences for identifying polymorphisms indicative of COPD. Examples of four such probes include (i) a probe comprising a nucleic acid sequence consisting of a 5' regulatory region of CEBPG±about 100 bases; (ii) a probe comprising a nucleic acid sequence consisting of a 3' untranslated region of CEBPG±about 100 bases (iii) a probe comprising a nucleic acid sequence consisting of a bZip region of CEBPG±about 100 bases; and (iv) a probe comprising a nucleic acid sequence consisting of a CEBPG recognition site±about 100 bases. Such probes can be anchored to a support, e.g., in an array, and/or provided in kits for use in identifying COPD or risk thereof, as well as other lung-related conditions in some embodiments.

II. Methods and Compositions for Diagnosis
A. Lack of Correlation Approach

In another aspect, the disclosure relates to methods and compositions for diagnosing a biological state by identifying loss of correlation between two or more biomarkers compared to controls. In some embodiments, the method involves identifying lack of correlation between expression levels of a transcription factor and another gene. Generally, the other gene is a gene associated with the biological state and/or a gene that is regulated by the transcription factor in controls.

Figure 2:
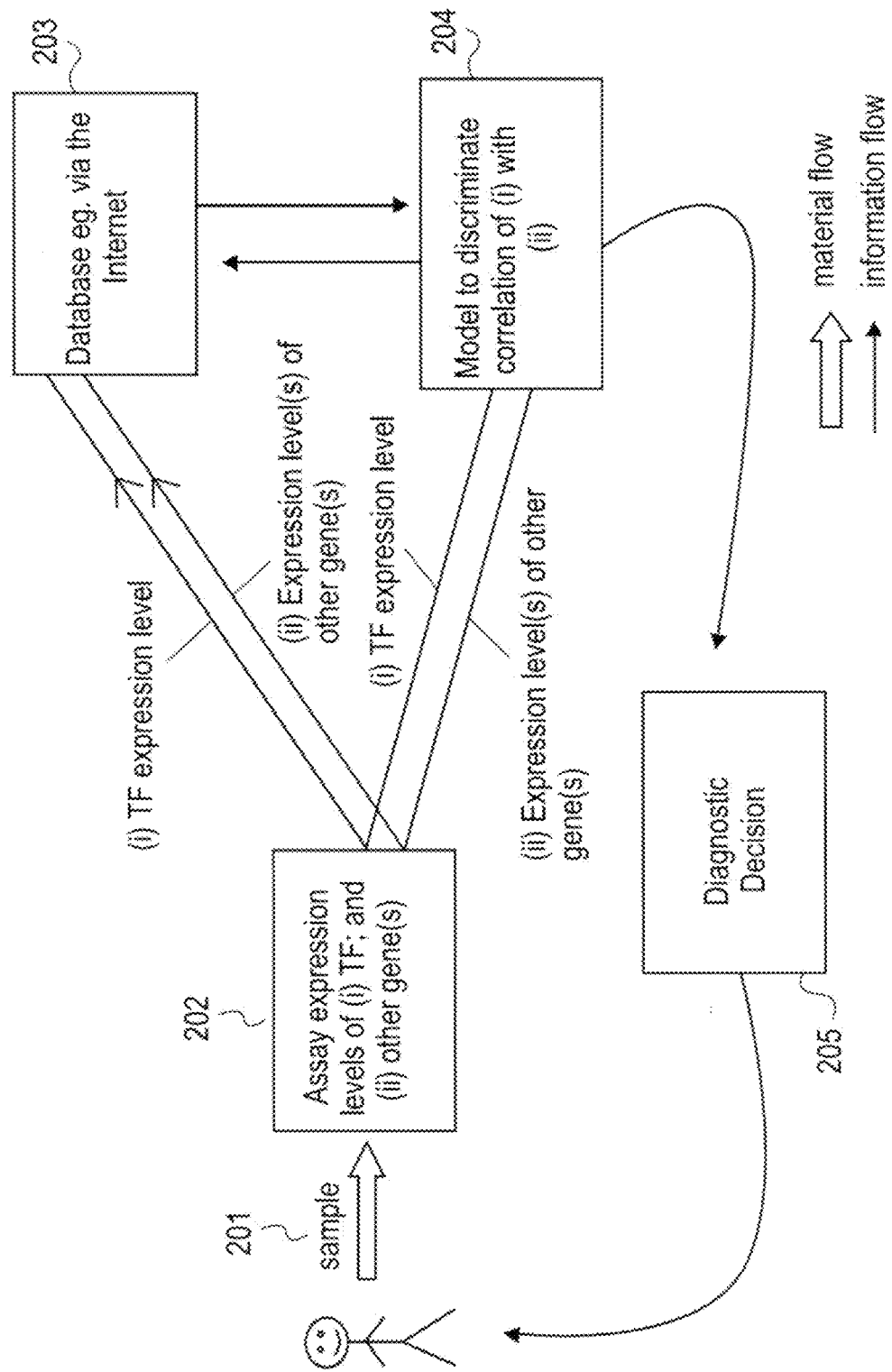
FIG. 2 illustrates the overall process for diagnosing a biological state.

FIG. 2 illustrates the overall process for diagnosing a biological state in some embodiments disclosed herein. At step 201, a sample is collected from a subject, e.g. a patient. The sample may comprise, e.g., any tissue or biological fluid as provided in detail above. The type of sample collected may depend, e.g., on the biological state sought to be identified. For example, NBEC samples may be obtained to test for BC and/or COPD, described in more detail below. In preferred embodiments, the sample is a readily-accessible sample, e.g., one that can be obtained with a non-invasive or mildly-invasive technique. Such samples include, e.g., urine samples, bloods samples, semen samples, or more preferably saliva samples, buccal and/or nasal epithelial cell samples.

At step 202, expression levels of (i) a transcription factor and (ii) at least one other gene are assayed using the sample obtained from the subject. Any methods for assaying expression levels may be used, e.g., as described above. In preferred embodiments, the expression levels are measured using standardized mixtures of reagents that comprise known amounts of internal standards as described, e.g., in U.S. patent application Ser. Nos. 11/072,700 and 11/103,397.

At step 203, expression level values are entered into a database. In some embodiments, the database can be accessed over the Internet. In some embodiments, demographic information regarding the subject can be recorded along with the results of gene expression measurements on the collected samples. Preferably, such data is stored in a separate database from the identifying information. For example, the identifying information can be separated from the sample and demographic information as soon as the sample is brought into the laboratory. In preferred embodiments, the database allows for collection of values for various expression measurements, e.g., measurements obtained from different patients, the same or different patients over time (e.g., over the course of a disease and/or over the course of a treatment regime). In preferred embodiments, these data are directly comparable within certain CV limits, e.g., as taught in U.S. Provisional Application Ser. No. 60/646,157. In some embodiments, such a database can be used with gene expression data in clinical diagnostic testing, e.g., as described below.

At step 204, the expression levels are mathematically computed using a model that discriminates whether or not the expression levels are correlated with each other. As FIG. 2 illustrates, in some embodiments, assayed expression levels for (i) the transcription factor and (ii) the other gene(s) are entered into a database 203 and data from the database is used in the model. In some embodiments, assayed expression levels for (i) the transcription factor and (ii) the other gene(s) are used directly in the model. The model allows discrimination of whether or not (i) is correlated with (ii). Lack of correlation in the sample obtained from the subject can indicate the biological state. In still some embodiments, newly identified biomarkers themselves can be used to identify the biological state, e.g., as discussed in more detail below.

A model that discriminates whether or not expression levels are correlated with each other can be obtained by any means, e.g., using techniques of biostatistics and/or bioinformatics. For example, in some embodiments, the model was obtained by assaying in a plurality of case samples expression levels of the transcription factor and of the other gene; assaying in a plurality of control samples expression levels of the transcription factor and of the other gene; and using the expression levels to compute the model.

In some embodiments, the model is computed using at least one technique selected from bivariate analysis, mutivariate analysis, genetic programming software analysis, logarithmic transformation, Pearson's correlation, Bonferroni adjustment, Fisher's Z-transformation test, t-test, two-sided test, ANOVA, and Duncan's test. Models can be derived using a training set of subjects, assessed using expression levels obtained from additional sets of subjects, and suitable models can be refined through analysis of additional genes in the training sets and validation in additional sets. Additional details are provided in the Examples below.

In some embodiments, the model comprises a relation between expression levels of the transcription factor and other gene, e.g., as described below for diagnosing BC. In some embodiments, the relation is a ratio, e.g., a gradient of a regression line plotting expression levels of a transcription factor against expression levels of a target gene for controls, e.g., TF/TG or TG/TF. In some embodiments, where expression levels obtained from a sample coincide with the ratio (e.g., fall along the regression line), correlation is indicated; where expression levels obtained from a sample do not coincide with the ratio (e.g., being significantly above or below the regression line), lack of correlation is indicted. In preferred embodiments, the TG/TF ratio for each of a plurality of TGs does not coincide with a regression line ratio. For example, the TG/TF ratio does not coincide for at least about 2, at least about 3, at least about 5, at least about 10, at least about 20, at least about 50, at least about 80, or at least about 100 TGs. In some embodiments, the TG/TF ratio does not coincide with a regression line ratio for less than about 150, less than about 200, less than about 300, or less than about 500 TGs. Additional details are provided in the Examples below.

In preferred embodiments, a high-speed computer program can be used to cause multiple expression level values to interact in a random manner, e.g., according to a multiplicity of linear and non-linear functions. This can (a) enable rapid determination of mathematical rules that best fit the data; and (b) provide information regarding the likely scaling of expression levels to experimentally-observed function for various genes (i.e. based on whether predominantly linear or non-linear mathematical functions relate expression levels for a particular gene to that of other genes). Software that can be used for this purpose include, but are not limited to, e.g., Genetics2, Ann Arbor, Mich.

At step 205, a diagnosis decision can be made, e.g., based on whether or not (i) and (ii) are correlated, and/or on the level of a biomarker identified. The diagnostic decision may comprise identification of a disease condition, the stage or extent of progression of the condition, and/or the likeliness of response to various treatments. As FIG. 2 illustrates, the information regarding diagnosis can be communicated to the subject, e.g., a patient in a clinical setting.

Diagnosis of Cancer-Related Conditions and/or Lung-Related Conditions

In some embodiments, the invention provides methods and compositions for diagnosing a cancer-related condition, e.g., BC, and/or a lung-related condition, e.g., COPD. For example, BC can be diagnosed by identifying lack of correlation (compared to controls) between a transcription factor and a gene associated with BC. For example, some embodiments comprise assaying an expression level of CEBPG and/or E2F1 in a sample obtained from a subject; assaying an expression level of at least one other gene in the sample, where the other gene is associated with BC; and mathematically computing the expression levels using a model that discriminates whether or not the expression levels are correlated with each other. Lack of correlation in the sample obtained from the subject can indicate BC, risk of BC, extent of BC (e.g., metastasizing or non-metastasizing) and/or prognosis (e.g., likelihood and/or degree of responsiveness to a particular chemotherapy). Some embodiments provide methods for predicting resistance of individual tumors to a chemotherapeutic agents, e.g., by taking samples for individual tumors.

In some embodiments, COPD can be diagnosed by identifying lack of correlation (compared to controls) between a transcription factor and a gene associated with COPD. For example, some embodiments comprise assaying an expression level of CEBPG and/or E2F1 in a sample obtained from a subject; assaying an expression level of at least one other gene in the sample, where the other gene is associated with COPD; and mathematically computing the expression levels using a model that discriminates whether or not the expression levels are correlated with each other. Lack of correlation in the sample obtained from the subject can indicate COPD, risk of COPD, extent of COPD, and/or prognosis (e.g., likelihood and/or degree of responsiveness to a particular therapy). One of skill in the art will recognize that other cancer-related conditions and/or other lung-related conditions can also be diagnosed using the approaches described herein.

In some embodiments, the sample obtained comprises bronchial epithelial cells, e.g., NBECs. In preferred embodiments, as described above, the sample comprises readily-accessible cells, such as but not limited to, nasal epithelial cells, buccal epithelial cells or blood cells. In some embodiments, the subject is a smoker, e.g., an individual having a heavy smoking history.

In some embodiments, the other gene is selected from an AO gene and a DNAR gene, including, but not limited to XRCC1, ERCC5, GSTP1, SOD1, GPX1, ERCC1, CAT, GSTZ1 and/or ERCC2. Generally, the other gene is regulated by CEBPG and/or E2F1 in control samples. Expression levels can be assayed by any methods known in the art, e.g., any of the techniques provided above. Preferably, methods of the instant invention allow early detection of BC and/or COPD, improving efficacy of prevention. Methods described herein also can facilitate inclusion of only individuals at higher risk in trials for BC and/or COPD, which in turn can improve the cost-effectiveness of such studies.

In some embodiments, the model used to identify BC and/or risk thereof involves a relation between expression levels of CEBPG and one or more AO and/or DNAR genes, e.g., one or more AO and/or DNAR genes present at high incidence in NBECs of BCI but not present or present at low incidence in NBCI. For example, in some embodiments a ratio of TG/TF is used, as discussed above. In some embodiments, lack of correlation of CEBPG with each AO or DNAR gene is characteristic of NBEC from individuals who are more susceptible to BC. That is lack of correlation of CEBPG with a TG can indicate increased BC risk.

While CEBPG may play a major role in controlling AO and/or DNAR protection in NBEC, in each individual a combination of any of tens or hundreds of different DNA sequence variations may be responsible for decreased correlation between CEBPG and the other (normally-regulated) genes. In preferred embodiments, risk associated alleles that affect function of many different genes and regions within genes can be detected through this analysis. In some embodiments, the TG/CEBPG ratio for a set of genes can quantify the effect of functionally significant variants on BC risk, e.g., providing a model for increased risk. In such embodiments, lack of correlation is associated with individuals indicating high or low (TG/CEBPG) ratios relative to the regression line observed for NBCI.

For example, in some embodiments, a risk allele occurring in any of a collinear string of 50 bp in the bZip region of CEBPG increases risk. Although the prevalence of the rare allele for each nucleotide may be less than about 0.001, the chance of one of these rare alleles occurring in the 50 bp collinear string would be 50× about 0.001 or about 0.05 which is consistent with the measured risk for BC among heavy smokers. Some embodiments of this invention allow identification of this risk, e.g., using a ratio of TG/CEBPG. Additional details of determination and application of such models are provided in the Examples below.

In some embodiments, the invention provides kits for diagnosing biological states, e.g., kits for identifying a cancer-related condition, e.g., BC, and/or a lung-related condition, e.g., COPD. In one embodiment, such a kit comprises a standardized mixture comprising: a competitive template for a transcription factor and a competitive template for at least one other gene, where the competitive templates are at known concentrations relative to each other. Such a kit can be used to determine expression levels of the transcription factor and/or other gene, and the expression levels computed to diagnosis the condition.

For example, in one embodiment of a kit for diagnosing a cancer-related condition and/or a lung-related condition, the standardized mixture can comprise a competitive template for CEBPG e.g., a competitive template comprising a nucleic acid sequence consisting of SEQ ID NO: 12±about 100 bases; and a competitive template for at least one other gene, the other gene being associated with the cancer-related condition and/or lung-related condition. In another embodiment of a kit for diagnosing a cancer-related condition and/or a lung-related condition, the standardized mixture can comprise a competitive template for E2F1, e.g., a competitive template comprising a nucleic acid sequence consisting of SEQ ID NO: 13±about 100 bases; and a competitive template for at least one other gene, the other gene being associated with said cancer-related condition and/or lung-related condition. The other gene can be selected from an AO and DNAR genes, e.g., XRCC1, ERCC5, GSTP1, SOD1, GPX1, ERCC1, CAT, GSTZ1, and ERCC2. For example, in some specific embodiments, the competitive template for the other gene can comprise a nucleic acid sequence consisting of at least one sequence selected from SEQ ID NOS: 33, 39, 51, 63 and 69±about 100 bases for genes ERCC5 GPX1 GSTP1 SOD1 and XRCC1, respectively. In preferred embodiments, the kit can be used to test for risk for BC and/or COPD.

In some embodiments, the standardized mixture can further comprise primer pairs, e.g., for amplifying both the transcription factor (from the sample) and its competitive template and/or primer pairs for amplifying both the other gene (from the sample) and its competitive template. In some specific embodiments, for example, the primer pair can be selected from a primer pair listed in Table 1.

In some embodiments, kits and methods described herein provide more accurate identification of those at risk for BC and/or COPD, compared to traditional methods. More accurate identification of those at risk for BC and inclusion of such individuals in chemoprevention and/or early detection studies can lead to improved efficacy. Those of skill in the art will recognize that the methods provided herein can be applied to the diagnoses of other cancer-related conditions and/or other lung-related conditions, e.g., other cancer-related conditions and lung-related conditions provided herein.

B. Polymorphism Approach

In yet another aspect, the disclosure relates to methods and compositions for diagnosing a biological state using identified polymorphisms. In preferred embodiments, the identified polymorphism consists of a specific region of DNA that contains one or more nucleotide differences compared to controls. The nucleotide differences may differ from one subject to the next. However, one or more differences within the region are indicative of a given biological state.

Diagnosis of Cancer-Related Conditions and/or Lung-Related Conditions

For example, some embodiments provide a method of identifying a cancer-related condition or a lung-related condition in a subject comprising obtaining a sample from a subject, wherein the sample comprises a nucleic acid region corresponding to relevant polymorphism, comparing the region to a nucleic acid sequence consisting of the sequence found in controls, and identifying a nucleic acid difference. In some embodiments, the sequence from controls is a consensus sequence obtained, e.g., from a plurality of healthy individuals. In preferred embodiments, the sample obtained is a readily-accessible sample, e.g., one that can be obtained with a non-invasive or mildly-invasive technique. Such samples include, e.g., urine samples, bloods samples, semen samples, or more preferably saliva samples, buccal and/or nasal epithelial cell samples. For example, identified polymorphism(s) can allow diagnostic testing using more-readily accessible patient samples, such as peripheral blood and/or buccal smears and/or nasal epithelial cells In some embodiments, the nucleic acid region is a 5' regulatory region of CEBPG; and this region is compared to the nucleic acid sequence (of controls) consisting of the 5' regulatory region of CEBP±about 10, ±about 50, ±about 100, ±about 150, ±about 200, ±about 500, ±about 800, or about 1000 bases, wherein a nucleotide difference indicates a cancer- or lung-related condition.

In some embodiments, the nucleic acid region is a 3' un-translated region of CEBPG; and this region is compared to the nucleic acid sequence (of controls) consisting of the 3' un-translated region of CEBPG±about 10, ±about 50, ±about 100, ±about 150, ±about 200, ±about 500, ±about 800, or ±about 1000 bases, wherein a nucleotide difference indicates a cancer- or lung-related condition.

In some embodiments, the nucleic acid region is a bZip region of CEBPG; and this region is compared to the nucleic acid sequence (of controls) consisting of the bZip region of CEBPG±about 10, ±about 50, ±about 100, ±about 150, ±about 200, ±about 500, ±about 800, or ±about 1000 bases, wherein a nucleotide difference indicates a cancer- or lung-related condition.

In some embodiments, the nucleic acid region is a CEBPG recognition site; and this region is compared to the nucleic acid sequence (of controls) consisting of a CEBPG recognition site±about 10, ±about 50, ±about 100, ±about 150, ±about 200, ±about 500, ±about 800, or ±about 1000 bases, wherein a nucleotide difference indicates a cancer- or lung-related condition. For example, in some embodiments, the CEBPG recognition site is the CEBPG recognitions site for XRCC1, ERCC5, SOD1, GSTP1 and/or GPX1.

In some embodiments, the comparison involves identifying at least one base in the nucleic acid region, e.g., using methods as known in the art and/or provided herein. For example, in some embodiments, the region obtained form the sample and the sequence obtained from controls are compared by contacting the sample with a probe consisting of a the sequence obtained from controls (or a complementary sequence thereof) under conditions allowing hybridization; and detecting whether or not hybridization occurs. Specificity of hybridization can be assessed by varying degrees of stringency of the hybridization conditions, as known in the arts. Under suitable conditions, hybridization can indicate that the sample sequence is the same, sufficiently the same, significantly the same, or substantially the same as the control sequence, indicating lack of the condition or low risk thereof. Reduced hybridization can indicate that the sample sequence was different, sufficiently different, significantly different, or substantially different from the sample sequence (probe), indicating the condition or risk thereof. In addition, comparison of mismatch to perfect match oligonucleotide probes can be used to determine specificity of binding. In some embodiments, the cancer-related condition is bronchogenic carcinoma, a risk thereof, or responsiveness to a chemotherapeutic agent. In some embodiments, the lung-related condition is COPD or a risk thereof.

In some embodiments, the nucleotide difference is a single nucleotide polymorphism. In some embodiments, the nucleotide difference comprises more than one base pair change either consecutively or at various locations within the region, e.g., two or more SNPs within the region. For example, the nucleotide difference can involve at least about two, at least about three, at least about 5, at least about 10, at least about 20, or at least about 50 nucleotide differences. In some embodiments, the nucleotide difference involves less than about 80, less than about 100, less than about 150, less than about 200, less than about 300 or less than about 500 nucleotide differences.

In still some embodiments, more than one region can be compared to that of controls to diagnose a condition (or risk or prognosis thereof). For example, in identifying a cancer- and/or lung-related condition, the method can comprise identifying nucleotide differences in two or more nucleic acid regions selected from a 5' regulatory region of CEBPG, a 3' un-translated region of CEBPG; a bZip coding region of CEBPG; and a CEBPG recognition site of XRCC1, ERCC5, SOD1, GSTP1 and/or GPX1.

Some embodiments provide probes consisting of relevant nucleic acid sequences for identifying polymorphisms indicative of cancer- and/or lung-related conditions. Examples of four such probes include (i) a probe comprising a nucleic acid sequence consisting of a 5' regulatory region of CEBPG±about 10, ±about 50, ±about 100, ±about 150, ±about 200, ±about 500, ±about 800, or ±about 1000 bases; (ii) a probe comprising a nucleic acid sequence consisting of a 3' un-translated region of CEBPG±about 10, ±about 50, ±about 100, ±about 150, ±about 200, ±about 500, ±about 800, or ±about 1000 bases; (iii) a probe comprising a nucleic acid sequence consisting of a bZip region of CEBPG±about 10, ±about 50, ±about 100, ±about 150, ±about 200, ±about 500, ±about 800, or ±about 1000 bases; and (iv) a probe comprising a nucleic acid sequence consisting of a CEBPG recognition site±about 10, ±about 50, ±about 100, ±about 150, ±about 200, ±about 500, ±about 800, or ±about 1000 bases. One or more such probes can be anchored to a support, e.g., in an array, and/or provided in kits for use in identifying a cancer- and/or lung-related condition (e.g., BC and/or COPD), risk thereof, predicted response to treatment, etc.

III. Methods and Compositions for Treatment

Yet another aspect of the disclosure relates to methods and compositions for treating a biological state, e.g., by providing an agent that "makes up" for the lack of correlation between a transcription factor and a gene. For example, some embodiments comprise administering a therapeutic based on the identified lack of correlation; and/or the identified biomarker or combination of biomarker(s). Generally, the present disclosure provides methods, pharmaceutical compositions, and kits for the treatment of animal subjects. The term "animal subject" as used herein includes humans as well as other mammals. The term "therapeutic" can refer to any agent that can be used to treat animal subjects.

The term "treating" as used herein includes achieving a therapeutic benefit and/or a prophylactic benefit. By therapeutic benefit is meant eradication or amelioration of the underlying disorder being treated. For example, in a BC patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For example, with respect to BC, treatment can provide therapeutic benefit when an improvement is observed in the patient with respect to other disorders and/or discomforts that accompany BC, such as cough, dyspnea, hemoptysis, and/or pso-obstructive pneumonia. For prophylactic benefit, a therapeutic may be administered to a patient at risk of developing a disease condition, e.g., BC and/or COPD, or to a patient reporting one or more of the physiological symptoms of such conditions, even though a diagnosis may not have been made.

Treatment of Cancer-Related Conditions and/or Lung-Related Conditions

In some embodiments, the invention provides methods and compositions for treating a cancer-related condition, e.g., BC, and/or a lung-related condition, e.g., COPD. As indicated above, methods and compositions of the disclosure can be used in making a diagnostic decision and a therapeutic can be administered where indicated. Examples of therapeutics that can be administered, e.g., in treating a cancer-related and/or lung-related condition include, but at not limited to cis-platin, alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; EGFR inhibitors, such as Iressa® (gefitinib) and Tarceva® (erlotinib); proteosome inhibitors; antibodies, such as campath, Herceptin® (trastuzumab), Avastin® (bevacizumab), or Rituxan® (rituximab). Other therapeutics which may be used include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine. See, e.g., U.S. 2005/0137213. Examples of therapeutics that can be administered, e.g., in treating a cancer-related and/or lung-related condition also include, but are not limited to, erlotinib, canertinib, cetuximab, ABX-EGF, trastuzumab, imatinib, SU11274, PHA665752, AP23573, RAD001, CCI-779, bevacizumab, vatalanib, bexarotene, bortezomib, flavopiridol, oblimersen, VEGF inhibitors, selenium, 15-PGDH and/or 15-PGDH activators (e.g., NSAIDs like indomethacin), P13K/Akt inhibitors (e.g., deguelin and myo-inositol), PPAR-γ and/or PPAR-γ activators (e.g., p21 up-regulators, E-cadherin up-regulators, gelsolin up-regulators, cyclins D and E down-regulators, MUC1 down-regulators, MMP2 down-regulators, and α5-integrin down-regulators), DNA methyltransferase-1 inhibitors, HDAC and methyltransferase inhibitors, prostaglandin E2 inhibitors, prostacyclin and/or prostacyclin activators, 5-LOX inhibitors, COX inhibitors, LOX-COX inhibitors, 12-LOX inhibitors, EGFR inhibitors, leukotriene $A_4$ hydrolase modulators, cyclooxygenase-1 modulators, antioxidants, caratinoids, retinoids, such as etretinate, isotretinoin, β-carotene, fenretinide, anethole dithiolthione, 9-cis-retinoic acid, retinol, budesonide, α-tocopherol, retinyl palmitate, and the like. See, e.g., Hahn et al., *Hematol Oncol Clin N Am* 19: 343-367 (2005) and Hirsch et al, *J. Clinical Oncology* 23(14): 3186-3179 (2005). See also, e.g., Cohen et al., *Cancer Control.* 10:315-324 (2003) and Hong et al., *Science* 278: 1073-1077 (1997).

Without being limited to any given design and/or theory, better understanding of AO and DNAR gene transcription regulation can enable design of improved chemo-preventive and chemotherapeutic pharmaceuticals, as well as accompanying biomarkers that predict response. Performance of both classes of therapeutics can be affected by function of AO and/or DNAR genes. Developing pharmaceuticals that target regulation of AO and/or DNAR genes by CEBPG can be a productive avenue in many areas of health, including cancer prevention, cancer treatment, as well as inflammation and/or immunity.

Identified polymorphisms can also be used to develop therapeutics, e.g., therapeutics for treating and/or preventing cancer-related and/or lung-related conditions. For example, peptide molecules can be developed that have a therapeutic effect by interfering with or enhancing binding of transcription factors to hetero-dimeric proteins and/or to DNA recognition sites. See, e.g., Vassilev et al, *Science* 6(303): 8440848 (2004). One or more of such identified therapeutics can be administered where indicated, e.g., alone or in combination with other known therapeutics, e.g., other known therapeutics for treating cancer-related and/or lung-related conditions, e.g., as provided above.

EXAMPLES

Example 1

Collection of NBCI and BCI Samples

Normal bronchial epithelial cell (NBEC) and peripheral blood samples can be obtained from patients and a portion of each sample can be used to in the Examples described herein. Individuals can be recruited from among patients who are undergoing diagnostic bronchoscopy. Some indications for bronchoscopy include coughing up of blood, chronic cough, pneumonia resistant to antibiotics, and need to remove a foreign body. Some of these patients may be diagnosed with bronchogenic carcinoma (BCI), while others may have non-neoplastic conditions (NBCI). The age of these patients may range from approximately 20 to approximately 90, with most participants being between the ages of about 60 and about 75. NBEC samples are obtained according to previously described methods. See, e.g, Benhamou et al., *Carcinogenesis,* 8:1343-1350 (2002).

From each patient, NBEC samples and 20 ml of peripheral blood can be collected and processed, e.g., as previously described (Willey et al., *Am J Respir Cell Mol Biol* 17(1):114-124 (1997); Crawford et al., *Cancer Res.* 60:1609-1618 (2000)). Approximately 10-15 brush biopsies can be obtained from normal appearing mucosa at approximately the tertiary bronchi. If the patient has a local pathological condition, such as pneumonia, trauma, or BC, the brushes can be taken from the opposite side.

After each bronchoscopic brush biopsy, the brush can be swirled in approximately 3 ml of ice cold saline to dislodge and retrieve the cells. Approximately 500,000 to 1 million cells can be obtained with each brush. Thus, 10 brushes can yield about 5-10 million cells. These cells in 3 ml of ice cold saline can be divided up for extraction of RNA and protein and preparation of slides for IHC and FISH. Approximately 5 million cells can be used for nuclear extract protein extraction (see, e.g., Dignam et al, *Nucleic Acid Research* 11: 1475-1489 (1983)). This can yield approximately 100 ug of nuclear extract for EMSA and Western hybridization analyses. Approximately 1 million cells can be used for RNA extraction for the expression level measurements.

The 20 ml of peripheral blood may contain approximately $1-2 \times 10^8$ white blood cells. Most of these cells can be used to produce nuclear extracts for surface plasmon resonance (SPR) experiments described below. About 1-2 million cells can be used for RNA extraction for expression level measurements, and another about 1-2 million can be used for DNA extraction for sequencing studies.

Buccal and nasal epithelial samples can also be collected from BCI and NBCI providing bronchoscopic brush samples and peripheral blood samples for SNPs. Buccal and nasal epithelial samples can be obtained by brushing of the inside of the mouth or the nose. The buccal epithelial cell samples from BCI and NBCI can be handled in a similar way as the NBEC samples, as provided above.

Example 2

(a) Identification of CEBPG and E2F1 as Transcription Factor Biomarkers for BC

TF recognition sites common to GSTP1/GPX1, CAT/GPX3, and GPX3/SOD1 are identified through sequence analysis (Genomatix Software GmbH, Munich, Germany, http://genomatix.de/cgi-bin/eldorado/) (Quandt et al., *NAR,* 23: 4878-4884 (1995)), yielding sites for 11 TFs.

Standardized RT (StaRT)-PCR™ reagents (Willey et al., in *Methods in Molecular Biology* (ed. Shimkets, R. A.) 13-41 (Humana Press, Inc., Totowa, N.J., 2004) are optimized for ten of these TFs, including CEBPB, CEBPE, CEBPG, E2F1, E2F3, E2F4, E2F5, E2F6, EVI1, and PAX5. Four TFs expressed at low and invariant levels among multiple NBEC samples are evaluated no further. The remaining six, CEBPB, CEBPG, E2F1, E2F3, E2F6, and EVI, are evaluated for correlation with an expanded group of ten AO and six DNAR genes. Accession numbers for these genes are provided in Table 1, along with competitive template sequences for each gene analyzed, forward and reverse primer pair sequences for amplification, the position on the gene at which the primers hybridize, and the size of the PCR-amplified products.

NBEC samples are obtained by bronchial brush biopsy during diagnostic bronchoscopy as detailed above. StaRT-PCR™ is used to generate virtually-multiplexed transcript abundance (VMTA) data (Workman and Mark, *Spectroscopy,* 19:1-3 (2004)). Details of this method, including extensive validation of the method in independent laboratories, were published recently. Willey et al., in *Methods in Molecular Biology* (ed. Shimkets, R. A.) 13-41 (Humana Press, Inc., Totowa, N.J., 2004). Briefly, total mRNA samples extracted from NBEC are reverse transcribed using M-MLV reverse transcriptase and oligo dT primers as previously described (Benhamou et al., *Carcinogenesis,* 8: 134301350 (2002)). With StaRT-PCR™, an internal standard for each gene within a standardized mixture of internal standards (SMIS™) is included in each measurement. StaRT-PCR™ reagents for each of the measured genes, including primers and standardized mixtures of internal standards (SMIS™) are prepared according to previously described methods (competitive template and primer sequence information provided in Table 1 as discussed above).

VMTA values for the above 22 genes are measured in NBEC samples from 49 individuals including 24 NBCI and 25 BCI. Demographic data of patient providing NBEC samples are provided in Table 2 and VMTA data obtained is provided in Table 3. An internal standard controls for several known sources of variation during PCR, including inhibitors in samples, e.g., the presence of an inhibitor was the primary reason why it was not possible to obtain an E2F1 measurement in sample 147 (see Table 3).

Pearson analysis is performed on the normalized VMTA values for AO and DNAR genes and putative regulatory TFs. Data is provided in Table 4. In NBCI samples, the CEBPG TF is significantly ($p<0.01$) correlated with eight of the 16 AO or DNAR genes, specifically XRCC1, ERCC5, GSTP1, SOD1, GPX1, ERCC1, CAT and ERCC2. In contrast, in BCI samples CEBPG is not correlated with any of the AO or DNAR genes tested in this example. Analysis of each VMTA value relationship with age is assessed with Pearson's correlation, with gender by t-test, and with smoking history by ANOVA followed by Duncan's test. All statistical tests are two-sided test and are performed using SAS version 8.0 (SAS Institute, Cary, N.C.).

FIG. 3 (a-f) illustrate correlation of each of 6 TFs ((a) CEBPB, (b) CEBPG, (c) E2F1, (d) E2F3, (e) E2F6, (f) EVI1) with each of 5 genes XRCC1, ERCC5, GSTP1, SOD1, or GPX1. Each panel presents the correlation coefficients (r values) for one TF in relation to each of the five genes. Correlation is determined by Pearson's correlation following logarithmic transformation. The transformation may be necessary due to the wide range of expression of each gene among the individuals. In FIG. 3, the p value for each significant correlation is provided above the bar. Significance level is defined as ($p<0.01$) following Bonferroni adjustment for multiple comparisons, specifically comparison of each of the six TFs to each of the AO or DNAR genes. Comparison for significant differences between pairs of correlation coefficients is done by Fisher's Z-transformation test. (Workman and Mark, *Spectroscopy*, 19: 1-3 (2004)).

For CEBPG, presented in FIG. 3b, the difference in r value between NBCI and BCI is significant or nearly significant for each correlated gene, and the p value for each comparison is provided below the corresponding pair of bars. As FIG. 3b illustrates, the correlation between CEBPG and each of XRCC1, ERCC5, GSTP1, and SOD1 was significantly lower in BCI compared to NBCI and the difference was nearly significant for GPX1.

In NBCI, based on the $r^2$ values from Pearson's correlation analysis, CEBPG accounts for much of the variance in expression of XRCC1 (69%), ERCC5 (62%), GSTP1 (55%), SOD1 (44%), and GPX1 (52%). E2F1 accounts for some of the remaining variance. For example, in NBCI, E2F1 is correlated with GSTP1 (FIG. 3c) and the correlation is lower in BCI. However, the difference in correlation between NBCI and BCI is not significant. Further, when samples from all 49 NBCI and BCI were assessed as a single group, E2F1 is significantly correlated with ERCC5, GSTP1 and SOD1 (see Table 4). None of the other TFs tested in this Examples are correlated with XRCC1, ERCC5, GSTP1, SOD1, or GPX1 (FIG. 3a, d, e, f).

Figure 3B:
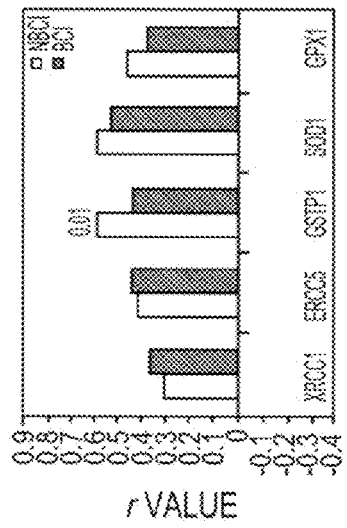
FIG. 3(a-h) illustrates correlation of each of 6 TFs ((a) CEBPB, (b) CEBPG, (c) E2F1, (d) E2F3, (e) E2F6, (f) EVI1) with each of 5 genes XRCC1, ERCC5, GSTP1, SOD1, or GPX1; and (g-h) illustrate CEBPG/XRCC1 data of FIG. 3b presented as scatter plots for (g) NBCI and (h) BCI.
Figure 3C:
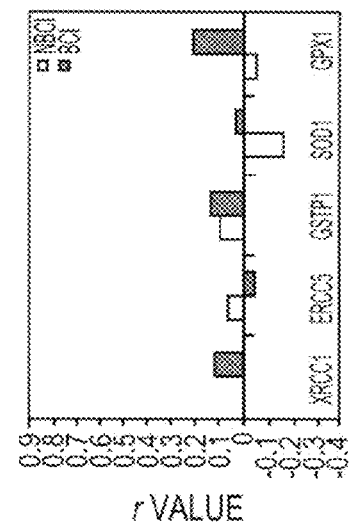
Figure 3E:
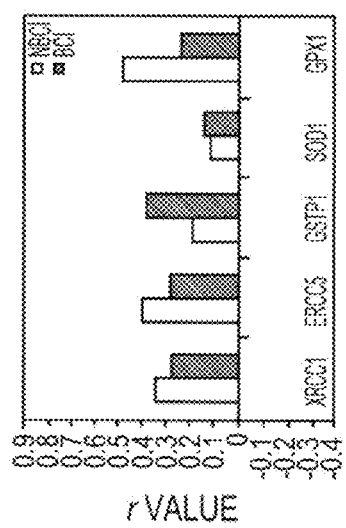
Figure 3F:
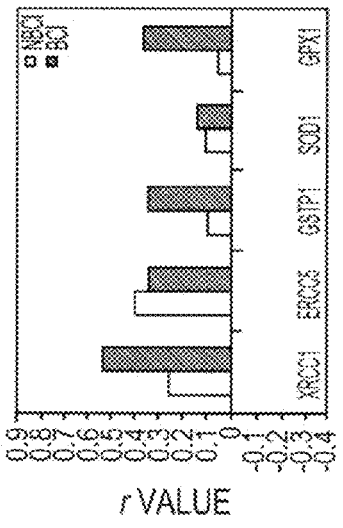
Figure 3A:
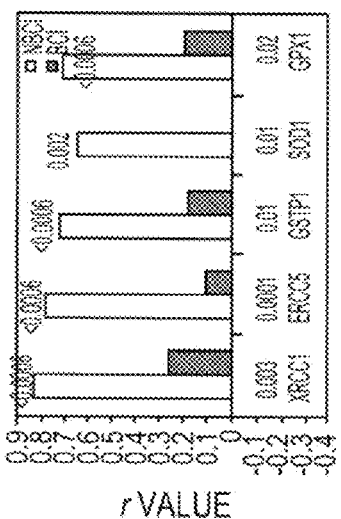
Figure 3D:
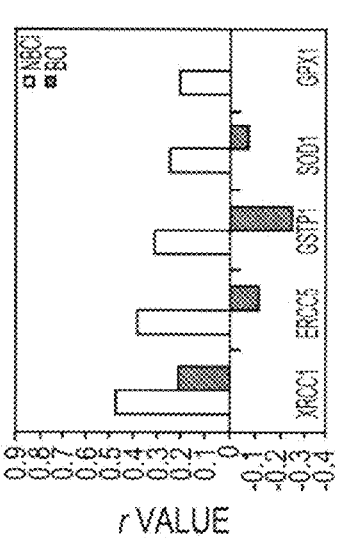
Figure 3G:
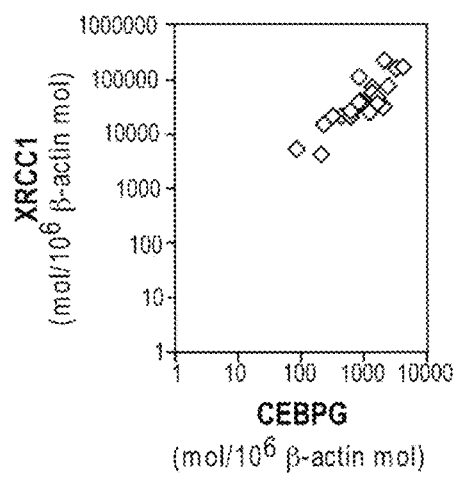
Figure 3H:
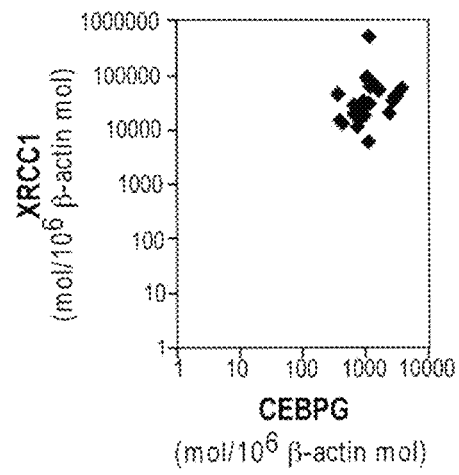

FIGS. 3(g-h) illustrate CEBPG/XRCC1 data from FIG. 3b presented as scatter plots for (g) NBCI and (h) BCI. Scatter plots of the relationship between CEBPG and XRCC1 in NBCI or BCI are representative of the other four genes (ERCC5, GSTP1, SOD1 and GPX1). CEBPG, XRCC1, ERCC5, GSTP1, SOD1 and GPX1 are not significantly correlated with age, gender, or smoking history in NBCI, BCI, or the combined group.

(b) Additional Data Identifying CEBPG as a Transcription Factor Biomarker for BC Expression levels of 16 selected AO and DNAR genes are found to be correlated in bivariate analysis of 12 NBCI and not correlated in 15 BCI. The NBCI and BCI groups are closely matched for age, gender, smoking history, and disease status and comprise Study 2 in this Example.

The correlated genes are subjected to TF recognition site analysis. Specifically, the El Dorado (Build 35) program from the Genomatix software package is used to search for TF recognition sites in regulatory regions of each of the 16 AO and DNAR genes. First, the software is used to locate the AO and DNAR genes within the genome and define 1101 base pairs of the promoter regions (1000 base pairs upstream of and 100 base pairs into the transcription start site) for each gene (Genomatix Software GmbH, Munich, Germany, http://genomatix.de/cgi-bin/eldorado/). The 1101 base pair sequences obtained from the El Dorado program are then used as the target sequences for putative TF recognition site identification using the MatInspector Version 4.2 program (Genomatix Software GmbH, Munich, Germany, http://genomatix.de/cgi-bin/eldorado/). The parameters used are the standard (0.75) core similarity and the optimized matrix similarity. The TF recognition sites identified in each of the correlated AO and DNAR genes are included in the CEBP family, E2F family, EVI1, and PAX5.

StaRT-PCR™ reagents are prepared for each of the TFs in each of these families. VMTA data for each of the TFs that have recognition sites shared among these target genes were collected from the NBEC samples of the 12 NBCI and 15 BCI. Of 11 TFs evaluated, 8 are expressed in NBEC, including CEBPG, CEBPA, CEBPB, E2F1, E2F3, E2F6, and EVI1.

The TFs are identified that share the pattern of correlation with target genes in NBCI, and loss of this correlation in BCI. The TF out of the eight assessed that had this characteristic was CEBPG. Each of the eight TFs and each of the 16 AO and DNAR genes can be assayed in an additional 12 NBCI and 13 BCI to determine whether CEBPG is responsible for regulation of the 10 AO and DNAR genes in NBCI and loss of correlation in BCI. The 12 NBCI and 13 BCI comprise Study 3.

In Studies 2 and 3, the 24 NBCI had and average age of 55 while the 25 BCI had and average age of 68. There were 18 males and 7 females among the BCI, while there were 12 males and 12 females among the NBCI. An algorithm to predict BC risk based on cigarette smoking history, age, and gender was developed from the demographic information gathered as part of the CARAT study (see e.g., Bach et al., *J Natl Cancer Inst*. 95: 470 (2003)). Based on this algorithm, among the NBCI the average calculated BC risk is 2.2% (range 1-15%) while among the BCI the average calculated risk is 6.8% (range 1-15%). Thus, although the incidence of BC among the 25 BCI in Studies 2 and 3 is 100%, the incidence of BC among individuals in the general population who have the same age, gender, and smoking history is only 6.8%. Ostensibly, the 25 BCI may be selected on the basis of genetically determined low protection against the oxidant and DNA damage stress posed by cigarette smoking.

Thus it can be determined that CEBPG would a) be correlated with each of the 10 genes that it was correlated with in NBCI, b) not be correlated with the 10 genes in BCI, and c) not be correlated with the six genes that it was not correlated with in either NBCI or BCI. It can be further predicted that d) each of the other six TFs assessed that were not correlated with the 10 AO or DNAR genes would demonstrate this pattern again.

Results

Figure 4A:
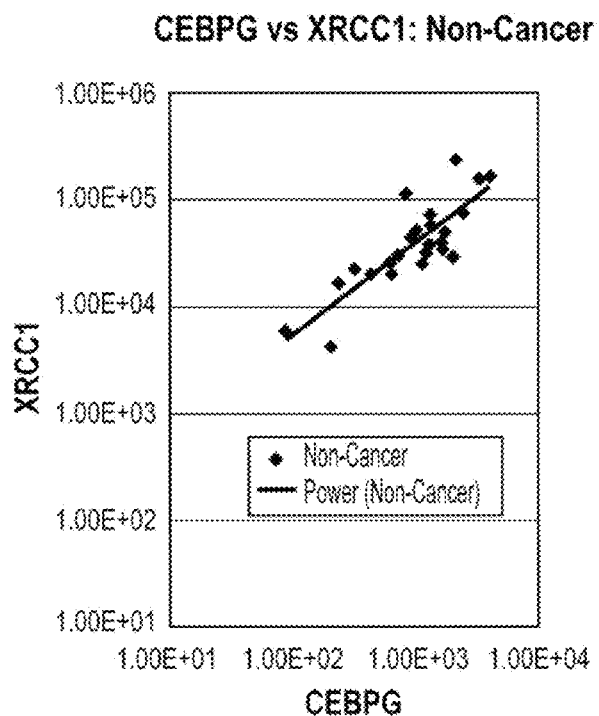
FIG. 4 (A-B) illustrates bivariate analysis between CEBPG with XRCC1 in (A) NBCI and (B) BCI.
Figure 4B:
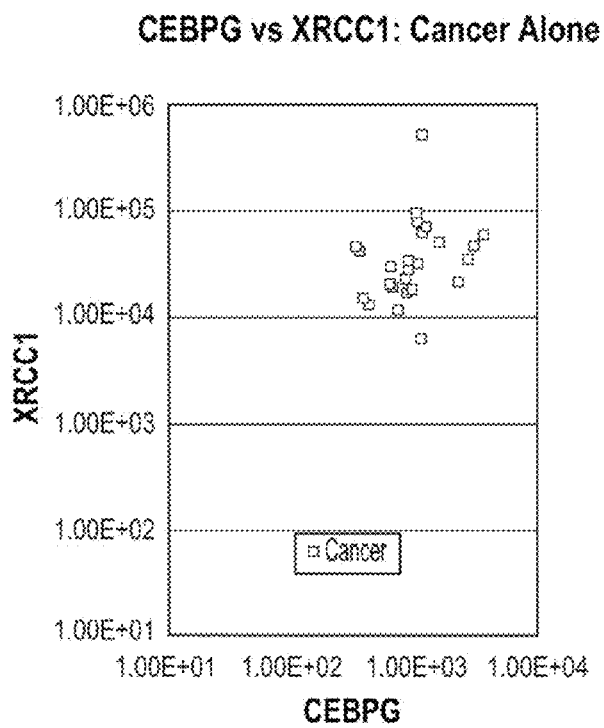
Figure 5:
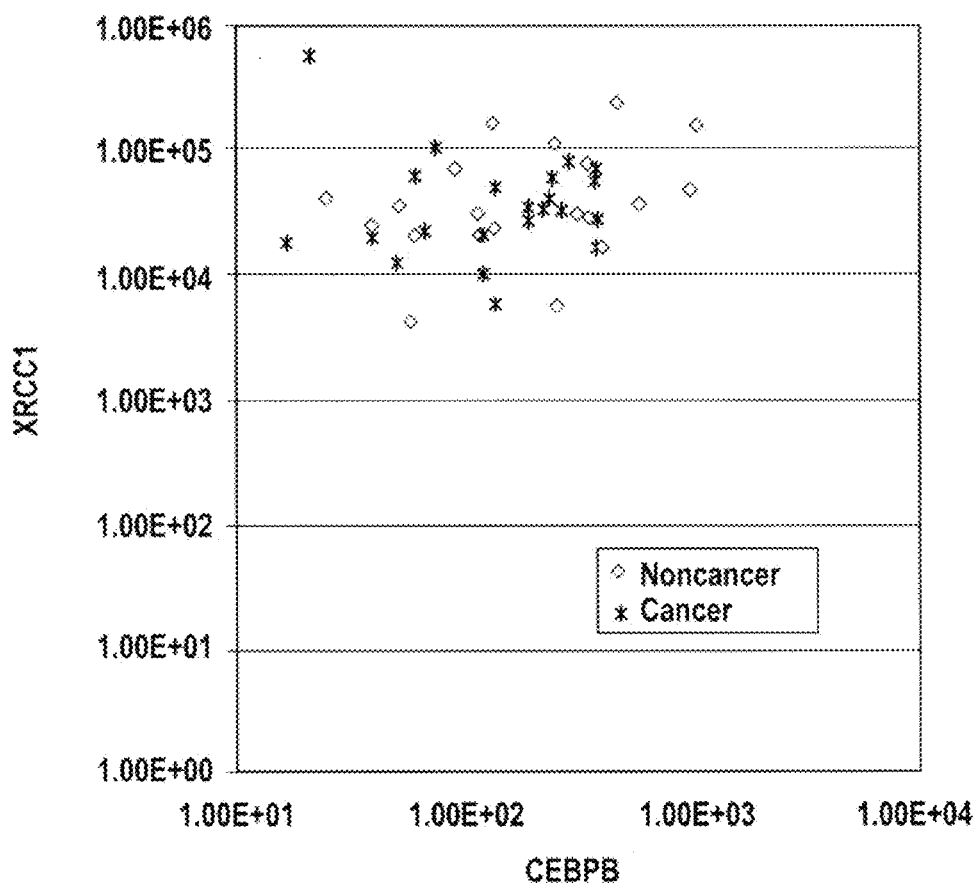
FIG. 5 illustrates the lack of correlation of CEBPB with XRCC1 in either NBCI or BCI.

Each of the above predictions is confirmed in a blinded analysis of VMTA data from Study 3 and further confirmed when VMTA data from Studies 2 and 3 are combined. The combined data from Studies 2 and 3 are presented in Tables 5-8. The data supporting the predictions are as follows:

a) For bivariate analysis of CEBPG with each of the AO or DNAR genes, the mean correlation coefficient and standard deviation in NBCI is 0.69+/−0.10 with average P value of 0.003 Table 5. An example of bivariate analysis between CEBPG and XRCC1 in NBCI is presented in FIG. 4a.

b) For analysis of CEBPG with the 10 AO and DNAR genes in BCI the correlation coefficient is 0.23+/−0.13 with average P value of 0.36, also shown in Table 5. The bivariate plot of CEBPG with XRCC1 in BCI is shown in FIG. 4b.

c) In bivariate analysis of CEBPG with each of the six genes that are not correlated in Study 2, there again is no correlation with CEBPG in Study 3 and the combined data are presented in Table 6.

d) In bivariate analysis, none of the seven other TFs, including CEBPA, CEBPB, EVI1, E2F1, E2F3, E2F6, and MYC, demonstrate the pattern observed with CEBPG (i.e. significant correlation with the 10 AO and DNAR genes in NBCI and no correlation in BCI). These findings are represented by results from bivariate analysis of VMTA data for CEBPB with each of the 10 AO and DNAR genes, presented in Table 7. FIG. 5 illustrate an example of the lack of correlation of CEBPB with XRCC1 in either NBCI or BCI.

e) Bivariate analysis of expression levels for each of the genes versus age, gender, and recent or cumulative smoking history reveals no correlation. Thus, there is little or no evidence that cigarette smoking affects regulation of the AO and DNAR genes included in this study. This is important because it can remove a potentially strong, confounding variable that may be difficult to control.

Additional Data Relating to E2F1 as a Transcription Factor Biomarker for BC

Of the eight TFs assessed, E2F1 is the only TF other than CEBPG to be significantly correlated with the 10 AO and DNAR genes. Results from bivariate analysis of E2F1 with each of the 10 genes are presented in Table 8. The differences compared to results presented in Table 5 for CEBPG are a) the mean correlation coefficient of bivariate analysis between E2F1 and each of the genes in NBCI (0.49+/−0.11) is lower than that observed for CEBPG, b) the mean correlation coefficient for analysis of E2F1 with the 10 genes in BCI is 0.46+/−0.11 which is not significantly lower compared to NBCI. These results suggest that E2F1 contributes to regulation of the 10 AO and DNAR genes, and that E2F1 may not play a role in the decreased correlation among the 10 genes in BCI compared to NBCI.

Example 3

Identification of a Model Distinguishing NBCI from BCI

Models that distinguish NBCI from BCI are derived from multivariate analysis and genetic programming software analysis of the VMTA data from a training set of individuals. These models are assessed using VMTA data obtained from a test set of an additional 25 NCBI and 25 BCI, matched for age, gender, and smoking history. Suitable models are refined through analysis of additional genes in the training sets and validation in additional sets.

Where possible, triplicate expression level measurements of each gene are performed. All tests can be performed for the NBCI group alone, the BCI group alone, and the combined groups. Student's t tests are performed to identify statistical differences between NBEC from NBCI and BCI for each gene. Statistical significance is set at $p<0.05$. All statistical analyses can be performed using SAS version 6.11 (SAS Institute, Cary, N.C.).

To confirm statistically significant inter-individual variation in gene expression levels, a one-factor ANOVA is performed. Pearson's correlation test is used to identify significant bivariate correlation between pairs of genes. TG/CEBPG ratio for each gene for each BCI is assessed relative to the confidence limits established for NBCI by Person's correlation test. A cut-off value is identified based on the regression line from bivariate analysis of VMTA data from NBCI. This model is evaluated in a blinded study for its accuracy in determining whether an individual is in the NBCI or BCI group.

The overall concept is that lack of correlation of CEBPG with each AO or DNAR gene is characteristic of NBEC from individuals at risk for BC. High or low (TG/CEBPG) ratios relative to the regression line observed for NBCI indicates lack of correlation and accordingly risk of BC. Due to the high correlation between CEBPG and TGs in NBCI, it is possible to determine with meaningful confidence the regulated gene expression level predicted to accompany the CEBPG level in NBEC from a particular NBCI. The TG/CEBPG ratio for selected AO and DNAR genes can then be used to predict risk-conferring polymorphic alleles in each individual.

If the TG/CEBPG ratio is above or below a particular level, determined from analysis of the TG/CEBPG for NBCI, a polymorphism that increases risk is indicated. In any particular BCI individual, who by definition is at high risk, the TG/CEBPG for a particular gene may be high, low, or unchanged relative to the regression line observed in NBCI (e.g. FIG. 4 CEBPG vs XRCC1). That is, regulation of many of the TGs by CEBPG may be normal in a particular BCI. However, for any particular individual at increased risk for BC, altered regulation of a sufficient number of TGs is expected. This provides models for distinguishing BCI from NBCI.

Upon identifying models that distinguish BCI from NBCI based on expression levels measured in NBEC, the models are assessed in other tissues, e.g., tissues obtainable by non-invasive techniques, including, e.g., buccal and/or nasal epithelial cells. Bivariate correlation patterns observed for NBCI and BCI in NBEC may also be observed in these other tissues. About 50 buccal epithelial samples and peripheral blood cell samples are collected from the same patients providing NBEC. Expression levels are determined for use with the models. The data are compared to data obtained for NBEC and to SNP analysis of peripheral blood cells from the same patients.

Example 4

(a) Detection of BC by Identifying Loss of Correlation

Discriminate analysis of VMTA data for all 22 genes from Example 2a can be conducted to identify models that identify each individual as NBCI or BCI. Using 36 of the 49 individuals as a training set (19 NBCI and 17 BCI), the best models involve an interaction between CEBPG and one or two other genes. The six best models are then evaluated in a blinded validation set of 6 NBCI and 7 BCI, matched for age, gender, and smoking history. The best model correctly identifies 10/13 individuals as NBCI or BCI, providing 77% accuracy, 100% specificity and 70% sensitivity. The models identified through linear discriminant analysis of VMTA data from NBEC can have sufficient accuracy for the purpose of identifying individuals at risk for BC to improve efficacy of chemoprevention and early detection clinical trials. For example, even 70% specificity is not surprising given that some individuals at risk would not have yet developed BC.

(b) Additional Data for Detecting BC by Identifying Loss of Correlation

Multi-variate analysis of the VMTA data for CEBPG and the 10 genes from Example 2b is conducted to identify models that distinguish NBCI from BCI. Analysis is done initially on VMTA data from 34 of the 50 individuals (17 NBCI and 17 BCI) and this yields several models that are 100% accurate. These models can be evaluated using the remaining blinded 16 individuals (8 NBCI and 8 BCI). Several of the models involving CEBPG were at least 75% accurate for distinguishing NBCI from BCI.

Example 5

Identification of Polymorphisms

This example describes identification of polymorphisms in the correlated TF, AO and/or DNAR genes for which certain alleles are represented at a significantly higher rate in BCI.

Recognition sites for CEBP and E2F families, PAX5, and EVI1 are identified as common to the regulatory regions of AO and DNAR genes that are correlated in NBEC of NBCI. These common TF recognition sites are identified through regulatory region sequence analysis with Mattinspector™ software. Of the eight TFs that could bind to the above recognition sites, CEBPG TF expression levels are found to be correlated with expression levels of 10 selected AO and DNAR genes in NBEC of NBCI but not in NBEC of BCI. E2F1 expression levels are correlated with expression levels of AO and DNAR genes in both NBCI and BCI.

CEBPG, CEBPA, CEBPB, FOS and the 10 correlated AO and DNAR genes can be analyzed for sequence variants. Polymorphisms assessed with priority are those that could affect transcription regulation, protein function, post-transcriptional processing and/or stability, and/or protein-protein binding, including those in the upstream regulatory region, and those in the 3' UTR, translated region, and 5' UTR of the coding region. Initially, groups that are likely to have a maximal difference in genetically determined risk can be compared, including older, heavy smoker NBCI on the one hand and younger, light or non-smoker BCI on the other. Using SNP Consortium databases, polymorphisms, e.g., SNPs, are identified in the 3' untranslated, translated, 5' untranslated, and regulatory regions of correlated genes and of CEBPG and E2F1.

DNA extracted from peripheral blood WBC can be sequenced through a commercial service. Because the C/EBP genes are several thousand bp long, the regions with known function can be assessed with greatest priority. These high priority regions include those responsible for DNA binding, heterodimer formation, and activation, and the 3' UTR. Most of the known SNPs in these genes are in the 3' UTR which may play a role in transcript stability and/or processing (e.g. polyadenylation) See, e.g., Conne et al, *Nature Medicine* 6(6): 637-41 (2000).

CEBPA, B, and G proteins are assessed for known SNPs using bioinformatics software available through NCBI. The list of known SNPs is provided below in Table 9. It is evident from this table that most SNPS in CEBPG and A occur in the 3' untranslated region (UTR). For each of the three C/EBP's, there are no known SNPs in the regulatory region or coding region. Although no common SNPs are known in these regions, it is likely that numerous uncommon polymorphisms, e.g., SNPs, exist in the population (Mohrenweiser et al., *Toxicologic Pathology* 32: 1336-45 (2004)) and that a change in any of several nucleotides at a sensitive region can lead to altered function. For CEBPG, A, and B, and their isoleucine heterodimer partners including FOS, the regions of particular interest are those that participate in transactivation, heterodimer formation and/or DNA binding. CEBPG is truncated and lacks the activating domain (Cooper et al, *Nucleic Acids Res.* 23: 4371-4377 (1995)). However, it binds DNA with the same affinity as the full CEBP proteins (Roman et al, *Gene Dev.* 4: 1404-1415 (1990)). Therefore, for CEBPG the focus is directed to the bZip region responsible for heterodimer formation and DNA binding.

For the target genes, the primary interest is in the regulatory regions, specifically the regions containing recognition sites for CEBPG. For example, the known SNPs in the 1100 bp regulatory region (1000 upstream and 100 bp downstream of the transcription start site) of XRCC1 are presented in Table 10. The frequency of each allele at each polymorphism in NCBI can be determined and compared to frequency of each allele at each polymorphism in BCI. Below are three of many scenarios that can exist in a particular individual to explain the presumed 5-10% incidence of genetically determined increased risk.

(i) Each of five co-regulated genes contributing to risk has a polymorphism in the recognition site for CEBPG. The prevalence of the risk allele is 0.5 in each recognition site. $0.5 \times 0.5 \times 0.5 \times 0.5 \times 0.5 = 0.5 \times 0.0625 = 0.0312$. If the incidence of the polymorphism for any of them is less than 0.5 or if the low expression phenotype requires homozygosity for any of the genes, the frequency of the phenotype will be less than this.

(ii) There is a polymorphism in a recognition site for a transcription factor that controls all five genes. Either the frequency is 0.25 and homozygosity is required ($0.25 \times 0.25 = 0.052$) or the frequency is 0.05 and heterozygosity is responsible ($0.05 \times 0.95 = 0.0475$).

(iii) As reported by Mohrenwieder (Mohrenweiser et al., *Toxicologic Pathology* 32: 1336-45 (2004)), there are many low frequency polymorphisms that affect AO and/or DNAR function. For example, a risk allele occurring in any of a collinear string of 50 bp in the bZip region will increase risk. Although the prevalence of the rare allele for each nucleotide may be less than 0.001, the chance of one of these rare alleles occurring in the 50 bp collinear string would be $50 \times 0.001$ or 0.05.

Because variation in a different nucleotide may be responsible for the altered AO and/or DNAR function in each individual, among the BCI there may be a higher overall prevalence of rare alleles throughout a functional region of interest compared to the rest of the gene, and this difference may not be observed among NBCI. For example, there may be higher prevalence of rare alleles among the BCI through the bZip region of CEBPG compared to the rest of the CEBPG, while among NBCI there is no difference. Data can be evaluated for significant ($p<0.05$) differences with one-way ANOVA.

In assessing high numbers of polymorphic sites in a relatively low number of individuals, a pattern at a polymorphic site may appear to be associated with BC patients by chance. This can be controlled for by initially considering each polymorphic site pattern to be associated with BC as a model. Each of these models can be validated in a subsequent blinded study, e.g., as detailed above.

A power analysis is conducted based on allele frequencies of known SNPs in the correlated TF, AO and/or DNAR genes. A suitable sample size for each gene is calculated assuming an allele frequency of 5% in one group and 95% in the other group. To achieve a power of at least 80%, 5 subjects per group are used. For example, for 10 SNPs, (e.g. one for each gene), 100 subjects are use. Power calculation can be carried out using the Fisher Exact Procedure on nQuery 5.0. Where additional AO and/or DNAR genes that are regulated by CEBPG and/or that contribute to protection are not assessed, sensitivity may be reduced (e.g., high false negatives may be observed), but specificity may not be affected (e.g., false positives remain low).

Example 6

Identification of Polymorphisms by Exploring Mechanistic Bases for Correlation of AO and DNAR Genes with CEBPG in NBCI but not in BCI The mechanistic bases for correlation of AO and DNAR genes with CEBPG in NBCI but not in BCI can be explored to further identify polymorphic regions indicative of BC. Established technology can be applied to assess transcript regulation in primary cells/tissues. Measuring transcription regulation can involve three components: (a) VMTA measurements target genes regulated by the TF, (b) analysis if DNA recognition site sequences for the TF that reside in the regulatory region of target genes, and (c) analysis of TF interaction with each recognition site. VMTA data generated by StaRT-PCR™ can be used to measure expression levels of target genes for (a); DNA sequencing and other methods are readily available for high throughput analysis of SNPs for (b); and established EMSA, SPR, and Western blot methods can be used for (c). Due to the small size of NBEC samples obtainable by bronchoscopic brush biopsy, more sensitive methods, e.g., Standardized ImmunoPCR (SiPCR) is preferred in some embodiments. See, e.g., U.S. patent application Ser. No. 11/103,397. These methods can be used for measuring affinity of TFs for particular DNA sequences, and affinity between different putative TF heterodimer proteins to the small NBEC samples obtained by bronchoscopic biopsy.

Loss of correlation may be due to direct or indirect regulation of TGs by CEBPG. For example, CEBPG expression levels may be correlated with expression levels of AO and DNAR genes, but CEBPG may not regulate them, for example, if a) it is a co-factor necessary but not sufficient for transfection of other genes, or b) it is co-regulated by the same TFs as the co-regulated AO genes, but has no effect on them. To determine whether CEBPG is regulating the AO and DNAR genes, a CEBPG expression vector is introduced into cells that express low levels of CEBPG and a suitable target gene. Cultured NBEC from certain individuals may be suitable for this purpose. See, e.g., Willey et al., *Am J Respir Cell Mol. Biol.* 19(1):6-17 (1998). Also, a reporter construct can be transfected containing the regulatory region for GSTP1 into bronchogenic carcinoma cell lines that express varying endogenous levels of CEBPG. A list of measurable biological correlates to SNPs that have different functional affects is presented in Table 11.

Figure 6:
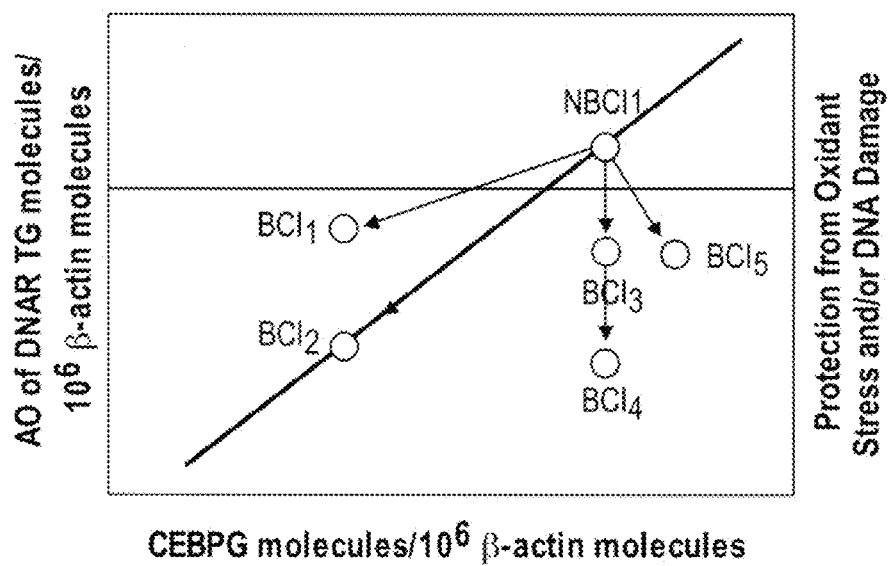
FIG. 6 illustrates a schematic bivariate analysis of a TG/CEBPG expression levels in one NBCI (NBCI1) and 5 BCI (BCI$_{1-5}$).

FIG. 6 illustrates a schematic bivariate analysis of TG/CEBPG expression levels in one NBCI (NBCI1) and 5 BCI ($BCI_{1-5}$). In this schematic, AO or DNAR expression levels are highly correlated with CEBPG expression levels in NBCI individuals. Thus, the bivariate coordinates for NBCI, including individual NCBI1, fall along the thick regression line. The thin horizontal line represents the TG expression level adequate to protect against oxidant and DNA damage stress that occurs in a heavy cigarette smoker. In NBCI, the correlation between AO or DNAR target gene expression level and CEBPG expression level, e.g., due to regulation by CEBPG, is associated with NBEC protection from oxidant and DNA damage stress (NBCI1 coordinates occur above the thin horizontal line).

In BCI, represented by $BCI_{1-5}$, there are reduced TG expression levels, indicated by the arrows. Further, there is low or absent correlation between TG and CEBPG expression levels and most of the bivariate coordinates are represented as not being along the regression line. This schematic represents a) CEBPG regulates transcription of key AO and DNAR TG and decreased correlation is accompanied by reduced protection from oxidant and DNA damage stress and b) because BCI are selected on the basis of reduced protection, they are likely to manifest reduced correlation between CEBPG and TG expression levels in their NBEC.

Whether an individual BCI CEBPG expression level is lower or greater than that in NBCI can indicate possible mechanisms for loss of correlation and thus regions to be analyzed for polymorphism indicative of disease risk. Whether an individual BCI TG/CEBPG ratio falls above, on, or below the regression line can also indicate possible mechanisms for loss of correlation and thus the regions to be analyzed for polymorphisms indicative of disease risk. Table 12 illustrates individual BCI TB/CEBPG data falling above, on, or below an NBCI regression line. Possible mechanisms for decreased correlation include reduced CEBPG transcription and/or reduced functional interaction between CEBPG and TG regulatory regions:

Reduced CEBPG Transcription

In $BCI_1$ and $BCI_2$ there is lower CEBPG transcription, resulting in a TG expression level below that adequate for protection against the AO/DNA damage experienced by cigarette smokers. Variation in TG expression level between $BCI_1$ and $BCI_2$ may be due to other TFs that regulate TG being induced by stress to different degrees in different individuals. In BCI with reduced CEBPG expression levels, the regulatory region of CEBPG is analyzed for polymorphisms different from NBCI, e.g., that might affect affinity of TFs for recognition site, e.g., as discussed in more detail below.

Reduced Functional Interaction Between CEBPG and TG Regulatory Region

In $BCI_3$, $BCI_4$, and $BCI_5$ the TG expression levels are below that necessary to provide adequate protection against AO and DNA damage stress in heavy cigarette smokers even though CEBPG expression levels are (substantially) the same or higher than that in NBCI1. For example, the CEBPG expression levels are the same as in an individual with higher CEBPG function in $BCI_3$ and $BCI_4$. The CEBPG expression levels are higher in $BCI_5$, e.g., due to feedback signals that insufficient protection is present. In $BCI_3$, levels of non-CEBPG TFs that regulate the TG are higher than in $BCI_4$. In each situation, the TG expression level achieved is inadequate to provide adequate protection. In BCI with (substantially) the same or higher CEBPG expression levels, polymorphisms associated with lower function of CEBPG compared to NBCI are searched for, e.g., as discussed in more detail below.

BCI with TG/CEBPG ratios similar to $BCI_1$, $BCI_2$ or $BCI_{3-4}$ are identified for each of the AO or DNAR TGs, as provided in Table 12. According to the mechanisms described herein, BCI with ratios the same or similar to $BCI_1$ or $BCI_2$ have polymorphisms that cause reduced transcription of CEBPG relative to NBCI1, while those with ratios the same or similar to BCI$_{3-5}$ have polymorphisms that cause reduced function of CEBPG. These hypotheses are tested by evaluating BCI with characteristic TG/CEBPG ratios as described below:

BCI with TG/CEBPG Above the NCBI Regression Line

BCI 061102 (Table 12) is analogous to BCI$_1$ (FIG. 6) in that TG/CEBPG ratio falls above the NBCI regression line. As stated in Table 12, the increased TG/CEBPG ratio may be due to is decreased rate of synthesis and/or decreased stability of CEBPG transcripts. Decreased transcription of CEBPG can occur due to a polymorphism involving the regulatory region of CEBPG or affecting the function of a TF that regulates CEBPG. Decreased stability may be associated with a polymorphism in the 3' untranslated region (UTR).

In BCI with increased TG/CEBPG values (e.g., BCI 061102), the regulatory region of CEBPG is analyzed for polymorphisms different from NBCI, e.g., that might affect affinity of TFs for recognition site. Where differences are observed, the sequences are synthesized and assessed for affinity with TF (purchased from commercial source) by SPR analysis.

In BCI with increased TG/CEBPG values (e.g., BCI 061102), the 3' UTR of CEBPG can be analyzed for polymorphisms different from NBCI that account for reduced stability. Reduced stability can be measured by nuclear run-on assays as known in the art.

Also, the function of TFs that regulate CEBPG can be studied, e.g., by transiently transfecting a luciferase reporter construct containing regulatory region of CEBPG into PMNs of NBCI vs BCI.

BCI with TG/CEBPG Below the NBCI Regression Line

BCI 010902 (Table 12) is analogous to BCI$_{3-5}$ (FIG. 6) in that TG/CEBPG ratio falls below the NBCI regression line. For BCI 010902, TG/CEBPG is significantly reduced relative to the NBCI regression line for 8 of the 10 AO or DNAR TG assessed. For example, the ERCC5/CEBPG ratio predicted from the NBCI regression line is 61, but the value for BCI 010902 is 5.

In some BCI with TG/CEBPG below the NBCI regression, this may be due to a polymorphism (e.g., an SNP) in CEBPG, or in a gene that forms a heterodimer with CEBPG, such as CEBPA, CEBPB, or FOS. In this scenario, the binding efficiency of CEBPG for the CEBP recognition site is less than it is in NBCI. To test this, CEBPG, CEBPA, CEBPB, and FOS are isolated from peripheral blood cells of BCI that have TG/CEBPG values like BCI 010902. This is done by first purifying the TF using sequence-specific oligo bound to biotin, mixing with avidin metallic beads then using magnetic separator (Kroeger et al, Analytical Biochemistry 250: 127-129 (1997)). SPR is then used to assess affinity of CEBPG for the CEBP recognition site in the TG and affinity of CEBPG for the recognition site in the presence of CEBPA or CEBPB according to established methods (see, e.g., Rutigliano et al., *Int J Oncol* 12(2): 337-43 (1998); Linnell et al., *J Biol Chem* 275: 12231-12236 (2004)). These results are compared to those obtained from NBCI samples for which the TB/CEBPG ratio is on the NBCI regression line.

In BCI with reduced TG/CEBPG that show reduced CEBPG binding efficiency, CEBPG, CEBPA, CEBPB and/or FOS can be analyzed for polymorphisms different form NBCI, e.g., polymorphisms associated with reduced transcription of TG by CEBPG.

In some BCI with TG/CEBPG below the NBCI regression, this may be due to a polymorphism (e.g., an SNP) in the CEBPG recognition site for each of the affected TGs. To test this, recognition sites of the TGs from such BCI are analyzed for polymorphisms different from NBCI. Affinity of CEBPA, B, or G extracted from NBCI or BCI NBEC can also be compared for affinity with the recognition sites with or without the polymorphism(s). Purified CEBPA, B, and G are commercially available (e.g. Abcam, Abnova, or Active Motif) and can be obtained to establish and calibrate the SPR measurement method, e.g., as described above. Standardized immunoPCR, referred to above, can quantify the concentration of bound or free CEBPG in relationship to target gene expression level, in relationship to a recognition site of interest within the small primary NBEC samples available from bronchoscopy. For example, standardized immuno-PCR reagents can be developed for CEBPA, B, G, and FOS, e.g., to enable standardized, numerical measurement of each of the TFs, with lower detection threshold (e.g., less than about 50 molecules in some embodiments, as opposed to greater than about 10 million molecules for Elisa or EMSA). This can enhance understanding of these important interactions among the genes that regulate protection of NBEC from oxidants and DNA damaging agents.

Example 7

Transcript Abundance Cancer Risk Threshold

Figure 7:
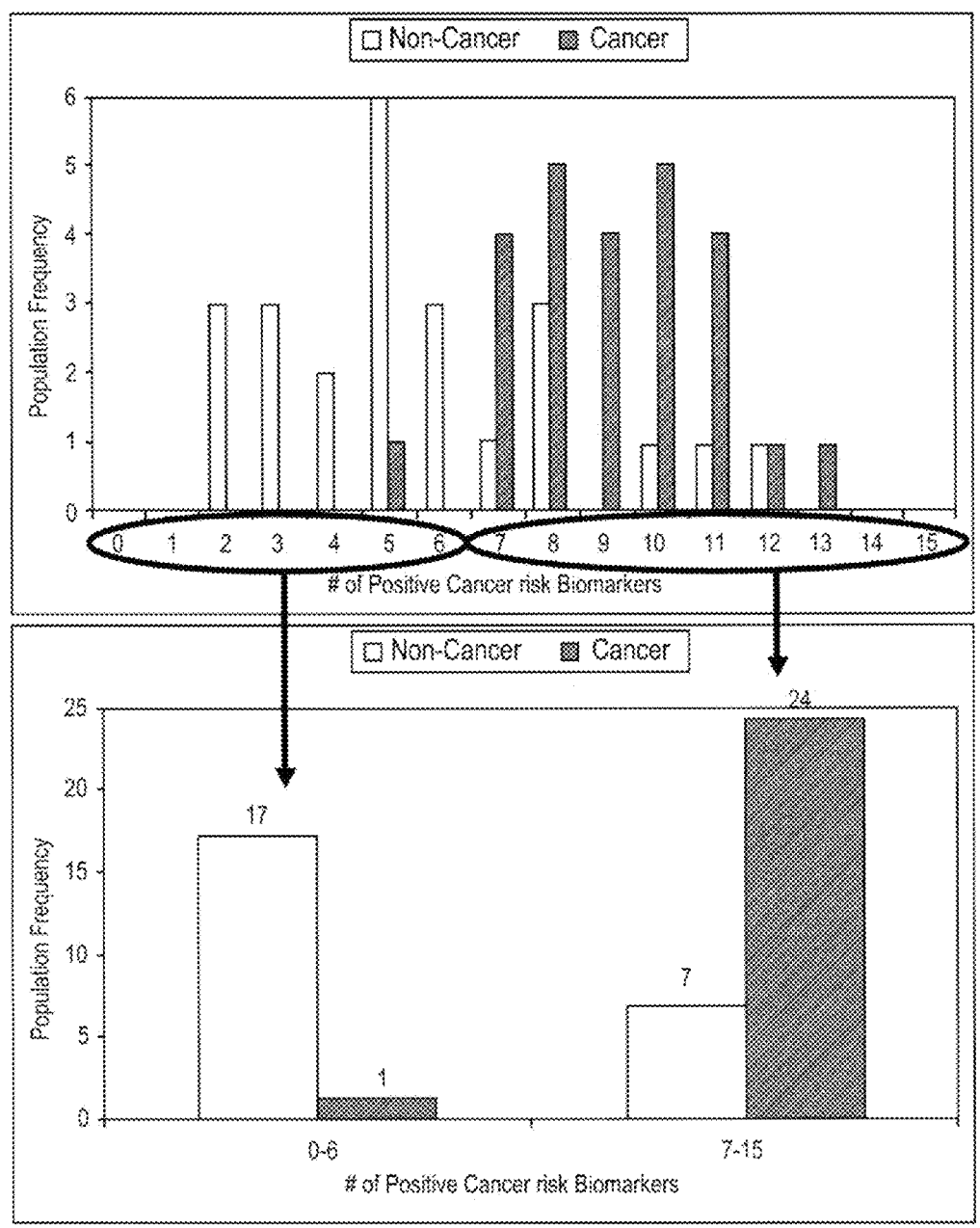
FIG. 7 illustrates a histogram of cancer diagnosis frequency sorted by sum of positive cancer risk biomarkers for a 15 gene biomarker.

Transcript abundance data for 25 genes in normal bronchial epithelial cell samples from 24 non-bronchogenic carcinoma and 25 bronchogenic carcinoma individuals were the subject of this study. For each gene, a threshold level of TA that most accurately separated BC from non-BC individuals was determined empirically. In one embodiment, 15 genes were utilized to separate the two groups. For each gene, depending on whether the TA level was above or below the threshold, the sample was assigned a 1 or 0 (Table 13; FIG. 7). The values for each of the 15 genes were totaled for each sample.

For example, a biomarker was developed that accurately predicted which individuals were cancer patients using the following 15 genes: CEBPG, E2F1, E2F6, XRCC1, ERCC4, ERCC5, GPX1, GPX3, GSTM3, GSTP1, GSTT1, GSTZ1, MGST1, SOD1 and CAT. Using a total value cut-off of greater than or equal to 7 as a biomarker for BC individuals, one false negative and seven false positives were identified among the 49 individuals assessed, yielding a sensitivity of 96% and specificity of 71% (FIG. 7). Given the correlations described herein, an individual with false positive results are at an increased risk for development of bronchogenic carcinoma in the future.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the disclosure described herein may be employed in practicing the disclosure. It is intended that the following claims define the scope of the disclosure and that methods and compositions within the scope of these claims and their equivalents be covered thereby.

TABLE 1

(SEQ ID NOS 1-69, respectively, in order of appearance)
Sequence for each primer used for StaRT-PCR (forward and reverse)
VMTA measurement or for preparation of internal standard (CT).

| Gene | Accession # | Primer | Sequence | Position | Product |
|---|---|---|---|---|---|
| ACTB | X00351 | Forward | 5' ATC CTC ACC CTG AAG TAC CC 3' | 231 | |
| | | Reverse | 5' CCA TCT CTT GCT CGA AGT CC 3' | 704 | 493 bp |
| | | CT | 5' CCA TCT CTT GCT CGA AGT CCG CCA CCC AGG TCC AGA CGC A 3' | 568 | 377 bp |
| CAT | X04076 | Forward | 5' CCA GAA GAA AGC GGT CAA GA 3' | 1492 | |
| | | Reverse | 5' AAC CTT CAT TTT CCC CTG GG 3' | 1822 | 350 bp |
| | | CT | 5' AAC CTT CAT TTT CCC CTG GGC CAG TGA TGA GCG GGT TAC A 3' | 1699 | 247 bp |
| CEBPB | NM_005194 | Forward | 5' TGT CCA AAC CAA CCG CAC AT 3' | 1412 | |
| | | Reverse | 5' AGC AAC AAG CCC GTA GGA AC 3' | 1657 | 265 bp |
| | | CT | 5' AGC AAC AAG CCC GTA GGA ACA CGC GTT CAG CCA TGT TTA A 3' | 1571 | 199 bp |
| CEBPG | U20240 | Forward | 5' CGG TTG AAA AGC AAG CAG AAA GCA 3' | 488 | |
| | | Reverse | 5' GAT CCC AGA AAA TAG CCT CCA ATG 3' | 814 | 350 bp |
| | | CT | 5' GAT CCC AGA AAA TAG CCT CCA ATG AAC ATT CAA GCC ACA AGC TC 3' | 726 | 282 bp |
| E2F1 | M96577 | Forward | 5' TGA TAC CCC AAC TCC CTC TA 3' | 2076 | |
| | | Reverse | 5' AAA GCA GGA GGG AAC AGA GC 3' | 2452 | 396 bp |
| | | CT | 5' AAA GCA GGA GGG AAC ACA GCA CTG CAC GGA CCA CAG G 3' | 2363 | 327 bp |
| E2F3 | Y10479 | Forward | 5' TGA AAG CCC CTC CAG AAA CAA G 3' | 1019 | |
| | | Reverse | 5' GCA GCA GGG GAG GCA GTA AGT T 3' | 1336 | 339 bp |
| | | CT | 5' GCA GCA GGG GAG GCA GTA AGT TGG GGA GGC CAG AGG AGA AAG GT 3' | 1253 | 278 bp |
| E2F6 | AF059292 | Forward | 5' GGG CCT GCT GCC ATC AAA AAT A 3' | 99 | |
| | | Reverse | 5' CCG CTT TCG GAC TCC CAG TTT 3' | 283 | 205 bp |
| | | CT | 5' CCG CTT TCG GAC TCC CAG TTA GCG ATA CAT CAA AAC GAG G 3' | 184 | 125 bp |
| ERCC1 | M13194 | Forward | 5' CTG GAG CCC CGA GGA AGC 3' | 739 | |
| | | Reverse | 5' CAC TGG GGG TTT CCT TTG 3' | 1049 | 328 bp |
| | | CT | 5' CAC TGG GGG TTT CCT TGG AAG GCC AGA TCT TCT CTT 3 | 928 | 240 bp |
| ERCC2 | X52221 | Forward | 5' GGC CTT CTT CAC CAG CTA C 3' | 1608 | |
| | | Reverse | 5' GTA GTC CGT CTT GCC CCT G 3' | 2004 | 415 bp |
| | | CT | 5' GTA GTC CGT CTT GCC CCT GTG GAA CTG GTC CCG CAG GT 3' | 2597 | 346 bp |
| ERCC4 | U64315 | Forward | 5' AGT GCA TCT CCA TGT CCC GCT ACT A 3' | 2213 | |
| | | Reverse | 5' CGA TGT TCT TAA CGT GGT GCA TCA A 3' | 2578 | 390 bp |
| | | CT | 5' CGA TGT TCT TAA CGT GGT GCA TCA ACA GGC TGT GGC TTG CTT TGT 3' | 2433 | 265 bp |
| ERCC5 | D16305 | Forward | 5' AAG GAA AGA GAA AGA AGC AGC AGC CA 3' | 3087 | |
| | | Reverse | 5' CAA ACA CAG ATC TGG CGG TCA CGA GG 3' | 3501 | 440 bp |
| | | CT | 5' CAA ACA CAG ATC TGG CGG TCA CGA GGA GCT TCC TTC ACT GAG TTC TGC GAA T 3' | 3401 | 366 bp |
| EVI1 | NM_005241 | Forward | 5' CGC CGG ATA TCC ACG AAG A 3' | 302 | |
| | | Reverse | 5' ATG CTG AGA GCG AAT GTG C 3' | 711 | 428 bp |
| | | CT | 5' ATG CTG AGA GCG AAT GTG CTT AAA TGC CTT GGG ACA CT 3' | 587 | 323 bp |
| GPX1 | Y00433 | Forward | 5' CCT GGT GGT GCT CGG CTT CC 3' | 522 | |
| | | Reverse | 5' CAA TGG TCT GGA AGC GGC GG 3' | 852 | 350 bp |
| | | CT | 5' CAA TGG TCT GGA AGC GGC GGA CCG GAG ACC AGG TGA TGA G 3' | 757 | 279 bp |
| GPX3 | D16360 | Forward | 5' GCA GAG CCG GGG ACA AGA GAA 3' | 113 | |
| | | Reverse | 5' CTG CTC TTT CTC TCC ATT GAC 3' | 471 | 379 bp |
| | | CT | 5' CTG CTC TTT CTC TCC ATT GAC GCT CTT CCT GTA GTG CAT TCA 3' | 298 | 227 bp |

TABLE 1-continued (SEQ ID NOS 1-69, respectively, in order of appearance)
Sequence for each primer used for StaRT-PCR (forward and reverse)
VMTA measurement or for preparation of internal standard (CT).

| Gene | Accession # | Primer | Sequence | Position | Product |
|---|---|---|---|---|---|
| GSTM1,2,4,5 | J03817 | Forward | 5' GGG ACG CTC CTG ATT ATG AC 3' | 122 | |
| | | Reverse | 5' GCA AAC CAT GGC CGC TTC CC 3' | 442 | 340 bp |
| | | CT | 5' GCA AAC CAT GGC CGC TTC CCT TCT CCA AAA TGT CCA CAC G 3' | 301 | 219 bp |
| GSTM3 | J05459 | Forward | 5' GTG CGA GTC GTC TAT GGT TC 3' | 23 | |
| | | Reverse | 5' AGT TGT GTG CGG AAA TCC AT 3' | 342 | 339 bp |
| | | CT | 5' AGT TGT GTG CGG AAA TCC ATT GCT CTG GGT GAT CTT GTT C 3' | 230 | 247 bp |
| GSTP1 | X08058 | Forward | 5' TCC GCT GCA AAT ACA TCT CC 3' | 305 | |
| | | Reverse | 5' TGT TTC CCG TTG CCA TTG AT 3' | 616 | 331 bp |
| | | CT | 5' TGT TTC CCG TTG CCA TTG ATT AGG ACC TCA TGG ATC AGC A 3' | 485 | 220 bp |
| GSTT1 | X79389 | Forward | 5' GCT CTA CCT GGA CCT GCT GT 3' | 12 | |
| | | Reverse | 5' GGA ACA CAG GGA ACA TCA CC 3' | 351 | 359 bp |
| | | CT | 5' GGA ACA CAG GGA ACA TCA CCT AGA GCA GGA TGG CCA CAC T 3' | 199 | 227 bp |
| GSTZ1 | U86529 | Forward | 5' TCA CCC CCT ACC CTA CCA TCA CC 3' | 806 | |
| | | Reverse | 5' ATT TCA GCG CGG GCA TTC TTT 3' | 1267 | 482 bp |
| | | CT | 5' ATT TCA GCG CGG GCA TTC TTT CCG CAT TCT CAT CTC AGC CTC AC 3' | 1161 | 399 bp |
| mGST1 | J03746 | Forward | 5' GTC GGA GCA CGG ATC TAC CAC A 3' | 404 | |
| | | Reverse | 5' TTC CTC TGC TCC CCT CCT ACC TA 3' | 623 | 242 bp |
| | | CT | 5' TTC CTC TGC TCC CCT CCT ACC TAT TTT CAG CAA CCT GTA AGC C 3' | 505 | 144 bp |
| SOD1 | X02317 | Forward | 5' TGA AGG TGT GGG GAA GCA TTA 3' | 153 | |
| | | Reverse | 5' TTA CAC CAC AAG CCA AAC CAC 3' | 492 | 360 bp |
| | | CT | 5' TTA CAC CAC AAG CCA AAC GAC TGA TGC AAT GGT CTC CTG AGA 3' | 384 | 273 bp |
| XPA | D14533 | Forward | 5' CTC GGC GAC GGC GGC TGC GGC TAC TGG AG 3' | 178 | |
| | | Reverse | 5' TGT CGG ACT TCC TTT GCT TCT TCT AAT GC 3' | 629 | 480 bp |
| | | CT | 5' TGT CGG ACT TCC TTT GCT TCT TCT AAT GCT CTT TTT TCT AAA TCA CAG TCT 3' | 487 | 360 bp |
| XRCC1 | M36089 | Forward | 5' CCC CTG AAG AGA CCA AAG CA 3' | 1906 | |
| | | Reverse | 5' CCA TTG AAG GCT GTG ACG TA 3' | 2241 | 355 bp |
| | | CT | 5' CCA TTG AAG GCT GTG ACG TAT CAG GGA CTG GCA GAT G 3' | 2142 | 276 bp |

TABLE 2

Demographic data of patients providing NBEC samples

| Subject # | Group | Age | Gender | Histology | Smoking Hx[2] | Ethnicity |
|---|---|---|---|---|---|---|
| 63 | NBCI[1] | 77 | M | | 75 | W[3] |
| 64 | NBCI | 47 | F | | 45 | W |
| 136 | NBCI | 38 | M | | 25 | A.A.[4] |
| 139 | NBCI | 44 | F | | 17.5 | W |
| 150 | NBCI | 70 | F | | 45 | W |
| 156 | NBCI | 46 | F | | NS[5] | A.A. |
| 157 | NBCI | 60 | M | | >100 | W |
| 194 | NBCI | 57 | M | | 3 | W |
| 210 | NBCI | 40 | M | | 34 | W |
| 257 | NBCI | 69 | F | | 20 | W |
| 261 | NBCI | 73 | F | | NS | W |
| 282 | NBCI | 83 | F | | 60 | W |
| 285 | NBCI | 69 | F | | NS | W |
| 296 | NBCI | 43 | F | | 20 | W |
| 305 | NBCI | 50 | F | | 40 | W |
| 315 | NBCI | 64 | M | | N/A[6] | W |
| 330 | NBCI | 39 | M | | NS | W |
| 331 | NBCI | N/A | N/A | | N/A | N/A |
| 334 | NBCI | 51 | M | | >50 | W |
| 336 | NBCI | 31 | F | | NS | W |
| 337 | NBCI | 32 | M | | 22 | N/A |
| 339 | NBCI | 59 | M | | 50 | W |
| 361 | NBCI | 73 | F | | NS | H[7] |
| 363 | NBCI | 50 | M | | 20 | A.A. |
| 34 | BCI[8] | 80 | M | NSCLC[9] | 40 | W |
| 71 | BCI | 63 | M | NSCLC | 100 | W |
| 85 | BCI | 73 | F | SQ[10] | >100 | W |
| 88 | BCI | 85 | M | SQ | 75 | W |
| 99 | BCI | 63 | M | NSCLC | 45 | W |
| 118 | BCI | 72 | M | SQ | 30 | W |
| 146 | BCI | 64 | F | SCLC[11] | 45 | W |
| 147 | BCI | 76 | M | SCLC | 75 | W |
| 158 | BCI | 88 | M | SCLC | 115.5 | W |
| 167 | BCI | 60 | F | NSCLC | 50 | W |

TABLE 2-continued

Demographic data of patients providing NBEC samples

| Subject # | Group | Age | Gender | Histology | Smoking Hx[2] | Ethnicity |
|---|---|---|---|---|---|---|
| 171 | BCI | 67 | M | SCLC | 100 | W |
| 191 | BCI | 75 | M | SQ | 54 | W |
| 211 | BCI | 71 | M | SQ | 50 | W |
| 212 | BCI | 65 | M | SQ | 67.5 | W |
| 247 | BCI | 75 | F | SQ | 50 | W |
| 255 | BCI | 60 | F | NSCLC | 30 | W |
| 259 | BCI | 68 | M | CS[12] | 137.5 | W |
| 271 | BCI | 58 | M | AC[13] | 94.5 | W |
| 287 | BCI | 65 | F | NSCLC | 50 | W |
| 300 | BCI | 56 | M | SQ | 34 | W |
| 306 | BCI | 46 | M | SQ | 30 | W |
| 314 | BCI | 69 | F | BC[14] | NS | W |
| 329 | BCI | 76 | F | PD[15] | >37.5 | W |
| 335 | BCI | 75 | M | SCLC | 58 | A.A. |
| B3 | BCI | 63 | M | SQ | 60 | W |

[1]Non-bronchogenic carcinoma individual;
[2]Pack years;
[3]White;
[4]African-American;
[5]Non-smoker;
[6]Not available;
[7]Hispanic;
[8]Bronchogenic carcinoma individual;
[9]Non-small cell lung cancer;
[10]Squamous carcinoma;
[11]Small cell lung cancer;
[12]Carcinoma-in-situ;
[13]Adenocarcinoma;
[14]Bronchogenic Cancer, histology not specified;
[15]Poorly differentiated carcinoma.

TABLE 3

Virtually-Multiplexed Transcript Abundance (VMTA) data.
VMTA data for each gene (in the form of molecules/$10^6$ β-actin molecules) from all experiments are included in a Standardized Expression Database ™ (SED). These data become directly comparable to previously published VMTA data from this laboratory, or to VMTA data collected by others using the NCI-funded (R24 CA 95806) Standardized Expression Measurement (SEM) Center. The data presented here represent more than 5,000 VMTA measurements conducted in multiple experiments. The sixteen AO or DNAR genes and each of the six TF genes except for E2F1 were measured in each NBEC sample from 49 individuals (24 NBCI and 25 BCI).

| Subj#1 | GROUP | CEBPB | CEBPG | E2F1 | E2F3 | E2F6 | EVI1 | CAT | ERCC1 | ERCC2 | ERCC4 |
|---|---|---|---|---|---|---|---|---|---|---|---|
| 63 | NBCI | 7.2E+03 | 6.4E+02 | 2.7E+02 | 1.9E+02 | 3.4E+02 | 6.1E+01 | 2.0E+04 | 1.1E+05 | 3.8E+03 | 1.1E+02 |
| 64 | NBCI | 7.9E+03 | 1.7E+03 | 2.0E+03 | 2.0E+01 | 1.7E+02 | 2.5E+01 | 2.5E+04 | 3.0E+05 | 3.4E+03 | 8.1E+01 |
| 136 | NBCI | 6.2E+03 | 2.1E+02 | 7.0E+02 | 1.0E+02 | 5.0E+01 | 6.0E+01 | 2.9E+03 | 7.4E+03 | 5.9E+02 | 5.6E+01 |
| 139 | NBCI | 4.5E+03 | 3.4E+03 | 2.3E+04 | 5.6E+02 | 1.0E+03 | 1.0E+03 | 6.1E+05 | 1.2E+06 | 2.2E+04 | 3.9E+03 |
| 150 | NBCI | 8.5E+03 | 7.4E+02 | 1.6E+02 | 1.1E+02 | 4.1E+01 | 3.2E+02 | 3.5E+04 | 1.7E+05 | 5.7E+03 | 6.9E+02 |
| 156 | NBCI | 2.1E+04 | 1.2E+03 | 7.5E+02 | ND | ND | 1.4E+02 | 1.5E+04 | 1.8E+05 | 2.0E+03 | 2.9E+02 |
| 157 | NBCI | 2.3E+04 | 4.1E+03 | 3.1E+03 | 2.1E+02 | 6.1E+02 | 1.4E+02 | 3.5E+05 | 5.6E+05 | 8.4E+03 | 1.6E+03 |
| 194 | NBCI | 6.5E+03 | 2.1E+03 | 2.9E+02 | 2.6E+02 | 8.5E+02 | 4.7E+02 | 4.5E+04 | 6.1E+05 | 4.7E+03 | 4.4E+02 |
| 210 | NBCI | 1.0E+04 | 2.1E+03 | 7.6E+02 | 4.0E+02 | 6.1E+02 | 3.6E+02 | 7.6E+04 | 7.6E+04 | 3.4E+03 | 7.7E+02 |
| 257 | NBCI | 1.1E+04 | 1.8E+03 | 2.7E+02 | 8.9E+02 | 1.7E+03 | 9.7E+02 | 1.0E+05 | 2.6E+05 | 1.6E+03 | 7.6E+02 |
| 261 | NBCI | 7.6E+03 | 1.3E+03 | 2.5E+02 | 1.7E+02 | 1.6E+02 | 9.4E+01 | 4.4E+04 | 2.7E+05 | 5.1E+03 | 4.6E+02 |
| 282 | NBCI | 6.4E+03 | 1.2E+03 | 5.4E+02 | 4.1E+01 | 2.9E+01 | 1.2E+02 | 4.1E+04 | 1.0E+05 | 6.0E+03 | 8.1E+02 |
| 285 | NBCI | 2.6E+03 | 4.4E+02 | 2.5E+03 | 1.1E+03 | ND | 1.2E+02 | 3.7E+04 | 9.1E+04 | 1.6E+03 | 7.7E+03 |
| 296 | NBCI | 1.9E+04 | 1.0E+03 | 1.0E+03 | ND | 2.8E+01 | ND | 6.9E+04 | 2.5E+05 | 3.6E+03 | 1.7E+02 |
| 305 | NBCI | 1.1E+03 | 9.1E+01 | 6.1E+02 | ND | 8.7E+01 | 2.6E+02 | 2.0E+04 | 4.9E+04 | 4.3E+02 | 2.8E+02 |
| 315 | NBCI | 3.5E+03 | 1.3E+03 | 1.2E+03 | 2.0E+02 | 7.5E+02 | 6.1E+02 | 4.7E+04 | 2.1E+05 | 2.7E+03 | 2.4E+03 |
| 330 | NBCI | 2.7E+03 | 2.4E+03 | 4.0E+02 | 1.1E+02 | 3.5E+02 | 4.0E+02 | 3.6E+04 | 8.3E+04 | 1.5E+03 | 1.7E+03 |
| 331 | NBCI | 7.3E+03 | 1.3E+03 | 8.0E+02 | ND | ND | ND | 8.6E+04 | 2.6E+05 | 6.5E+02 | 6.4E+02 |
| 334 | NBCI | 3.7E+03 | 6.1E+02 | 1.1E+03 | 2.3E+01 | 1.9E+01 | 4.0E+01 | 7.8E+04 | 1.4E+05 | 2.5E+03 | 1.3E+03 |
| 336 | NBCI | 3.6E+03 | 8.4E+02 | 2.8E+03 | 4.3E+02 | 1.2E+02 | 2.5E+02 | 8.9E+04 | 2.1E+05 | 7.9E+03 | 3.1E+03 |
| 337 | NBCI | 5.0E+03 | 9.3E+02 | 1.1E+03 | 1.6E+02 | 2.5E+02 | ND | 6.5E+04 | 1.9E+05 | 3.3E+03 | 1.3E+03 |
| 339 | NBCI | 2.5E+03 | 3.2E+03 | 5.2E+02 | 3.4E+01 | 4.3E+01 | 6.3E+01 | 5.0E+04 | 8.7E+04 | 2.3E+03 | 7.7E+02 |
| 361 | NBCI | 7.9E+03 | 2.5E+03 | 6.7E+02 | 5.8E+02 | 1.4E+03 | 3.5E+02 | 6.7E+04 | 2.5E+05 | 1.5E+03 | 2.8E+03 |
| 363 | NBCI | 6.2E+03 | 1.7E+03 | 1.4E+03 | 1.1E+02 | 1.9E+02 | 5.2E+01 | 7.6E+04 | 1.4E+05 | 3.7E+03 | 7.3E+02 |
| 34 | BCI | 1.9E+03 | 1.7E+03 | 5.7E+02 | 2.4E+02 | 1.2E+02 | 3.7E+02 | 6.7E+04 | 5.6E+05 | 6.1E+03 | 1.5E+03 |
| 71 | BCI | 7.6E+03 | 1.2E+03 | 1.3E+03 | 1.7E+01 | 1.5E+02 | 2.1E+01 | 9.5E+04 | 6.7E+05 | 1.8E+04 | 2.4E+02 |
| 85 | BCI | 1.0E+04 | 9.7E+02 | 8.7E+02 | 6.3E+01 | ND | ND | 2.6E+04 | 4.9E+04 | 1.1E+03 | 3.9E+02 |
| 88 | BCI | 1.5E+03 | 4.0E+02 | 4.2E+02 | 1.1E+02 | ND | ND | 3.1E+04 | 2.9E+04 | 2.7E+03 | 3.6E+02 |
| 99 | BCI | 1.4E+04 | 3.3E+03 | 2.6E+03 | 2.2E+02 | 3.1E+03 | 1.4E+02 | 2.1E+05 | 2.0E+05 | 3.7E+03 | 9.3E+02 |
| 118 | BCI | 1.5E+03 | 1.2E+03 | 2.8E+02 | ND | ND | 1.4E+02 | 2.4E+04 | 3.5E+04 | 1.9E+03 | 1.2E+03 |
| 146 | BCI | 1.9E+04 | 1.2E+03 | 2.3E+02 | 1.2E+02 | 1.6E+03 | 6.0E+01 | 3.1E+04 | 1.4E+05 | 4.9E+03 | 2.7E+02 |
| 147 | BCI | 2.8E+03 | 1.3E+03 | N/A[2] | 3.6E+02 | 2.8E+02 | 3.8E+02 | 6.1E+04 | 3.0E+05 | 2.7E+03 | 1.1E+03 |
| 158 | BCI | 4.9E+03 | 8.8E+02 | 1.9E+02 | 2.8E+01 | 4.0E+02 | 6.8E+01 | 2.2E+04 | 1.4E+05 | 1.7E+03 | 1.5E+02 |
| 167 | BCI | 6.7E+03 | 9.2E+02 | 4.2E+02 | 1.8E+02 | 8.2E+02 | 3.8E+02 | 8.9E+04 | 1.1E+05 | 2.2E+03 | 2.8E+02 |
| 171 | BCI | 1.0E+04 | 3.9E+03 | 3.2E+03 | 5.1E+02 | 8.9E+01 | 2.4E+02 | 5.3E+05 | 8.3E+05 | 1.3E+04 | 6.3E+02 |
| 191 | BCI | 1.6E+04 | 2.4E+03 | 1.5E+02 | 1.5E+02 | 7.1E+01 | 1.2E+02 | 2.0E+04 | 9.6E+04 | 2.5E+03 | 3.4E+02 |
| 211 | BCI | 3.8E+03 | 1.1E+03 | 6.5E+02 | 6.3E+02 | 3.2E+02 | 2.9E+02 | 8.3E+04 | 3.5E+05 | 2.8E+03 | 3.2E+02 |
| 212 | BCI | 1.8E+04 | 2.8E+03 | 6.0E+02 | 3.4E+02 | 2.0E+02 | 2.2E+02 | 3.4E+04 | 2.1E+05 | 5.2E+03 | 3.0E+02 |
| 247 | BCI | 6.5E+03 | 7.5E+02 | 6.4E+02 | 1.8E+02 | ND | 1.2E+02 | 7.8E+04 | 4.4E+04 | 5.5E+02 | 2.7E+03 |
| 255 | BCI | 1.9E+04 | 1.1E+03 | 6.1E+02 | 1.8E+01 | 2.3E+02 | 7.6E+01 | 1.1E+05 | 6.5E+05 | 1.2E+04 | 1.2E+03 |

TABLE 3-continued

Virtually-Multiplexed Transcript Abundance (VMTA) data.

VMTA data for each gene (in the form of molecules/$10^6$ β-actin molecules) from all experiments are included in a Standardized Expression Database ™ (SED). These data become directly comparable to previously published VMTA data from this laboratory, or to VMTA data collected by others using the NCI-funded (R24 CA 95806) Standardized Expression Measurement (SEM) Center. The data presented here represent more than 5,000 VMTA measurements conducted in multiple experiments. The sixteen AO or DNAR genes and each of the six TF genes except for E2F1 were measured in each NBEC sample from 49 individuals (24 NBCI and 25 BCI).

| | | | | | | | | | | | | |
|---|---|---|---|---|---|---|---|---|---|---|---|---|
| 259 | BCI | 8.4E+03 | 6.4E+02 | 5.1E+02 | ND | 6.7E+01 | 4.0E+01 | 4.7E+04 | 1.5E+05 | 2.6E+03 | 3.8E+02 | |
| 271 | BCI | 4.1E+03 | 6.6E+02 | 1.4E+03 | 6.5E+01 | 2.7E+02 | 1.9E+02 | 9.1E+04 | 1.5E+05 | 1.6E+03 | ND | |
| 287 | BCI | 8.7E+03 | 1.1E+03 | 9.5E+01 | 7.4E+01 | 4.0E+01 | 2.6E+02 | 4.7E+04 | 1.2E+05 | 6.5E+03 | 1.1E+02 | |
| 300 | BCI | 4.9E+03 | 4.4E+02 | 4.1E+02 | 4.4E+01 | ND | 5.1E+01 | 3.4E+04 | 6.9E+04 | 1.0E+03 | 1.0E+03 | |
| 306 | BCI | 6.5E+03 | 6.8E+02 | 4.9E+02 | 4.4E+01 | ND | 1.7E+01 | 3.7E+04 | 2.5E+05 | 2.8E+03 | 3.2E+02 | |
| 314 | BCI | 4.4E+03 | 9.3E+02 | 4.8E+02 | 3.1E+02 | ND | 1.9E+02 | 5.3E+04 | 6.2E+04 | 4.5E+03 | 5.2E+02 | |
| 329 | BCI | 1.4E+04 | 3.5E+02 | 2.4E+02 | ND | ND | ND | 7.9E+04 | 1.5E+05 | 1.4E+03 | ND | |
| 335 | BCI | 4.2E+03 | 3.7E+02 | 2.2E+03 | 3.3E+02 | 2.4E+02 | 2.4E+02 | 4.8E+04 | 1.9E+05 | 9.8E+03 | 3.1E+02 | |
| B3 | BCI | 7.4E+03 | 9.3E+02 | 1.4E+02 | 2.4E+02 | 1.8E+02 | 3.8E+02 | 3.4E+04 | 1.6E+05 | 2.2E+03 | 2.8E+02 | |

| Subj# | ERCC5 | GPX1 | GPX3 | GSTM15 | GSTM3 | GSTP1 | GSTT1 | GSTZ1 | MGST1 | SOD1 | XPA | XRCC1 |
|---|---|---|---|---|---|---|---|---|---|---|---|---|
| 63 | 4.3E+04 | 8.4E+05 | 1.5E+03 | 7.3E+03 | 3.9E+03 | 1.9E+06 | ND[1] | 3.1E+03 | 1.7E+05 | 1.6E+05 | 2.5E+03 | 2.1E+04 |
| 64 | 2.0E+05 | 4.4E+05 | 3.1E+02 | 1.5E+04 | 2.6E+03 | 3.5E+06 | 6.4E+03 | 2.0E+03 | 1.6E+05 | 6.5E+05 | 2.2E+03 | 4.2E+04 |
| 136 | 1.9E+04 | 2.0E+05 | 5.2E+02 | 6.3E+03 | 2.2E+03 | 5.3E+05 | ND | 8.9E+02 | 3.2E+04 | 5.3E+04 | 1.1E+03 | 4.4E+03 |
| 139 | 4.6E+05 | 1.8E+06 | 3.2E+03 | 5.2E+04 | 8.3E+03 | 3.2E+07 | ND | 2.8E+04 | 8.4E+05 | 2.2E+06 | 2.6E+04 | 1.6E+05 |
| 150 | 7.2E+04 | 2.1E+05 | 2.8E+03 | 1.1E+04 | 1.1E+03 | 1.5E+06 | ND | 3.1E+03 | 3.1E+04 | 2.0E+05 | 2.0E+03 | 3.1E+04 |
| 156 | 3.0E+04 | 4.8E+05 | 3.9E+03 | 1.9E+04 | 6.5E+03 | 2.9E+06 | ND | 4.9E+03 | 5.8E+04 | 1.3E+05 | 4.0E+03 | 2.5E+04 |
| 157 | 2.1E+05 | 2.4E+06 | 2.0E+03 | 2.6E+04 | 3.3E+03 | 1.8E+07 | 8.5E+03 | 3.6E+03 | 3.6E+05 | 1.8E+06 | 6.2E+03 | 1.7E+05 |
| 194 | 8.9E+04 | 5.4E+05 | 4.0E+03 | 1.2E+04 | 1.1E+03 | 7.8E+06 | 7.7E+03 | 3.2E+03 | 9.6E+04 | 5.8E+05 | 3.7E+03 | 2.4E+05 |
| 210 | 7.2E+04 | 3.2E+05 | 3.3E+03 | 4.1E+03 | 2.6E+03 | 3.9E+06 | 1.8E+03 | 3.7E+03 | 7.2E+04 | 3.3E+05 | 4.8E+03 | 2.9E+04 |
| 257 | 7.4E+04 | 6.3E+05 | 2.5E+03 | 1.1E+04 | 1.2E+02 | 2.8E+06 | 8.7E+03 | 2.9E+03 | 2.3E+04 | 1.2E+05 | 2.6E+03 | 4.9E+04 |
| 261 | 1.3E+05 | 7.6E+05 | 4.7E+03 | 1.6E+04 | 7.4E+03 | 3.1E+06 | 1.5E+03 | 1.8E+03 | 1.2E+05 | 4.5E+05 | 4.9E+03 | 7.2E+04 |
| 282 | 4.0E+04 | 4.6E+05 | 2.5E+03 | 1.3E+04 | 2.3E+03 | 1.9E+06 | 1.5E+04 | 1.3E+03 | 6.5E+04 | 4.5E+05 | 2.0E+03 | 3.1E+04 |
| 285 | 1.6E+04 | 4.3E+05 | 5.3E+03 | 8.4E+04 | 6.2E+02 | 3.5E+06 | 7.3E+03 | 9.2E+03 | 3.0E+04 | 2.3E+05 | ND | 2.0E+04 |
| 296 | 7.1E+04 | 8.1E+05 | 1.5E+03 | 7.4E+03 | 4.1E+03 | 3.6E+06 | 8.1E+03 | 4.5E+03 | 2.0E+05 | 5.4E+05 | 2.6E+03 | 5.2E+04 |
| 305 | 1.3E+04 | 1.4E+05 | 6.5E+02 | 4.0E+03 | 3.2E+03 | 1.6E+06 | ND | 6.9E+02 | 4.1E+04 | 1.8E+05 | 1.3E+03 | 5.7E+03 |
| 315 | 6.2E+04 | 4.2E+05 | 7.6E+03 | 5.1E+03 | 3.1E+03 | 7.9E+06 | 7.2E+03 | 4.3E+03 | 7.3E+04 | 4.5E+05 | 1.0E+04 | 3.8E+04 |
| 330 | 2.8E+04 | 1.2E+05 | 2.0E+03 | 5.8E+03 | 3.5E+03 | 1.1E+06 | 3.1E+01 | 1.3E+03 | 2.9E+04 | 2.3E+05 | 1.4E+03 | 1.7E+04 |
| 331 | 6.2E+04 | 6.1E+05 | 3.4E+03 | 1.3E+04 | 3.6E+03 | 7.3E+06 | 1.0E+04 | 1.8E+03 | 1.2E+05 | 1.3E+06 | 1.9E+03 | 5.7E+04 |
| 334 | 5.1E+04 | 6.5E+05 | 4.0E+03 | 2.7E+04 | 1.7E+04 | 3.7E+06 | 4.6E+03 | 3.0E+03 | 6.8E+04 | 5.9E+05 | 2.9E+03 | 2.6E+04 |
| 336 | 9.5E+04 | 4.7E+05 | 2.7E+03 | 4.4E+04 | 1.6E+03 | 3.4E+06 | 1.2E+04 | 8.3E+03 | 6.2E+04 | 5.4E+05 | 4.2E+03 | 1.2E+05 |
| 337 | 4.2E+04 | 2.8E+05 | 2.8E+03 | 3.8E+03 | 4.3E+03 | 1.5E+06 | 5.3E+03 | 5.6E+03 | 4.9E+04 | 3.3E+05 | 1.7E+03 | 4.4E+04 |
| 339 | 3.2E+04 | 3.1E+05 | 1.6E+04 | 3.0E+04 | 1.1E+03 | 3.5E+06 | 6.6E+03 | 2.0E+03 | 6.6E+04 | 2.4E+05 | 2.5E+03 | 2.2E+04 |
| 361 | 4.7E+04 | 3.7E+05 | 8.4E+02 | 1.5E+04 | 1.3E+03 | 7.8E+06 | 3.1E+03 | 2.7E+03 | 4.8E+04 | 6.4E+05 | 6.1E+03 | 7.7E+04 |
| 363 | 7.2E+04 | 6.1E+05 | 2.7E+03 | 2.2E+04 | 2.0E+03 | 8.1E+06 | 9.9E+03 | 2.4E+03 | 9.7E+04 | 7.0E+05 | 7.0E+03 | 3.6E+04 |
| 34 | 1.2E+05 | 8.8E+05 | 3.1E+03 | 3.4E+03 | 5.1E+02 | 1.8E+06 | ND | 1.9E+03 | 6.1E+04 | 2.9E+05 | 3.1E+03 | 5.6E+04 |
| 71 | 2.2E+05 | 8.8E+05 | 1.3E+04 | 3.2E+04 | 2.2E+03 | 6.7E+06 | ND | 2.5E+03 | 4.1E+05 | 7.5E+05 | 3.1E+03 | 5.6E+05 |
| 85 | 2.3E+04 | 2.3E+05 | 1.1E+03 | 2.6E+04 | 4.1E+03 | 1.2E+06 | 1.0E+04 | 8.1E+02 | 4.8E+04 | 1.5E+05 | 3.5E+03 | 1.8E+04 |
| 88 | 3.9E+04 | 1.3E+05 | 1.5E+03 | 3.5E+03 | 1.1E+03 | 6.9E+05 | ND | 5.6E+02 | 2.4E+04 | 1.9E+05 | 2.4E+03 | 1.6E+04 |
| 99 | 1.4E+05 | 9.0E+05 | 2.1E+03 | 1.5E+04 | 5.5E+03 | 9.6E+06 | 6.7E+03 | 8.0E+03 | 1.2E+05 | 9.4E+05 | 8.5E+03 | 4.7E+04 |
| 118 | 1.7E+04 | 8.0E+04 | 3.8E+03 | 1.1E+04 | 4.8E+03 | 1.7E+06 | 4.0E+03 | 4.5E+02 | 4.4E+04 | 1.7E+05 | 1.1E+03 | 6.1E+03 |
| 146 | 6.2E+04 | 4.1E+05 | 2.9E+04 | 4.7E+04 | 4.7E+02 | 2.0E+06 | 7.1E+03 | 1.6E+04 | 6.6E+04 | 1.7E+05 | 3.8E+04 | 6.5E+04 |
| 147 | 1.8E+04 | 4.1E+05 | 2.5E+03 | 8.2E+03 | 7.3E+02 | 8.8E+05 | 1.7E+03 | 1.3E+03 | 2.3E+04 | 6.5E+05 | 2.3E+02 | 7.4E+04 |
| 158 | 1.3E+04 | 2.6E+05 | 2.6E+03 | 1.4E+04 | 4.7E+03 | 2.3E+06 | 2.9E+03 | 1.2E+03 | 2.3E+04 | 3.7E+04 | 1.9E+03 | 2.3E+04 |
| 167 | 4.1E+04 | 1.9E+05 | 2.5E+03 | 5.3E+03 | 1.8E+03 | 2.4E+06 | 1.4E+04 | 2.3E+03 | 9.5E+04 | 4.0E+05 | 2.9E+03 | 2.8E+04 |
| 171 | 1.6E+05 | 1.6E+06 | 1.7E+03 | 1.6E+04 | 4.0E+03 | 7.8E+06 | 6.0E+03 | 6.5E+03 | 2.5E+05 | 1.4E+06 | 1.4E+04 | 6.0E+04 |
| 191 | 1.2E+04 | 4.5E+05 | 1.9E+03 | 3.5E+03 | 2.5E+02 | 1.7E+06 | 3.6E+03 | 5.6E+02 | 2.1E+04 | 1.6E+05 | 2.5E+03 | 2.1E+04 |
| 211 | 9.1E+04 | 6.0E+05 | 1.7E+04 | 1.1E+04 | 1.3E+02 | 1.0E+07 | 5.5E+03 | 4.1E+03 | 2.4E+04 | 7.1E+05 | 4.3E+03 | 8.3E+04 |
| 212 | 3.6E+04 | 6.5E+04 | 1.6E+03 | 9.6E+03 | 1.1E+03 | 4.0E+06 | 8.1E+03 | 9.5E+02 | 7.5E+04 | 9.4E+04 | 3.1E+03 | 3.6E+04 |
| 247 | 1.3E+04 | 2.3E+05 | 2.0E+02 | 1.4E+04 | 2.1E+03 | 1.3E+06 | 7.1E+03 | 1.1E+03 | 2.4E+04 | 1.3E+05 | 1.3E+03 | 1.1E+04 |
| 255 | 3.8E+05 | 1.3E+06 | 7.3E+03 | 1.5E+04 | 2.5E+03 | 2.8E+06 | 3.8E+04 | 8.1E+03 | 1.1E+05 | 2.8E+06 | 2.0E+03 | 1.0E+05 |
| 259 | 7.9E+04 | 3.0E+06 | 5.9E+03 | 1.4E+04 | 7.0E+03 | 9.2E+06 | 5.1E+03 | 5.1E+03 | 1.1E+05 | 5.0E+05 | 4.8E+03 | 2.1E+04 |
| 271 | 1.5E+05 | 7.4E+05 | 9.5E+02 | 3.8E+03 | 2.6E+03 | 2.4E+06 | 3.7E+03 | 3.1E+03 | 7.1E+04 | 6.3E+05 | 4.1E+03 | 3.0E+04 |
| 287 | 4.1E+04 | 5.8E+05 | 8.7E+03 | 1.1E+04 | 2.3E+03 | 1.9E+06 | 1.5E+04 | 6.3E+02 | 8.8E+04 | 1.2E+05 | 4.7E+03 | 3.3E+04 |
| 300 | 2.6E+04 | 2.7E+05 | 1.5E+03 | 7.7E+03 | 5.0E+03 | 3.7E+06 | 7.1E+03 | 1.9E+03 | 6.7E+04 | 3.2E+05 | 8.0E+02 | 1.3E+04 |
| 306 | 4.1E+04 | 4.2E+05 | 2.0E+02 | 9.7E+03 | 2.3E+03 | 2.2E+06 | ND | 4.8E+03 | 5.6E+04 | 1.1E+06 | 4.5E+02 | 1.9E+04 |
| 314 | 3.1E+04 | 1.6E+05 | 3.7E+03 | 1.7E+04 | 1.1E+03 | 1.2E+06 | 1.9E+02 | 1.5E+03 | 2.7E+04 | 2.7E+05 | 2.8E+03 | 3.4E+04 |
| 329 | 1.5E+05 | 2.3E+05 | 8.9E+03 | 1.6E+04 | 5.3E+03 | 7.2E+06 | 7.8E+03 | 1.4E+03 | 5.7E+04 | 8.9E+05 | 1.9E+03 | 4.8E+04 |
| 335 | 3.3E+04 | 4.1E+05 | 6.5E+03 | 2.1E+04 | 7.1E+03 | 4.3E+06 | 1.8E+02 | 7.0E+03 | 6.9E+04 | 5.2E+05 | 3.9E+03 | 4.4E+04 |
| B3 | 4.1E+04 | 4.0E+05 | 3.2E+03 | 6.0E+03 | 3.8E+02 | 1.6E+06 | 7.7E+03 | 1.8E+03 | 1.8E+04 | 2.6E+05 | 3.7E+03 | 1.7E+04 |

TABLE 4

Pearson Analysis of Normalized VMTA Values for Antioxidant and DNA Repair Genes and Putative Regulatory Transcription Factors.

| AO/DNAR Genes vs TFs | NBCI n = 24 r Value | NBCI n = 24 p Value | BCI n = 25 r Value | BCI n = 25 p Value | ALL n = 49 r Value | ALL n = 49 p Value |
|---|---|---|---|---|---|---|
| CAT vs CEBPB | 0.13 | 1 | 0.18 | 1 | 0.15 | 1 |
| CAT vs CEBPG | 0.65 | 0.004 | 0.35 | 0.48 | 0.55 | <0.0006 |
| CAT vs E2F1* | 0.54 | 0.04 | 0.68 | 0.002 | 0.56 | <0.0006 |
| CAT vs E2F3 | 0.48 | 0.12 | 0.18 | 1 | 0.37 | 0.06 |
| CAT vs E2F6 | 0.26 | 1 | 0.3 | 0.84 | 0.25 | 0.48 |
| CAT vs EVI1 | −0.01 | 1 | 0.21 | 1 | 0.08 | 1 |
| ERCC1 vs CEBPB | 0.32 | 1 | 0.27 | 1 | 0.29 | 0.24 |
| ERCC1 vs CEBPG | 0.77 | <0.0006 | 0.42 | 0.24 | 0.62 | <0.0006 |
| ERCC1 vs E2F1 | 0.35 | 0.54 | 0.39 | 0.36 | 0.37 | 0.06 |
| ERCC1 vs E2F3 | 0.39 | 0.36 | 0.21 | 1 | 0.31 | 0.18 |
| ERCC1 vs E2F6 | 0.17 | 1 | 0.63 | 0.005 | 0.42 | 0.02 |
| ERCC1 vs EVI1 | −0.02 | 1 | 0.38 | 0.36 | 0.17 | 1 |
| ERCC2 vs CEBPB | 0.25 | 1 | 0.19 | 1 | 0.22 | 0.84 |
| ERCC2 vs CEBPG | 0.63 | 0.006 | 0.39 | 0.3 | 0.53 | <0.0006 |
| ERCC2 vs E2F1 | 0.39 | 0.36 | 0.32 | 0.72 | 0.33 | 0.12 |
| ERCC2 vs E2F3 | 0.58 | 0.02 | 0.22 | 1 | 0.42 | 0.02 |
| ERCC2 vs E2F6 | 0.37 | 0.42 | 0.51 | 0.06 | 0.42 | 0.02 |
| ERCC2 vs EVI1 | 0.19 | 1 | 0.29 | 0.96 | 0.23 | 0.66 |
| ERCC4 vs CEBPB | −0.35 | 0.6 | −0.11 | 1 | −0.16 | 1 |
| ERCC4 vs CEBPG | 0.24 | 1 | 0.37 | 0.42 | 0.25 | 0.48 |
| ERCC4 vs E2F1 | 0.42 | 0.24 | 0.04 | 1 | 0.2 | 1 |
| ERCC4 vs E2F3 | 0.6 | 0.01 | 0.33 | 0.6 | 0.33 | 0.12 |
| ERCC4 vs E2F6 | −0.04 | 1 | 0.04 | 1 | 0.07 | 1 |
| ERCC4 vs EVI1 | 0.24 | 1 | 0.33 | 0.66 | 0.27 | 0.36 |
| ERCC5 vs CEBPB | 0.4 | 0.3 | 0.28 | 1 | 0.33 | 0.12 |
| ERCC5 vs CEBPG | 0.79 | <0.0006 | 0.12 | 1 | 0.46 | 0.005 |
| ERCC5 vs E2F1 | 0.44 | 0.18 | 0.45 | 0.18 | 0.44 | 0.01 |
| ERCC5 vs E2F3 | 0.39 | 0.36 | −0.11 | 1 | 0.13 | 1 |
| ERCC5 vs E2F6 | 0.41 | 0.3 | 0.35 | 0.54 | 0.38 | 0.04 |
| ERCC5 vs EVI1 | 0.07 | 1 | −0.04 | 1 | 0.01 | 1 |
| GPX1 vs CEBPB | 0.49 | 0.06 | 0.24 | 1 | 0.32 | 0.12 |
| GPX1 vs CEBPG | 0.72 | <0.0006 | 0.19 | 1 | 0.4 | 0.02 |
| GPX1 vs E2F1 | 0.48 | 0.12 | 0.38 | 0.36 | 0.43 | 0.02 |
| GPX1 vs E2F3 | 0.22 | 1 | −0.004 | 1 | 0.08 | 1 |
| GPX1 vs E2F6 | 0.06 | 1 | 0.36 | 0.48 | 0.28 | 0.3 |
| GPX1 vs EVI1 | −0.06 | 1 | 0.2 | 1 | 0.1 | 1 |
| GPX3 vs CEBPB | −0.18 | 1 | 0.14 | 1 | 0.02 | 1 |
| GPX3 vs CEBPG | 0.13 | 1 | 0.01 | 1 | 0.07 | 1 |
| GPX3 vs E2F1 | −0.03 | 1 | −0.17 | 1 | −0.12 | 1 |
| GPX3 vs E2F3 | 0.32 | 0.78 | −0.2 | 1 | 0.05 | 1 |
| GPX3 vs E2F6 | −0.26 | 1 | 0.44 | 0.18 | 0.19 | 1 |
| GPX3 vs EVI1 | 0.06 | 1 | 0.08 | 1 | 0.06 | 1 |
| GSTM1-5 vs CEBPB | −0.08 | 1 | 0.43 | 0.18 | 0.17 | 1 |
| GSTM1-5 vs CEBPG | 0.25 | 1 | 0.02 | 1 | 0.16 | 1 |
| GSTM1-5 vs E2F1 | 0.51 | 0.06 | 0.23 | 1 | 0.41 | 0.02 |
| GSTM1-5 vs E2F3 | 0.29 | 0.96 | −0.16 | 1 | 0.1 | 1 |
| GSTM1-5 vs E2F6 | −0.3 | 0.9 | 0.006 | 1 | −0.1 | 1 |
| GSTM1-5 vs EVI1 | 0.22 | 1 | −0.12 | 1 | 0.07 | 1 |
| GSTM3 vs CEBPB | 0.01 | 1 | 0.06 | 1 | 0.04 | 1 |
| GSTM3 vs CEBPG | −0.007 | 1 | −0.28 | 1 | 0.01 | 1 |
| GSTM3 vs E2F1 | 0.29 | 1 | 0.35 | 0.54 | 0.34 | 0.12 |
| GSTM3 vs E2F3 | −0.31 | 0.84 | −0.49 | 0.06 | −0.4 | 0.03 |
| GSTM3 vs E2F6 | −0.11 | 1 | −0.25 | 1 | −0.16 | 1 |
| GSTM3 vs EVI1 | −0.27 | 1 | −0.25 | 1 | −0.25 | 0.54 |
| GSTP1 vs CEBPB | 0.19 | 1 | 0.38 | 0.36 | 0.28 | 0.36 |
| GSTP1 vs CEBPG | 0.74 | <0.0006 | 0.18 | 1 | 0.51 | 0.001 |
| GSTP1 vs E2F1 | 0.6 | 0.01 | 0.46 | 0.12 | 0.56 | <0.0006 |
| GSTP1 vs E2F3 | 0.32 | 0.78 | −0.25 | 1 | 0.07 | 1 |
| GSTP1 vs E2F6 | 0.1 | 1 | 0.35 | 0.48 | 0.26 | 0.42 |
| GSTP1 vs EVI1 | 0.11 | 1 | 0.13 | 1 | 0.12 | 1 |
| GSTT1 vs CEBPB | 0.03 | 1 | 0.45 | 0.12 | 0.24 | 0.6 |
| GSTT1 vs CEBPG | 0.39 | 0.36 | 0.16 | 1 | 0.3 | 0.24 |
| GSTT1 vs E2F1 | 0.07 | 1 | −0.15 | 1 | −0.05 | 1 |
| GSTT1 vs E2F3 | 0.35 | 0.54 | −0.1 | 1 | 0.17 | 1 |
| GSTT1 vs E2F6 | 0.05 | 1 | 0.21 | 1 | 0.11 | 1 |
| GSTT1 vs EVI1 | −0.26 | 1 | 0.22 | 1 | −0.04 | 1 |
| GSTZ1 vs CEBPB | 0.11 | 1 | 0.36 | 0.42 | 0.25 | 0.54 |
| GSTZ1 vs CEBPG | 0.51 | 0.06 | 0.08 | 1 | 0.28 | 0.3 |
| GSTZ1 vs E2F1 | 0.64 | 0.004 | 0.5 | 0.06 | 0.58 | <0.0006 |
| GSTZ1 vs E2F3 | 0.42 | 0.24 | 0.14 | 1 | 0.25 | 0.54 |
| GSTZ1 vs E2F6 | −0.05 | 1 | 0.48 | 0.12 | 0.32 | 0.18 |
| GSTZ1 vs EVI1 | 0.02 | 1 | 0.27 | 1 | 0.16 | 1 |
| mGST vs CEBPB | 0.31 | 0.78 | 0.35 | 0.48 | 0.32 | 0.12 |
| mGST vs CEBPG | 0.56 | 0.02 | 0.25 | 1 | 0.42 | 0.02 |
| mGST vs E2F1 | 0.58 | 0.02 | 0.54 | 0.04 | 0.58 | <0.0006 |
| mGST vs E2F3 | 0.03 | 1 | −0.15 | 1 | −0.06 | 1 |
| mGST vs E2F6 | 0.17 | 1 | 0.29 | 0.96 | 0.27 | 0.36 |
| mGST vs EVI1 | −0.16 | 1 | 0.07 | 1 | −0.04 | 1 |
| SOD1 vs CEBPB | 0.13 | 1 | 0.15 | 1 | 0.14 | 1 |
| SOD1 vs CEBPG | 0.66 | 0.002 | 0.009 | 1 | 0.36 | 0.06 |
| SOD1 vs E2F1 | 0.59 | 0.02 | 0.55 | 0.04 | 0.56 | <0.0006 |
| SOD1 vs E2F3 | 0.25 | 1 | −0.07 | 1 | 0.09 | 1 |
| SOD1 vs E2F6 | 0.12 | 1 | 0.14 | 1 | 0.14 | 1 |
| SOD1 vs EVI1 | −0.17 | 1 | 0.03 | 1 | −0.06 | 1 |
| XPA vs CEBPB | 0.31 | 0.84 | 0.42 | 0.24 | 0.31 | 0.18 |
| XPA vs CEBPG | 0.36 | 0.54 | 0.33 | 0.66 | 0.34 | 0.12 |
| XPA vs E2F1 | −0.05 | 1 | 0.22 | 1 | −0.02 | 1 |
| XPA vs E2F3 | −0.07 | 1 | 0.14 | 1 | −0.01 | 1 |
| XPA vs E2F6 | 0.55 | 0.04 | 0.46 | 0.12 | 0.4 | 0.02 |
| XPA vs EVI1 | 0.04 | 1 | 0.07 | 1 | 0.04 | 1 |
| XRCC1 vs CEBPB | 0.36 | 0.48 | 0.28 | 1 | 0.32 | 0.18 |
| XRCC1 vs CEBPG | 0.83 | <0.0006 | 0.27 | 1 | 0.591 | <0.0006 |
| XRCC1 vs E2F1 | 0.32 | 0.78 | 0.37 | 0.48 | 0.35 | 0.12 |
| XRCC1 vs E2F3 | 0.47 | 0.12 | 0.22 | 1 | 0.35 | 0.06 |
| XRCC1 vs E2F6 | 0.26 | 1 | 0.54 | 0.04 | 0.41 | 0.02 |
| XRCC1 vs EVI1 | −0.009 | 1 | 0.12 | 1 | 0.06 | 1 |

Table 4 presents correlation coefficient (r value) and level of significance (p value) for each correlation derived from Pearson's correlation analysis of normalized VMTA data in Table 2. The correlation of each of the six TFs and each of the sixteen AO or DNAR genes is determined by Pearson's correlation following logarithmic transformation, necessary due to the wide range of expression of each gene among the samples. Significance (p < 0.01) is determined using a two-tailed test following Bonferroni adjustment for multiple comparison (comparison of each of six TFs to each of the AO or DNAR genes).

*values not obtained in one BCI (see Examples).

TABLE 5

Correlation of CEBPG with Each of Ten Antioxidant or DNA Repair Genes in Non-Bronchogenic Carcinoma Individuals (NBCI) or Bronchogenic Carcinoma Individuals (BCI)

| Individuals Combined from Studies 2 and 3 | NBCI (N = 24) | | BCI (N = 25) | |
|---|---|---|---|---|
| | Correlation Coefficient | P value | Correlation Coefficient | P value |
| CEBPG | | | | |
| CAT | 0.65 | 0.0006 | 0.35 | 0.08 |
| ERCC1 | 0.77 | <0.0001 | 0.42 | 0.04 |
| ERCC2 | 0.63 | 0.001 | 0.39 | 0.05 |
| ERCC5 | 0.79 | <0.0001 | 0.12 | 0.57 |
| GPX1 | 0.72 | <0.0001 | 0.19 | 0.37 |
| GSTP1 | 0.74 | <0.0001 | 0.18 | 0.4 |
| GSTZ1 | 0.51 | 0.01 | 0.08 | 0.71 |
| mGST1 | 0.56 | 0.004 | 0.25 | 0.22 |
| SOD1 | 0.66 | 0.0004 | 0.009 | 0.97 |
| XRCC1 | 0.83 | <0.0001 | 0.27 | 0.2 |
| All genes | 0.69 +/− 0.10 | 0.003 +/− 0.004 | 0.23 +/− 0.13 | 0.36 +/− 0.29 |
| Antioxidant Genes | 0.64 +/− 0.09 | 0.004 +/− 0.004 | 0.18 +/− 0.12 | 0.46 +/− 0.33 |
| DNA Repair Genes | 0.76/−0.09 | 0.001 | 0.3 +/− 0.14 | 0.22 +/− 0.25 |

TABLE 6

Correlation of CEBPG with Each of Six Antioxidant or DNA Repair Genes in Non-Bronchogenic Carcinoma Individuals (NBCI) or Bronchogenic Carcinoma Individuals (BCI)

| Individuals Combined from Studies 2 and 3 | NBCI (N = 24) | | BCI (N = 25) | |
|---|---|---|---|---|
| | Correlation Coefficient | P value | Correlation Coefficient | P value |
| CEBPG | | | | |
| ERCC4 | 0.23 | 0.31 | 0.18 | 0.42 |
| GPX3 | 0.13 | 0.55 | 0.01 | 0.96 |
| GSTM3 | −0.007 | 0.98 | −0.28 | 0.17 |
| GSTM1-5 | 0.25 | 0.23 | 0.02 | 0.92 |
| GSTT1 | 0.23 | 0.3 | −0.01 | 0.96 |
| XPA | 0.36 | 0.09 | 0.33 | 0.11 |
| All genes | 0.20 +/− 0.12 | 0.41 +/− 0.32 | 0.04 +/− 0.20 | 0.59 +/− 0.40 |
| Antioxidant Genes | 0.15 +/− 0.12 | 0.52 +/− 0.34 | −0.07 +/− 0.14 | 0.75 +/− 0.39 |
| DNA Repair Genes | 0.30 +/− 0.09 | 0.2 +/− 0.16 | 0.26 +/− 0.11 | 0.27 +/− 0.22 |

TABLE 7

Correlation of CEBPB with Each of Ten Antioxidant or DNA Repair Genes in Non-Bronchogenic Carcinoma Individuals (NBCI) or Bronchogenic Carcinoma Individuals (BCI)

| Individuals Combined from Studies 2 and 3 | NBCI (N = 24) | | BCI (N = 25) | |
|---|---|---|---|---|
| | Correlation Coefficient | P value | Correlation Coefficient | P value |
| CEBPB | | | | |
| CAT | 0.13 | 0.54 | 0.18 | 0.4 |
| ERCC1 | 0.32 | 0.13 | 0.27 | 0.19 |
| ERCC2 | 0.25 | 0.24 | 0.19 | 0.37 |
| ERCC5 | 0.4 | 0.05 | 0.28 | 0.18 |
| GPX1 | 0.49 | 0.01 | 0.24 | 0.24 |
| GSTP1 | 0.19 | 0.37 | 0.38 | 0.06 |
| GSTZ1 | 0.11 | 0.62 | 0.36 | 0.07 |
| mGST1 | 0.31 | 0.13 | 0.35 | 0.08 |
| SOD1 | 0.13 | 0.56 | 0.15 | 0.48 |
| XRCC1 | 0.36 | 0.08 | 0.28 | 0.18 |
| All genes | 0.27 +/− 0.13 | 0.27 +/− 0.23 | 0.27 +/− 0.08 | 0.23 +/− 0.15 |
| Antioxidant Genes | 0.23 +/− 0.15 | 0.37 +/− 0.25 | 0.28 +/− 0.10 | 0.22 +/− 0.18 |
| DNA Repair Genes | 0.33 +/− 0.06 | 0.13 +/− 0.08 | 0.26 +/− 0.04 | 0.23 +/− 0.09 |

TABLE 8

Correlation of E2F1 with Each of Ten Antioxidant or DNA Repair Genes in Non-Bronchogenic Carcinoma Individuals (NBCI) or Bronchogenic Carcinoma Individuals (BCI)

| Individuals Combined from Studies 2 and 3 | NBCI (N = 24) Correlation Coefficient | P value | BCI (N = 25) Correlation Coefficient | P value |
|---|---|---|---|---|
| E2F1 | | | | |
| CAT | 0.54 | 0.007 | 0.68 | 0.0003 |
| ERCC1 | 0.35 | 0.09 | 0.39 | 0.06 |
| ERCC2 | 0.39 | 0.06 | 0.32 | 0.12 |
| ERCC5 | 0.44 | 0.03 | 0.45 | 0.03 |
| GPX1 | 0.48 | 0.02 | 0.38 | 0.06 |
| GSTP1 | 0.6 | 0.002 | 0.46 | 0.02 |
| GSTZ1 | 0.64 | 0.0007 | 0.5 | 0.01 |
| mGST1 | 0.58 | 0.003 | 0.54 | 0.006 |
| SOD1 | 0.59 | 0.003 | 0.55 | 0.006 |
| XRCC1 | 0.32 | 0.13 | 0.37 | 0.08 |
| All genes | 0.49 +/− 0.11 | 0.03 +/− 0.04 | 0.46 +/− 0.11 | 0.04 +/− 0.04 |
| Antioxidant Genes | 0.57 +/− 0.06 | 0.006 +/− 0.007 | 0.52 +/− 0.10 | 0.02 +/− 0.02 |
| DNA Repair Genes | 0.38/−0.05 | 0.08 +/− 0.04 | 0.38 +/− 0.05 | 0.07 +/− 0.04 |

TABLE 9

SNP Data for CEBPG, A, B

| Gene | Position | SNP | Assay Sample Size | Pop Data Sample Size | Tot # Pop w/Freq Data | Tot # indiv w/ Geno Data | Ave Hetero | Ave Allele Freq |
|---|---|---|---|---|---|---|---|---|
| CEBPG | Intron 1 | A/G | 63 | N/A | 0 | 331 | 0.488 | G = 0.577 A = 0.423 |
| | Overlap w/ 3' UTR | G/T | 4 | N/A | 0 | 0 | N/A | N/A |
| | Overlap w/ 3' UTR | A/G | 94 | 1494 | 1 | 331 | 0.102 | G = 0.946 A = 0.054 |
| | Overlap w/ 3' UTR | G/T | 10 | 184 | 1 | 0 | 0.039 | T = 0.980 G = 0.020 |
| | Overlap w/ 3' UTR | A/G | 8 | N/A | 0 | 0 | 0 | N/A |
| | Overlap w/ 3' UTR | A/C | 97 | 184 | 1 | 71 | 0.187 | A = 0.896 G = 0.104 |
| CEBPA | Overlap w/ 3' UTR | C/T | 24 | 372 | 2 | 269 | 0.251 | C = 0.853 T = 0.147 |
| | Overlap w /3' UTR | C/G | 18 | 184 | 1 | 0 | 0.255 | C = 0.850 G = 0.150 |
| | Overlap w/ 3' UTR | C/T | 10 | N/A | 0 | 0 | 0 | N/A |
| | Overlap w/ 3' UTR | A/G | 15 | N/A | 0 | 0 | 0 | N/A |
| | Overlap w/ 3' UTR | C/T | 2 | N/A | 0 | 0 | 0 | N/A |
| | Overlap w/ Exon 1 | G/T | 10 | N/A | 0 | 0 | 0 | N/A |
| | Overlap w/ Exon 1 | A/C | 48 | N/A | 0 | 0 | 0 | N/A |
| CEBPB | Overlap w/ Exon 1 | A/G | 2 | N/A | 0 | 0 | 0 | N/A |
| | Overlap w/ Exon 1 | C/T | 50 | 94 | 2 | 47 | 0.427 | C = 0.691 T = 0.309 |
| | Overlap w/ Exon 1 | A/G | 48 | 48 | 1 | 24 | 0.041 | G = 0.979 A = 0.021 |
| | Overlap w/ 3' UTR | A/G | 3 | 184 | 1 | 0 | 0 | G = 1.000 A = 0.000 |

TABLE 10

Target Gene SNPS

| | | | | | | | | |
|---|---|---|---|---|---|---|---|---|
| XRCC1 | 59 | C/T | | 152 | 152 | 1 | 90 | 0.013 C = 0.993 T = 0.007 |

TABLE 10-continued

Target Gene SNPS

| | | | | | | | |
|---|---|---|---|---|---|---|---|
| 59 | A/G(Genomic Reverse) | N/A | N/A | N/A | N/A | N/A | N/A |
| 72 | C/T | 207 | 152 | 1 | 90 | 0.347 | T = 0.776<br>C = 0.224 |
| 72 | A/G(Genomic Reverse) | N/A | N/A | N/A | N/A | N/A | N/A |
| 313 | A/C | 152 | 152 | 1 | 90 | 0.026 | C = 0.987<br>A = 0.013 |
| 313 | T/G(Genomic Reverse) | N/A | N/A | N/A | N/A | N/A | N/A |
| 697 | A/G | 172 | 172 | 1 | 90 | 0.012 | G = 0.994<br>A = 0.006 |
| 697 | C/T(Genomic Reverse) | N/A | N/A | N/A | N/A | N/A | N/A |

TABLE 11

| | Measurable Biological Correlate | | | | | | |
|---|---|---|---|---|---|---|---|
| Function affected by SNP | TG TA/ CEBPG TA | CEBPG TA level | Total CEBPG protein | TG TA level | In vitro Free/ Bound CEBPG | Unimeric/ heterodimeric CEBPG in NBEC | Free CEBPG/ Bound CEBPG in NBEC |
| Low CEBPG transcription | High or no change | low | Low | Low | Low | low | Low |
| Low TF Heterodimer formation | Low | High | High | Low | High | High | High |
| Unstable TF transcript | High or no change | Low | Low | Low | Low | low | low |
| Low binding of TF to TG Recognition site | low | High | High | Low | High | low | High |
| Poor sub-cellular localization of TF protein | High or no change | High | High | Low | No effect | low | low |
| Poor processing of TF for translation | Low | High | Low | Low | No effect | low | low |

TABLE 12

Loss of Correlation Between CEBPG and Each Target Gene in BCl NBEC Samples

| BCl Sample | Antioxidant or DNA Repair Target Genes | | | | | | | | | |
|---|---|---|---|---|---|---|---|---|---|---|
| | ERCC5 | XRCC1 | SOD1 | GSTZ1 | ERCC1 | ERCC2 | GPX1 | GSTP1 | mGST | CAT |
| Green shade Incicates TG Increased relative to NBCl regression line. | | | | | | | | | | |
| Hypothesis: Decreased CEBPG Transcript: Analogous to BCl₁ | | | | | | | | | | |
| 0309041 BEC | | ▓ | ▓ | | ▓ | | | | | |
| 050603 BEC | ▓ | | ▓ | | | | | | | |
| 020603 BEC | | | | | | | | | | |
| 1113032 BEC | | | ▓ | | | | | | | |
| 0909031 BEC | ▓ | | | | ▓ | ▓ | | | | |
| 061102 BEC | ▓ | ▓ | ▓ | ▓ | ▓ | | | ▓ | ▓ | |
| No shading Indicates No change in TG relative to NBCl regression line. | | | | | | | | | | |
| Hypothesis: Decreased CEBPG Transcript Analogous to BCl₂ | | | | | | | | | | |
| 102903 BEC | | | | | | | | | | |
| 050801 BEC | | | | | | | | | | |
| GCV BEC | | | | | | | | | | |
| 120803 BEC | | | | | | | | | | |
| 120803 BEC | | | | | | | | | | |
| 0912032 BEC | | | | | | | | | | |
| 013012 BEC | | | | | | | | | | |

TABLE 12-continued

Loss of Correlation Between CEBPG and Each Target Gene in BCl NBEC Samples

Red shade incicates TG decreased relative to NBCl regression line.
Hypothesis: Decreased Function of CEBPG: Analogous to BCl$_{3-5}$

| | | | | | | | | | |
|---|---|---|---|---|---|---|---|---|---|
| 010902 BEC | | | | | | | | | |
| 0416022 BEC | | | | | | | | | |
| 042800 BEC | | | | | | | | | |
| 010703 BEC | | | | | | | | | |
| 032001 BEC | | | | | | | | | |
| 022001 BEC | | | | | | | | | |
| 052501 BEC | | | | | | | | | |
| 080299 BEC | | | | | | | | | |
| 080999 BEC | | | | | | | | | |
| HP BEC | | | | | | | | | |
| 020101 BEC | | | | | | | | | |

Combination: Decreased Transcription of CEBG and Decreased Function Relative to Some TG

| | | | | | | | | | |
|---|---|---|---|---|---|---|---|---|---|
| 021904 BEC | | | | | | | | | |
| 041602 BEC | | | | | | | | | |

TABLE 13

Predicting Lung Cancer risk

| GENE | TA Cancer Risk Threshold |
|---|---|
| CEBPG | <1300 |
| E2F1 | <660 |
| E2F6 | >180 and <320 |
| XRCC1 | <20000 |
| ERCC4 | <640 |
| ERCC5 | <41000 and >110000 |
| GPX1 | <420000 and >850000 |
| GPX3 | <2500 and >5500 |
| GSTM3 | <1000 and >4000 |
| GSTP1 | <2800000 |
| GSTT1 | <7100 |
| GSTZ1 | <2000 |
| MGST1 | <28000 |
| SOD1 | <300000 and >700000 |
| CAT | <35000 |

Each Gene has a value of one (1) if its TA value meets the threshold criteria above. If it is not met, the value is zero (0). The sum of the 1's and 0's for all 15 marker genes create a biomarker for predicting Lung Cancer in each sample (See F).
Fraction of patients with Cancer with ≤6 Positive Cancer Risk Biomarkers (¹/₁₈) = 6%
Which will represent 94% sensitivity for diagnosing patients with Cancer
Fraction of patients with ≥7 Positive Cancer Risk Biomarkers that have Cancer (²⁴/₃₁) = 77%
Which will represent 77%% specificity for diagnosing patients with Cancer

---

What is claimed is:

1. A method of identifying a greater risk for developing bronchogenic carcinoma in a human subject comprising:
 (a) assaying a bronchial epithelial cell sample from the subject;
 (b) determining transcript abundance (TA) for a group of genes in the sample; wherein TA levels are determined by microarray analysis, quantitative polymerase chain reaction, or a combination of both for 7 or more genes selected from the group of genes consisting of: CEBPG, E2F1, E2F6, XRCC1, ERCC4, ERCC5, GPX1, GPX3, GSTM3, GSTP1, GSTT1, GSTZ1, MGST1, SOD1 and CAT;
 (c) comparing the TAs of step (b) to threshold levels for each gene, wherein the threshold levels comprise (molecules/$10^6$ β-actin):

| | |
|---|---|
| CEBPG | ≤3.1 |
| E2F1 | ≤2.8 |
| E2F6 | 2.2-2.5 |
| XRCC1 | ≤4.3 |
| ERCC4 | ≤2.8 |
| ERCC5 | ≤4.6 or ≥5.1 |
| GPX1 | ≤5.6 or ≥5.8 |
| GPX3 | ≤3.4 or ≥3.7 |
| GSTM3 | ≤3.0 or ≥3.6 |
| GSTP1 | ≤6.4 |
| GSTT1 | ≤3.8 |
| GSTZ1 | ≤3.3 |
| MGST1 | ≤3.4 |
| SOD1 | ≤5.5 or ≥5.8 |
| CAT | ≤4.5; and, |

(d) determining the subject as either having, or being at risk for developing, bronchogenic carcinoma when the TA levels of seven or more TAs in the test sample meet the threshold levels of step (c).

2. The method of claim 1, wherein the step (b) of determining transcript abundance includes assaying transcript abundance by:
 i) measuring a nucleic acid corresponding to each gene of the 7 or more genes selected from the group of genes relative to its competitive template;
 ii) co-measuring a nucleic acid corresponding to a housekeeping gene with its competitive template; and
 iii) obtaining a relation comparing values obtained from the co-measurements obtained from steps i) and ii).

3. The method of claim 2, wherein the nucleic acid for each gene refers to an mRNA transcript of the gene or a cDNA obtained from the mRNA.

4. The method of claim 2, wherein the relation obtained can be a comparison of values for each gene, its competitive template, the housekeeping gene, and its competitive template.

5. The method of claim 2, wherein each gene is measured relative to a reference nucleic acid.

6. A method for selecting a therapy for a subject having a greater risk for developing bronchogenic carcinoma, comprising:
 (a) assaying a bronchial epithelial cell sample from the subject;
 (b) determining transcript abundance (TA) levels for a group of genes in the sample, wherein TA levels are determined by microarray analysis, quantitative polymerase chain reaction, or a combination of both for 7 or more genes selected from the group of genes consisting of: CEBPG, E2F1, E2F6, XRCC1, ERCC4, ERCC5, GPX1, GPX3, GSTM3, GSTP1, GSTT1, GSTZ1, MGST1, SOD1 and CAT;
 (c) comparing the TA levels of step (b) to threshold levels for each gene, wherein the threshold levels comprise (molecules/$10^6$ β-actin):

| | |
|---|---|
| CEBPG | ≤3.1 |
| E2F1 | ≤2.8 |
| E2F6 | 2.2-2.5 |
| XRCC1 | ≤4.3 |
| ERCC4 | ≤2.8 |
| ERCC5 | ≤4.6 or ≥5.1 |
| GPX1 | ≤5.6 or ≥5.8 |
| GPX3 | ≤3.4 or ≥3.7 |
| GSTM3 | ≤3.0 or ≥3.6 |
| GSTP1 | ≤6.4 |
| GSTT1 | ≤3.8 |
| GSTZ1 | ≤3.3 |
| MGST1 | ≤3.4 |
| SOD1 | ≤5.5 or ≥5.8 |
| CAT | ≤4.5; |

(d) calculating a combined score from the TA levels determined in step (b) and the comparisons made in step (c), wherein the combined score is calculated by assigning a value of 1 to each gene of step (b) whose TA level meets the threshold levels of step (c) or a value of 0 to each gene of step (b) whose TA level does not meet the threshold levels of step (c), and totaling assigned values for all genes;
 (e) classifying the subject into a high or low risk group based on the combined score, wherein a combined score of 7 or more indicates a high risk; and,
 (f) selecting therapy if the subject is in the high risk group.

* * * * *

SEQUENCE LISTING

```
<160> NUMBER OF SEQ ID NOS: 69

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atcctcaccc tgaagtaccc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccatctcttg ctcgaagtcc                                              20

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
ccatctcttg ctcgaagtcc gccacccagg tccagacgca                    40

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccagaagaaa gcggtcaaga                                          20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaccttcatt ttcccctggg                                          20

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaccttcatt ttcccctggg ccagtgatga gcgggttaca                    40

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtccaaacc aaccgcacat                                          20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcaacaagc ccgtaggaac                                          20

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
agcaacaagc ccgtaggaac acgcgttcag ccatgtttaa                                40

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggttgaaaa gcaagcagaa agca                                                 24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatcccagaa aatagcctcc aatg                                                 24

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gatcccagaa aatagcctcc aatgaacatt caagccacaa gctc                           44

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgatacccca actccctcta                                                      20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaagcaggag ggaacagagc                                                      20

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 15
aaagcaggac ccaacacagc actgcacgga ccacagg           37

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgaaagcccc tccagaaaca ag           22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcagcagggg aggcagtaag tt           22

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcagcagggg aggcagtaag ttggggaggc cagaggagaa aggt           44

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggcctgctg ccatcaaaaa ta           22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgctttcgg actcccagtt t           21

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 21
ccgctttcgg actcccagtt agcgatacat caaaacgagc                           40

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctggagcccc gaggaagc                                                   18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cactgggggt ttcctttg                                                   18

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cactgggggt ttccttggaa ggccagatct tctctt                               36

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggccttcttc accagctac                                                  19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtagtccgtc ttgcccctg                                                  19

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 27
gtagtccgtc ttgcccctgt ggaactggtc ccgcaggt                                   38

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtgcatctc catgtcccgc tacta                                                 25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgatgttctt aacgtggtgc atcaa                                                 25

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgatgttctt aacgtggtgc atcaacaggc tgtggcttgc tttgt                           45

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaggaaagag aaagaagcag cagcca                                                26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caaacacaga tctggcggtc acgagg                                                26

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 33
caaacacaga tctggcggtc acgaggagct tccttcactg agttctgcga at          52

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgccggatat ccacgaaga                                                19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgctgagag cgaatgtgc                                                19

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atgctgagag cgaatgtgct taaatgcctt gggacact                           38

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctggtggtg ctcggcttcc                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caatggtctg gaagcggcgg                                               20

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 39
caatggtctg gaagcggcgg accggagacc aggtgatgag      40

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 40
gcagagccgg ggacaagaga a      21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 41
ctgctctttc tctccattga c      21

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 42
ctgctctttc tctccattga cgctcttcct gtagtgcatt ca      42

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 43
gggacgctcc tgattatgac      20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 44
gcaaaccatg gccgcttccc      20

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 45
gcaaaccatg gccgcttccc ttctccaaaa tgtccacacg                    40

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtgcgagtcg tctatggttc                                         20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agttgtgtgc ggaaatccat                                         20

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agttgtgtgc ggaaatccat tgctctgggt gatcttgttc                    40

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tccgctgcaa atacatctcc                                         20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgtttcccgt tgccattgat                                         20

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 51
tgtttcccgt tgccattgat taggacctca tggatcagca                                40

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctctacctg gacctgctgt                                                      20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggaacacagg gaacatcacc                                                      20

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggaacacagg gaacatcacc tagagcagga tggccacact                                40

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcacccccta ccctaccatc acc                                                  23

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atttcagcgc gggcattctt t                                                    21

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 57
atttcagcgc gggcattctt tccgcattct catctcagcc tcac        44

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtcggagcac ggatctacca ca        22

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttcctctgct cccctcctac cta        23

<210> SEQ ID NO 60
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttcctctgct cccctcctac ctattttcag caacctgtaa gcc        43

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgaaggtgtg gggaagcatt a        21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ttacaccaca agccaaacca c        21

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttacaccaca agccaaacga ctgatgcaat ggtctcctga ga                42

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctcggcgacg gcggctgcgg ctactggag                               29

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgtcggactt cctttgcttc ttctaatgc                               29

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tgtcggactt cctttgcttc ttctaatgct cttttttcta aatcacagtc t       51

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cccctgaaga gaccaaagca                                         20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccattgaagg ctgtgacgta                                         20

<210> SEQ ID NO 69
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 69
ccattgaagg ctgtgacgta tcagggactg gcagatg                                        37
```